US009610263B2

(12) United States Patent
Yang et al.

(10) Patent No.: US 9,610,263 B2
(45) Date of Patent: Apr. 4, 2017

(54) METHOD OF MODULATING MEMBRANE POTENTIAL OF A CELL

(75) Inventors: Dan Yang, Hong Kong (CN); Xiang Li, Hong Kong (CN); Bing Shen, Hong Kong (CN); Xiao-Qiang Yao, Hong Kong (HK)

(73) Assignees: VERSITECH LIMITED, Hong Kong (CN); THE CHINESE UNIVERSITY OF HONG KONG, Hong Kong (CN)

( * ) Notice: Subject to any disclaimer, the term of this patent is extended or adjusted under 35 U.S.C. 154(b) by 695 days.

(21) Appl. No.: 12/337,642

(22) Filed: Dec. 18, 2008

(65) Prior Publication Data

US 2009/0163595 A1 Jun. 25, 2009

Related U.S. Application Data

(60) Provisional application No. 61/015,189, filed on Dec. 19, 2007.

(51) Int. Cl.
*A61K 31/33* (2006.01)
*A61K 31/166* (2006.01)

(52) U.S. Cl.
CPC .................................. *A61K 31/166* (2013.01)

(58) Field of Classification Search
None
See application file for complete search history.

(56) References Cited

U.S. PATENT DOCUMENTS 5,667,962 A * 9/1997 Brunengraber .......... A01N 1/02
435/1.2
6,261,836 B1 7/2001 Cech et al.

FOREIGN PATENT DOCUMENTS

| CN | 1671654 | 9/2005 |
|---|---|---|
| JP | 2000072736 | 3/2000 |
| WO | WO 03/059937 A2 | 7/2003 |

OTHER PUBLICATIONS

Li et al (J Am Chem Soc 129:7264-7265, 2007).*
Gao et al (Am J Physiol Lung Cell Mol Physiol 281:L24-L30, 2001).*
Han (Advances in Characterization of Pharmaceutical Hydrates. Trends in Bio/Pharmaceutical Industry, pp. 25-29. Mar. 2006).*
Vippagunta et al (Adv Drug Deliv Rev 48:3-26, 2001).*
Schumacher et al (J Agricultural and Food Chem 25:310-320, 1977).*
Gang Deng, et al., A Synthetic Ionophore That Recognizes Negatively Charged Phospholipid Membranes, J. Am. Chem. Soc. 1996, vol. 118, No. 37, p. 8975.
George W. Gokel, et al., Functional, synthetic organic chemical models of cellular ion channels. Biorganic & Medicinal Chemistry. 2004, vol. 12, p. 1291-1304.
J. Middleton Boon et al. Synthetic membrane transporters. Current Opinion in Chemical Biology. 2002, 6: 749-756.
Manette Merritt et al., Sterol-Polyamine Conjugates as Synthetic Ionophores, J. Am. Chem. Soc. 1998, vol. 120, No. 33, p. 8494-8501.
Naomi Sakai et al. Rigid-Rod Molecules in Biomembrane Models: From Hydrogen-Bonded Chains to Synthetic Multifunctional Pores. Acc. Chem. 2005, vol. 38(2), p. 79-87.
Naomi Sakai et al., Synthetic Multifunctional pores: lessons from rigid-rod β-barrels. Chem. Commun. 2003, p. 2514.
Paul H. Schlesinger, et al., SCMTR: A Chloride-Selective, Membrane-Anchored Peptide Channel that Exhibits Voltage Gating, J. Am. Chem. Soc. 2002, vol. 124, No. 9, p. 1848.
Philip A. Gale et al. Co-transport of H+/Cl− by a synthetic prodigiosin mimic, Chem. Commun., 2005, p. 3773-3775.
Stefan Matile et al., Recent synthetic ion channels and pores. Tetrahedron 60 (2004) p. 6405-6435.
Sidorov et al., Chloride Transport Across Lipid Bilayers and Transmembrane Potential Induction by an Oligophenoxyacetamide. J. Am. Chem. Soc. 2003, vol. 125, No. 10, p. 2840.
Sidorov et al., Ion Channel Formation from a Calix[4]arene Amide That binds HCl. J. Am. Chem. Soc. 2002, vol. 124, No. 10, p. 2267.
Thomas J. Jentsch et al., Ion Channels: Function unravelled by dysfunction. Nature Cell Biology, 2004, vol. 6, No. 11, p. 1039.
Koulov et al., Chloride Transport Across Vesicle and Cell Membranes by Steroid-Based Receptors. Angew. Chem. Int. Ed. 2003, 42, 4931-4933.
Abo-Ghalia M. et al., Amino Acids, 2004, vol. 26, No. 3, pp. 283-289.
Bose et al., Chemical Communications, 2006, 30, pp. 3196-3198.
Hassan Saad S. M. et al., Analytica Chimica Acta, 2003, vol. 482, No. 1, pp. 9-18.
Hassan Saad S. M. et al., Talanta, 2003, vol. 60, No. 1, pp. 81-91.
Ross et al., Tetrahedron, 2002, vol. 58, No. 3, pp. 6127-6133.
Tan et al., Journal of Separation Science, 2006, vol. 29, No. 10, pp. 1407-1411.
Wang Jian et al., Youji Huaxue, 2005, vol. 25, No. 7, pp. 850-853. English abstract of C20.
International Search Report of PCT/CN2007/003691, mailed Mar. 27, 2008.
Written Opinion of PCT/CN2007/003691, mailed Mar. 27, 2008.
Armstrong CM, Voltage-dependent ion channels and their gating. Physiol. Rev., 1992, 72:5-13.
Sisson A, Shah MR, Bhosalea S, Matile S, Synthetic ion channels and pores (2004-2005). Chem. Soc. Rev., 2006, 35:1269-1286.
Davis AP, Sheppard DN, Smith BD, Development of synthetic membrane transporters for anions. Chem. Soc. Rev., 2007, 36:348-357.
Reddy GL et al, Synthetic peptides and four-helix bundle proteins as model systems for the pore-forming structure of channel proteins. J. Biol. Chem., 1993, 268:14608-14614.

(Continued)

*Primary Examiner* — Craig Ricci
(74) *Attorney, Agent, or Firm* — Saliwanchik, Lloyd & Eisenschenk

(57) ABSTRACT

Provided herein are methods of modulating membrane potential of a cell membrane using self-assembling compounds. Also provided herein are methods of regulating a natural voltage-dependent ion channel in a cell membrane using the self-assembling compounds disclosed herein. Further provided herein are methods of treating, preventing and/or managing a disease that is related to the abnormal membrane potential responses by using the self-assembling compounds disclosed herein.

5 Claims, 24 Drawing Sheets

(56) References Cited

OTHER PUBLICATIONS

Oblatt-Montal M et al, Identification of an ion channel-forming motif . . . the cystic fibrosis chloride channel. Proc. Nat. Acad. Sci. U.S.A., 1994, 91:1495-1499.

Mitchell KE et al, A synthetic peptide based on a glycine-gated chloride channel . . . in isolated epithelial cells. Biochim. Biophys. Acta (Biomembranes), 2000, 1466:47-60.

Broughman JR et al, NH2-terminal modification . . . increases capacity for epithelial anion secretion. Am. J. Physiol. Cell. Physiol., 2001, 280:C451-C458.

Jiang C et al, Partial correction of defective Cl-secretion in cystic fibrosis epithelial cells . . . , Am. J. Physiol. Cell. Physiol., 2001, 281:L1164-L1172.

Baumeister B, Sakai N, Matile S, Giant artificial ion channels formed by self-assembled, cationic rigid-rod b-barrels. Angew. Chem. Int. Ed, 2000, 39:1955-1958.

Gorteau V, Bollot G, Mareda J, Perez-Velasco A, Matile S, Rigid oligonaphthalenediimide rods as transmembrane anion-p slides. J. Am. Chem. Soc., 2006, 128:14788-14789.

Li X, Shen B, Yao XQ, Yang D, A small synthetic molecule forms chloride channels to mediate chloride transport across cell membranes. J. Am. Chem. Soc., 2007, 129:7264-7265.

Sakai N et al, Electrostatics of cell membrane recognition: structure and activity of neutral and cationic rigid push-pull rods . . . , J. Am. Chem. Soc., 2001, 123:2517-2524.

Sakai N, Matile S, Recognition of Polarized Lipid Bilayers by p-Oligophenyl Ion Channels: From Push-Pull Rods to Push-Pull Barrels. J. Am. Chem. Soc., 2002, 124:1184-1185.

Morgan KG, Calcium and vascular smooth muscle tone. Am. J. Med., 1987, 82 (suppl 3B):9-15.

Robert R et al, Disruption of CFTR chloride channel alters mechanical properties and cAMP-dependent Cl-transport . . . , 2005, J. Physiol. 568:483-495.

West, A. R. (1988). Solid State Chemistry and its Applications. pp. 358 and 365. Wiley, New York.

\* cited by examiner

METHOD OF MODULATING MEMBRANE POTENTIAL OF A CELL

PRIOR RELATED APPLICATIONS

This application claims priority to U.S. Provisional Patent Application Ser. No. 61/015,189, filed Dec. 19, 2007, which is incorporated herein by reference in its entirety.

FIELD

Provided herein are methods of modulating membrane potential of a cell membrane using self-assembling compounds. Also provided herein are methods of regulating a natural voltage-dependent ion channel in a cell membrane using the self-assembling compounds disclosed herein. Further provided herein are methods of treating, preventing and/or managing a disease that is related to the abnormal membrane potential responses by using the self-assembling compounds disclosed herein.

BACKGROUND

Membrane potential, i.e., the electrical potential difference across the membrane of a living cell, is an intrinsic character of the live cell. Many important physiological processes, such as neuronal signaling, muscle contraction, cardiovascular function and immune response, involve a change in membrane potential. Generally, membrane potentials in cells depend on, inter alia, three factors: 1) the concentration of ions on the inside and outside of the cell; 2) the permeability of the cell membrane to those ions through specific ion channels; and 3) by the activity of electrogenic pumps that maintain the ion concentrations across the membrane. Therefore, ion channels that can selectively mediate the transfer of ions across the membrane of a cell may play a crucial role in establishing and controlling the membrane potential of the cell.

While ion channels may control the membrane potential of a cell, the membrane potential, however in a reverse way, can regulate the functions of many ion channels, especially voltage-dependent ion channels. For example, a change in membrane potential caused by the opening of a certain ion channel may affect behaviors of other ion channels and induce an action cascade of them, e.g., the contraction of muscle cells. In fact, abnormal membrane potential responses have been implicated in many severe human diseases such as hypertension, autosomal-dominant long-QT syndrome with deafness, autosomal-reccessive long-QT syndrome, benign familial neonatal convulsions, Long-QT syndrome, Long-QT syndrome with dysmorphic features, generalised epilepsy with febrile seizures (GEFS+), generalised epilepsy with febrile and afebrile seizures, paramyotonia congenita, potassium-aggravated myotonia hyperkalaemic periodic paralysis or Brugada syndrome.

While most studies have focused on natural ion channels, it is desirable to create synthetic ion channel systems that mimic biological functions of natural ion channels for controlling membrane potential and/or regulating natural voltage-dependent ion channels. To date, however, there is still no synthetic ion channel reported to be capable to set the membrane potentials and/or regulate natural voltage-dependent ion channels in living systems. Therefore, there is a need for new synthetic ion channels that can modulate membrane potential and/or regulate natural voltage-dependent ion channels and their physiological functions in living cells and tissues. Further, there is a need for methods of treating or preventing conditions and diseases that is related to the abnormal membrane potential responses.

SUMMARY

Provided herein are methods of using self-assemble compounds to modulate membrane potential of a cell membrane; to regulate a natural voltage-dependent ion channel in a cell membrane; or to treat, manage or prevent a disease that is related to the abnormal membrane potential responses.

In one aspect, provided herein are methods of modulating membrane potential of a cell membrane comprising the steps of: (a) forming a synthetic anion channel in the cell membrane; and (b) shifting the membrane potential toward the equilibrium potential of the anion in the cell. In some embodiments, the methods further comprise a step of imposing an anion gradient across the cell membrane.

In another aspect, provided herein are methods of regulating a natural voltage-dependent ion channel in a cell membrane comprising the steps of: (a) forming a synthetic anion channel in the cell membrane; (b) shifting the membrane potential toward the equilibrium potential of the anion in the cell; and (c) regulating the natural voltage-dependent ion channel, wherein the self-assembling compound has formula (I) as defined herein. In some embodiments, the methods further comprise a step of imposing an anion gradient across the cell membrane. In other embodiments, the natural voltage-dependent ion channel is a voltage-dependent sodium channel, potassium channel or calcium channel. In further embodiments, the natural voltage-dependent ion channel is a voltage-dependent calcium channel.

In another aspect, provided herein are methods of regulating the intracellular calcium concentration of a cell comprising the steps of (a) forming a synthetic anion channel in the cell membrane; (b) shifting the membrane potential toward the equilibrium potential of the anion in the cell; (c) regulating a natural voltage-dependent calcium channel; and (d) regulating the intracellular calcium concentration of the cell.

In another aspect, provided herein are methods of regulating the tension of a muscle cell comprising the steps of (a) forming a synthetic anion channel in the cell membrane; (b) shifting the membrane potential toward the equilibrium potential of the anion in the cell; (c) regulating a natural voltage-dependent calcium channel; (d) regulating the intracellular calcium concentration of the cell; and (e) regulating the tension of the muscle cell.

In another aspect provided herein are methods of regulating a vascular tone comprising the steps of (a) forming a synthetic anion channel in the membrane of a vascular smooth muscle cell; (b) shifting the membrane potential toward the equilibrium potential of the anion in the cell; (c) regulating a natural voltage-dependent calcium channel; (d) regulating the intracellular calcium concentration of the cell; (e) regulating the tension of the vascular smooth muscle cell; and (f) regulating the vascular tone.

In some embodiments, the cell is a muscle cell. In other embodiments, the cell is a smooth muscle cell. In further embodiments, the cell is a vascular smooth muscle cell. In still further embodiments, the natural voltage-dependent calcium channel is L-type calcium channel.

In some embodiments, the anion is fluoride, chloride, bromide, iodide, nitrate, nitrite, sulfate, bisulfate, carbonate, bicarbonate, phosphate, hydrogen phosphate, dihydrogen phosphate or acetate. In other embodiments, the anion is chloride. In further embodiments, the anion channel is a chloride channel. In still further embodiments, the anion gradient is a chloride gradient. In still further embodiments, the cell membrane comprises a lipid bilayer.

In another aspect, provided herein are methods of treating, managing or preventing a human disease that is related to the abnormal membrane potential responses, the method comprising administering a plurality of molecules of a self-assembling compound having formula (I) as defined below, or a pharmaceutically acceptable salt, solvate, polymorph or stereoisomer thereof.

In some embodiments, the disease is hypertension, autosomal-dominant long-QT syndrome with deafness, autosomal-reccessive long-QT syndrome, benign familial neonatal convulsions, Long-QT syndrome, Long-QT syndrome with dysmorphic features, generalised epilepsy with febrile seizures (GEFS+), generalised epilepsy with febrile and afebrile seizures, paramyotonia congenita, potassium-aggravated myotonia hyperkalaemic periodic paralysis or Brugada syndrome. In other embodiments, the disease is hypertension, autosomal-dominant long-QT syndrome with deafness, autosomal-reccessive long-QT syndrome, benign familial neonatal convulsions, Long-QT syndrome, or Long-QT syndrome with dysmorphic features. In further embodiments, the self-assembling compound or a pharmaceutically acceptable salt, solvate or stereoisomer thereof is inserted into the lipid bilayer of a cell of the mammal. In still further embodiments, the mammal is a human.

In another aspect, provided herein are methods of treating, managing or preventing a human disease that is related to the abnormal membrane potential responses, the method comprising administering a pharmaceutical composition comprising the self-assembling compound having formula (I) as defined below, or a pharmaceutically acceptable salt, solvate, polymorph or stereoisomer thereof.

In some embodiments, the pharmaceutical composition further comprises a carrier. In certain embodiments, the pharmaceutical composition further comprises at least an ingredient selected from the group consisting of excipients, carriers, diluents, and combinations thereof. In other embodiments, the pharmaceutical composition is in a single unit dosage form. In further embodiments, the pharmaceutical composition is in a single unit dosage form suitable for inserting into the lipid bilayer of a mammalian cell.

In some embodiments, the synthetic anion channel is formed by a plurality of molecules of a the self-assembling compounds having formula (I):

(X—H$_{DA}$)$_n$Y    (I)

wherein X is an unsubstituted or substituted hydrocarbyl or heterocyclyl;

n is an integer from 1 to 6;

Y is a monovalent, divalent, trivalent, tetravalent, pentavalent or hexavalent linking group formed by removing one, two, three, four, five and six hydrogen atoms respectively from an unsubstituted or substituted hydrocarbon (e.g., alkane, alkene and alkyne), carbocycle (e.g., aliphatic carbocycle such as cyclohexane, or arene such as benzene) or heterocycle (e.g., heteroarene such as pyridine); and $H_{DA}$ is a divalent group having the formula (II), (III), (IIIA), (IIIB), (IIIC), (IIID), (IIIE), (IV) or (IVB):

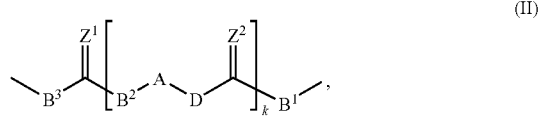
(II)

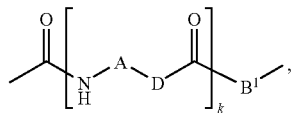
(III)

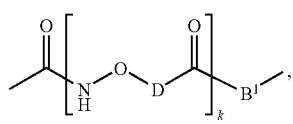
(IIIA)

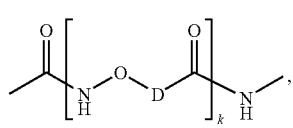
(IIIB)

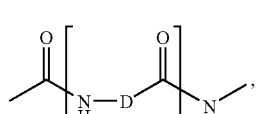
(IIIC)

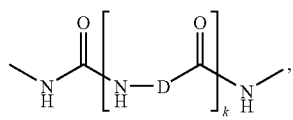
(IIID)

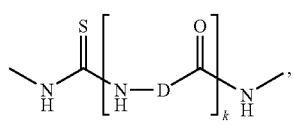
(IIIE)

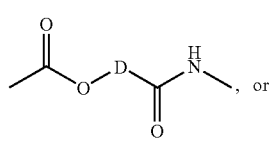
(IV)

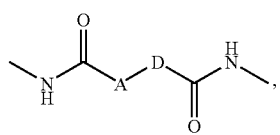
(IVB)

wherein each of $Z^1$ and $Z^2$ is independently O, S or $NR^1$;

each of A, $B^2$, and D is independently O, S, $NR^2$ or a substituted or unsubstituted $C_{1-10}$ alkylene;

each of $B^1$ and $B^3$ is independently a bond, O, S, $NR^2$ or a substituted or unsubstituted $C_{1-10}$ alkylene; and k is an integer from 1 to 20, where each of $R^1$ and $R^1$ is independently H, acyl, hydrocarbyl, carbocyclyl or heterocyclyl and at least one of B1 and B2 of formula (II) is NH.

In other embodiments, $H_{DA}$ of formula (I) is represented by formula (III):

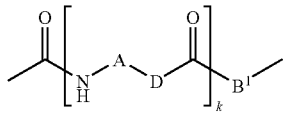

(III)

wherein k is an integer from 1 to 20;

A is O, S, $NR^2$ or a substituted or unsubstituted $C_{1-10}$ alkylene where $R^2$ is H, acyl, hydrocarbyl, carbocyclyl or heterocyclyl;

$B^1$ is O or NH; and

D is $C_{1-3}$ alkylene or $C_{1-3}$ alkylene substituted with one or more hydrocarbyl or heterocyclyl.

In certain embodiments, $H_{DA}$ of formula (I) is represented by formula (IV):

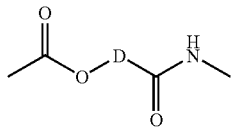

(IV)

wherein D is $C_{1-3}$ alkylene or $C_{1-3}$ alkylene substituted with one or more hydrocarbyl or heterocyclyl.

In certain embodiments, $H_{DA}$ of formula (I) is represented by formula (IVB):

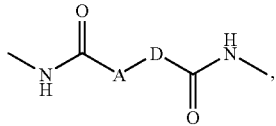

(IVB)

wherein A is O, S, $NR^2$ or a substituted or unsubstituted $C_{1-10}$ alkylene where $R^2$ is H, acyl, hydrocarbyl, carbocyclyl or heterocyclyl; and D is $C_{1-3}$ alkylene or $C_{1-3}$ alkylene substituted with one or more hydrocarbyl or heterocyclyl.

In some embodiments, n of formula (I) of the self-assembling compound disclosed herein is 1. In other embodiments, n is 2 or 3, and at least two of the X—$H_{DA}$ units are the same. In further embodiments, n is 2 or 3, and at least two of the X—$H_{DA}$ units are different.

In some embodiments, X of formula (I) of the self-assembling compound disclosed herein is hydrocarbyl or substituted hydrocarbyl. In other embodiments, X is hydrocarbyl or substituted hydrocarbyl comprising 1 to 14 carbon atoms. In further embodiments, X is alkyl or substituted alkyl having 1 to 14 carbon atoms. In still further embodiments, X is isobutyl.

In some embodiments, Y of formula (I) of the self-assembling compound disclosed herein is a divalent or trivalent linking group formed by removing two or three hydrogen atoms respectively from an unsubstituted or substituted alkane, alkene or alkyne. In other embodiments, Y is a divalent or trivalent linking group formed by removing two or three hydrogen atoms respectively from an unsubstituted or substituted $C_{2-12}$ alkane, alkene or alkyne. In further embodiments, Y is unsubstituted or substituted propylene or propenylene.

In certain embodiments, Y of formula (I) of the self-assembling compound disclosed herein is a divalent or trivalent linking group formed by removing two or three hydrogen atoms respectively from an unsubstituted or substituted monocyclic, bicyclic or tricyclic aromatic carbocycle. In other embodiments, Y is a divalent or trivalent linking group formed by removing two or three hydrogen atoms respectively from an unsubstituted or substituted arene such as benzene.

In some embodiments, Y of formula (I) of the self-assembling compound disclosed herein is a divalent or trivalent linking group formed by removing two or three hydrogen atoms respectively from an unsubstituted or substituted monocyclic, bicyclic or tricyclic heterocycle. In other embodiments, Y is a divalent or trivalent linking group formed by removing two or three hydrogen atoms respectively from an unsubstituted or substituted heteroarene such as pyridine.

In certain embodiments, $H_{DA}$ of formula (I) of the self-assembling compound disclosed herein comprises at least one primary amide or secondary amide group.

In some embodiments, D of formula (II), (III), (IV) or (IVB) is $C_{1-3}$ alkylene substituted with at least an alkyl, aryl, substituted alkyl or substituted aryl group. In other embodiments, D is $C_{1-3}$ alkylene substituted with at least an isobutyl group. In still further embodiments, D is methylene substituted with an isobutyl.

In certain embodiments, A of formula (II) or (III) is a bond; D is methylene or substituted methylene; and k is 1. In further embodiments, A of formula (II) or (III) is O; D is methylene or substituted methylene; and k is 1. In still further embodiments, Y is arylene, heteroarylene, alkylene or alkenylene; and each X is an unsubstituted or substituted hydrocarbyl having 1 to 14 carbon atoms.

In some embodiments, the self-assembling compound disclosed herein is one of Examples 1-42, or a salt, solvate, polymorph or stereoisomer thereof.

In further embodiments, the self-assembling compound is

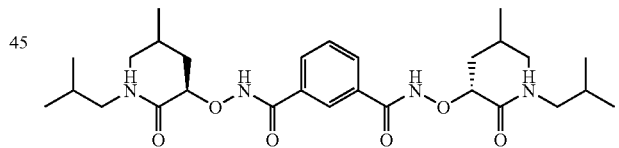

or a salt, solvate, polymorph or stereoisomer thereof.

BRIEF DESCRIPTION OF THE FIGURES

FIG. 4a depicts the chemical structure of Example 2. FIG. 4b depicts the crystal structure of Example 2 in stick representation where carbon, hydrogen, nitrogen and oxygen atoms are represented by grey, white, blue and red sticks respectively. Two eight-membered-ring intramolecular hydrogen bonds having a bond length of 2.13 Å are shown as green dashed lines. FIGS. 4c and 4d depicts the top view and side view respectively of the solid-state packing of Example 2. The CH hydrogen atoms in FIGS. 4c and 4d are omitted for clarity. Intermolecular hydrogen bonds, shown as green solid lines in FIG. 4d, link and align adjacent molecules together to form a pore-structure.

FIG. 17A-13 shows the vasorelaxant effects of increasing the concentrations of Example 2 on mouse aorta preconstricted by (A) the 60 mM K$^+$ solution; and (B) the 10 μm of α-adrenergic agonist phenylephrine (PE), respectively.

DEFINITIONS

Figure 1:
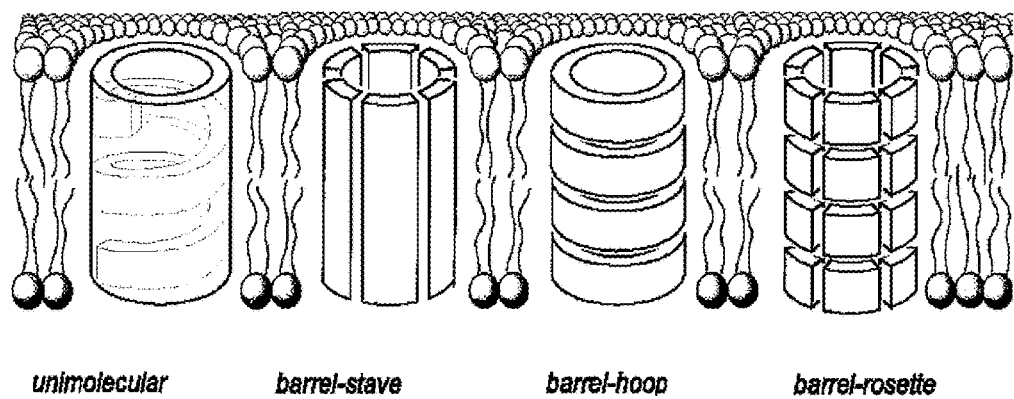
FIG. 1 depicts some classifications of synthetic ion channels based on their structures or "designs."

To facilitate the understanding of the subject matter disclosed herein, a number of terms, abbreviations or other shorthand as used herein are defined below. Any term, abbreviation or shorthand not defined is understood to have the ordinary meaning used by a skilled artisan contemporaneous with the submission of this application.

"pS" means picoSiemens.
"mM" means millimolar.
"uM" means M=micromolar.
"nM" means nanomolar.
"Anion" means a negatively-charged ion.
"Cation" means a positively-charged ion.
"Bilayer membrane" or "lipid bilayer" refers to a bimolecular thick assembly that forms the permeability barrier surrounding eukaryotic cells and plays a similar role in intracellular compartments, liposomes, and other organelles. This membrane is comprised of any of a large number of amphipathic lipid molecules but in cells it is primarily comprised of phospholipids.

"Cell" refers to prokaryotic cell, yeast cell, eukaryotic cell, plant cell, human cell, animal cell, and in one embodiment, a mammalian cell.

"Membrane" refers to a thin, semi-permeable barrier that separates two liquid phases which may have the same or different compositions.

"Cell membrane" refers to a selectively permeable lipid bilayer coated by proteins. The cell membrane comprises the outer layer of a cell.

"Channel" or "ion channel" refers to an aqueous diffusion pathway for membrane impermeant compounds usually formed by a pore within a cell membrane permitting the transfer of neutral or ionic species through it from one side of the membrane to the other.

"Supramolecular assembly" refers to a well defined complex of molecules held together by noncovalent bonds such as van de Waals force or hydrogen bonds. A supramolecular assembly can comprise two or more molecules. The supramolecular assembly can be in any form or shape such as sphere, cylinder, disk, or sheet which can be solid or hallow. In some embodiments, the supramolecular assembly is in the form of hallow cylinder. In other embodiments, the supramolecular assembly is in the form of a channel with a pore. The dimensions of supramolecular assemblies can range from nanometers to micrometers.

"Self-assembly" refers to the assembly of molecules without guidance or management from an outside source. There are generally two types of self-assembly, intramolecular self-assembly and intermolecular self-assembly. Intramolecular self-assembling molecules are generally complex polymers having the ability to assemble from the random coil conformation into a well-defined stable structure. Intermolecular self-assembly is the ability of molecules to form supramolecular assemblies.

"Self-assembling compound" or "self-assembling molecule" refers to the compound or molecule that can form a supramolecular assembly through a intermolecular self-assembly process.

"Hydrogen bond donor" refers to a group having at least one hydrogen atom attached to a strongly electronegative heteroatom, including oxygen, nitrogen and sulfur.

"Hydrogen bond acceptor" refers to a strongly electronegative heteroatom, including oxygen, nitrogen, sulfur, fluorine, chlorine, and bromine.

"Liposome" refers to an artificial sac, usually spherical, consisting of one (unilamellar) or more (multilamellar) bilayer membranes of phospholipid that encloses an aqueous core and in significant ways mimics biological membranes. The term liposome is sometimes used interchangeably with "vesicle."

"Unilamellar" refers to the bilayer membrane of phospholipid liposomes consists of a single layer.

"Multilamellar" refers to the bilayer membrane of phospholipid liposomes consists of more than one concentric layer, structurally analogous to an onion.

"Selectivity" refers to a measurable preference for one species over another, including cation over anion, anion over cation, one cation over a different cation, or one anion over a different anion.

"Transport" refers to the movement of an ion or other species across a membrane boundary.

"Amino" refers to a primary, secondary, or tertiary amine which may optionally be hydrocarbyl, substituted hydrocarbyl or heteroatom substituted. Specifically included are secondary or tertiary amine nitrogen atoms which are members of a heterocyclic ring. Also specifically included, for example, are secondary or tertiary amino groups substituted by an acyl moiety.

"Alkyl" refers to a fully saturated acyclic monovalent radical containing carbon and hydrogen, and which may be branched or a straight chain. Examples of alkyl groups are methyl, ethyl, n-butyl, t-butyl, n-heptyl, and isopropyl. Unless otherwise indicated, the alkyl groups described herein are preferably lower alkyl containing from one to ten carbon atoms in the principal chain and up to 20 carbon atoms, as exemplified by methyl, ethyl, n-butyl, i-butyl, t-butyl, isoamyl, n-pentyl, and isopentyl.

"Alkenyl" refers to a monovalent or divalent unsaturated, preferably monounsaturated, radical containing carbon and hydrogen, and which may be cyclic, branched or a straight chain. Unless otherwise indicated, the alkenyl groups described herein are preferably lower alkyl containing from two to eight carbon atoms in the principal chain and up to 20 carbon atoms, as exemplified by ethenyl, propenyl, isopropenyl, butenyl, isobutenyl, hexenyl, and the like.

"Alkynyl" refers to a lower alkyl containing from two to eight carbon atoms in the principal chain and up to 20 carbon atoms. They may contain straight or branched chain, as exemplified by ethynyl, propynyl, isopropynyl, butynyl, isobutynyl, hexynyl, and the like.

"Aromatic" refers to aryl or heteroaryl.

"Aryl" refers to optionally substituted carbocyclic aromatic groups, preferably monocyclic or bicyclic groups containing from 6 to 12 carbon atoms in the ring portion, such as phenyl, biphenyl, naphthyl, substituted phenyl, substituted biphenyl or substituted naphthyl. Phenyl and substituted phenyl are the more preferred aryl.

"Halogen" or "halo" refers to fluorine, chlorine, bromine and iodine.

"Heteroatom" shall mean atoms other than carbon and hydrogen.

"Heterocyclo" or "heterocyclyl" refers to optionally substituted, fully saturated or unsaturated, monocyclic or bicyclic, aromatic or nonaromatic groups having at least one heteroatom in at least one ring, and preferably 5 or 6 atoms in each ring. The aromatic heterocyclyl (i.e., heteroaryl) group preferably has 1 or 2 oxygen atoms, 1 or 2 sulfur atoms, and/or 1 to 4 nitrogen atoms in the ring, and may be bonded to the remainder of the molecule through a carbon or heteroatom. Non-limiting examples of heteroaryl include furyl, thienyl, thiazolyl, pyridyl, oxazolyl, pyrrolyl, indolyl, quinolinyl, or isoquinolinyl and the like. Non-limiting examples of substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

"Hydrocarbon" or "hydrocarbyl" refers to organic compounds or radicals consisting exclusively of the elements carbon and hydrogen. Hydrocarbyl includes alkyl, alkenyl, alkynyl, and aryl moieties. Hydrocarbyl also includes alkyl alkenyl, alkynyl, and aryl moieties substituted with other aliphatic, cyclic or aryl hydrocarbon groups, such as alkaryl, alkenaryl and alkynaryl. In some embodiments, "hydrocarbon" or "hydrocarbyl" comprises 1 to 20 carbon atoms.

"Hydrocarbylene" is a divalent group formed by removing two hydrogen atoms from a hydrocarbon, the free valencies of which are not engaged in a double bond, e.g. 1,3-phenylene, propane-1,3-diyl, and methylene.

"Substituted" as used herein to describe a compound or chemical moiety means that at least one hydrogen atom of that compound or chemical moiety is replaced with a second chemical moiety. The second chemical moiety can be any desired substituent that does not adversely affect the desired activity of the compound. Examples of substituents are those found in the exemplary compounds and embodiments disclosed herein, as well as halogen; alkyl, heteroalkyl; alkenyl; alkynyl; aryl, heteroaryl, hydroxyl; alkoxyl; amino; nitro; thiol; thioether; imine; cyano, isocyanate, thioisocyanate, amido; phosphonato; phosphine; carboxyl; thiocarbonyl; sulfonyl; sulfonamide; ketone; aldehyde; ester; oxo; haloalkyl (e.g., trifluoromethyl); carbocyclic cycloalkyl, which can be monocyclic or fused or non-fused polycyclic (e.g., cyclopropyl, cyclobutyl, cyclopentyl or cyclohexyl) or a heterocycloalkyl, which can be monocyclic or fused or non-fused polycyclic (e.g., pyrrolidinyl, piperidinyl, piperazinyl, morpholinyl or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl or benzofuranyl); amino (primary, secondary or tertiary); o-lower alkyl; o-aryl, aryl; aryl-lower alkyl; —$CO_2CH_3$; —$CONH_2$; —$OCH_2CONH_2$; —$NH_2$; —$SO_2NH_2$; —$OCHF_2$; —$CF_3$; —$OCF_3$; —NH(alkyl); —N(alkyl)$_2$; —NH(aryl); —N(alkyl)(aryl); —N(aryl)$_2$; —CHO; —CO(alkyl); —CO(aryl); —$CO_2$(alkyl); and —$CO_2$(aryl); and such moieties can also be optionally substituted by a fused-ring structure or bridge, for example —$OCH_2O$—. These substituents can optionally be further substituted with a substituent selected from such groups. All chemical groups disclosed herein can be substituted, unless it is specified otherwise. For example, "substituted" alkyl, alkenyl, alkynyl, aryl, hydrocarbyl or heterocyclo moieties described herein are moieties which are substituted with a hydrocarbyl moiety, a substituted hydrocarbyl moiety, a heteroatom, or a heterocyclo. Further, substituents may include moieties in which a carbon atom is substituted with a heteroatom such as nitrogen, oxygen, silicon, phosphorus, boron, sulfur, or a halogen atom. These substituents may include halogen, heterocyclo, alkoxy, alkenoxy, alkynoxy, aryloxy, hydroxy, protected hydroxy, keto, acyl, acyloxy, nitro, amino, amido, cyano, thiol, ketals, acetals, esters and ethers.

"Pharmaceutically acceptable salt" includes, but is not limited to, salts of acidic or basic groups that may be present in the compounds of the invention. Compounds of the invention that are basic in nature are capable of forming a wide variety of salts with various inorganic and organic acids. The acids that may be used to prepare pharmaceutically acceptable salts of such basic compounds are those that form salts comprising pharmacologically acceptable anions including, but not limited to, acetate, benzenesulfonate, benzoate, bicarbonate, bitartrate, bromide, calcium edetate, camsylate, carbonate, chloride, bromide, iodide, citrate, dihydrochloride, edetate, edisylate, estolate, esylate, fumarate, gluceptate, gluconate, glutamate, glycollylarsanilate, hexylresorcinate, hydrabamine, hydroxynaphthoate, isethionate, lactate, lactobionate, malate, maleate, mandelate, mesylate, methylsulfate, muscate, napsylate, nitrate, panthothenate, phosphate/diphosphate, polygalacturonate, salicylate, stearate, succinate, sulfate, tannate, tartrate, teoclate, triethiodide, and pamoate. Compounds of the invention that include an amino group also can form pharmaceutically acceptable salts with various amino acids, in addition to the acids mentioned above. Compounds of the invention that are acidic in nature are capable of forming base salts with various pharmacologically acceptable cations. Non-limiting examples of such salts include alkali metal or alkaline earth metal salts and, particularly, calcium, magnesium, sodium, lithium, zinc, potassium, and iron salts.

"Stercoisomer" encompasses all enantiomerically/stereomerically pure and enantiomerically/stereomerically enriched compounds disclosed herein.

"Stereomerically pure" or "enantiomerically pure" means that a compound comprises one stereoisomer and is substantially free of its counter stereoisomer or enantiomer. For example, a compound is stereomerically or enantiomerically pure when the compound contains 80%, 90% or 95% or more of one stereoisomer and 20%, 10% or 5% or less of the counter stereoisomer. In some cases, a compound of the invention is considered optically active or stereomerically/enantiomerically pure (i.e., substantially the R-form or substantially the S-form) with respect to a chiral center when the compound is about 80% ee (enantiomeric excess) or greater, preferably, equal to or greater than 90% ee with respect to a particular chiral center and more preferably 95% ee with respect to a particular chiral center.

"Stereomerically enriched" or "enantiomerically enriched" encompasses racemic mixtures as well as other mixtures of stereoisomers of compounds of this invention (e.g., K/S=30/70, 35/65, 40/60, 45/55, 55/45, 60/40, 65/35 and 70/30).

"Hydrate" means a compound of the present invention or a salt thereof that further includes a stoichiometric or non-stoichiometric amount of water bound by non-covalent intermolecular forces.

"Solvate" means a solvate formed from the association of one or more solvent molecules to a compound of the present invention. The term "solvate" includes hydrates (e.g., monohydrate, dihydrate, trihydrate, tetrahydrate, and the like).

"Polymorph" means solid crystalline forms of a compound of the present invention or complex thereof. Different polymorphs of the same compound can exhibit different physical, chemical and/or spectroscopic properties.

DETAILED DESCRIPTION

Provided herein are methods of modulating membrane potential of a cell membrane comprising the steps of: (a) forming a synthetic anion channel in the cell membrane; and (b) shifting the membrane potential toward the equilibrium potential of the anion in the cell. In some embodiments, the methods further comprise a step of imposing an anion gradient across the cell membrane.

Also provided herein are methods of regulating a natural voltage-dependent ion channel in a cell membrane comprising the steps of: (a) forming a synthetic anion channel in the cell membrane; (b) shifting the membrane potential toward the equilibrium potential of the anion in the cell; and (c) regulating the natural voltage-dependent ion channel, wherein the self-assembling compound has formula (I) as defined herein. In some embodiments, the methods further comprise a step of imposing an anion gradient across the cell membrane. In other embodiments, the natural voltage-dependent ion channel is a voltage-dependent sodium channel, potassium channel or calcium channel. In further embodiments, the natural voltage-dependent ion channel is a voltage-dependent calcium channel.

Also provided herein are methods of regulating the intracellular calcium concentration of a cell comprising the steps of (a) forming a synthetic anion channel in the cell membrane; (b) shifting the membrane potential toward the equilibrium potential of the anion in the cell; (c) regulating a natural voltage-dependent calcium channel; and (d) regulating the intracellular calcium concentration of the cell.

Also provided herein are methods of regulating the tension of a muscle cell comprising the steps of (a) forming a synthetic anion channel in the cell membrane; (b) shifting the membrane potential toward the equilibrium potential of the anion in the cell; (c) regulating a natural voltage-dependent calcium channel; (d) regulating the intracellular calcium concentration of the cell; and (e) regulating the tension of the muscle cell.

Also provided herein are methods of regulating a vascular tone comprising the steps of (a) forming a synthetic anion channel in the membrane of a vascular smooth muscle cell; (b) shifting the membrane potential toward the equilibrium potential of the anion in the cell; (c) regulating a natural voltage-dependent calcium channel; (d) regulating the intracellular calcium concentration of the cell; (e) regulating the tension of the vascular smooth muscle cell; and (f) regulating the vascular tone.

In some embodiments, the cell used in the method disclosed herein is a muscle cell. In other embodiments, the cell is a smooth muscle cell. In further embodiments, the cell is a vascular smooth muscle cell. In still further embodiments, the natural voltage-dependent calcium channel is L-type calcium channel. In still further embodiments, the cell membrane comprises a lipid bilayer.

In some embodiments, the anion used in the method disclosed herein is fluoride, chloride, bromide, iodide, nitrate, nitrite, sulfate, bisulfate, carbonate, bicarbonate, phosphate, hydrogen phosphate, dihydrogen phosphate or acetate. In other embodiments, the anion is chloride. In further embodiments, the anion channel is a chloride channel. In still further embodiments, the anion gradient is a chloride gradient.

Any self-assembling compound that can form a synthetic anion channel can be used for the methods disclosed herein. In some embodiments, the synthetic anion channel is formed by a plurality of molecules of a self-assembling compound having formula (I).

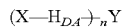  (I)

wherein X is an unsubstituted or substituted hydrocarbyl or heterocyclyl;

n is an integer from 1 to 6;

Y is a monovalent, divalent, trivalent, tetravalent, pentavalent or hexavalent linking group formed by removing one, two, three, four, five and six hydrogen atoms respectively from an unsubstituted or substituted hydrocarbon, carbocycle or heterocycle; and $H_{DA}$ is a divalent group having formula (II):

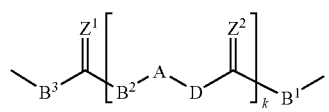  (II)

wherein each of $Z^1$ and $Z^2$ is independently O, S or $NR^1$;
each of A, $B^1$, $B^2$, $B^3$ and D is independently a bond, O, S, $NR^2$ or a substituted or unsubstituted $C_{1-10}$ alkylene; and k is an integer from 1 to 20, where each of $R^1$ and $R^2$ is independently H, acyl, hydrocarbyl, carbocyclyl or heterocyclyl and at least one of B1 and B2 of formula (II) is NH.

In some embodiments, each of A, $B^2$, and D of formula (II) is independently O, S, $NR^2$ or a substituted or unsubstituted $C_{1-10}$ alkylene; and each of $B^1$ and $B^3$ is independently a bond, O, S, $NR^2$ or a substituted or unsubstituted $C_{1-10}$ alkylene.

In some embodiments, $H_{DA}$ is a substituted hydrocarbylene comprising at least one hydrogen bond donor and at least one hydrogen bond acceptor. In further embodiments, the hydrogen bond donor comprises a hydrogen atom bonded directly to oxygen, nitrogen or sulfur. In further embodiments, the hydrogen bond acceptor is an oxygen, nitrogen, sulfur, fluorine, chlorine, or bromine atom. In certain embodiments, $H_{DA}$ of formula (I) comprises at least one primary amide or secondary amide group.

In certain embodiments, n of formula (I) is 1. In other embodiments, n of formula (I) is 2, and the two $X-H_{DA}$ units are either the same or different.

In some embodiments, X is a hydrocarbyl group such as alkyl, aryl, or aralkyl containing up to 18 carbon atoms, optionally substituted with an oxygen, nitrogen or sulfur containing moiety. In other embodiments, X is heterocyclo moiety optionally substituted with an oxygen, nitrogen or sulfur containing moiety. In one embodiment, $H_{DA}$ contains a diamide and X is a isobutyl group ($-CH_2CH(CH_3)_2$) linked to $H_{DA}$ unit through a nitrogen atom, forming a terminal isobutylamide. In other embodiments, X of formula (I) is hydrocarbyl or substituted hydrocarbyl. In certain embodiments, X of formula (I) is hydrocarbyl or substituted hydrocarbyl comprising 1 to 14 carbon atoms. In further embodiments, X of formula (I) is alkyl or substituted alkyl having 1 to 14 carbon atoms. In further embodiments, X of formula (I) is isobutyl.

In certain embodiments, Y of formula (I) is a divalent or trivalent linking group formed by removing two or three hydrogen atoms respectively from an unsubstituted or substituted alkane, alkene or alkyne. In further embodiments, Y is a divalent or trivalent linking group formed by removing two or three hydrogen atoms respectively from an unsubstituted or substituted $C_{2-12}$ alkane, alkene or alkyne. In still further embodiments, Y is unsubstituted or substituted propylene or propenylene.

In some embodiments, Y of formula (I) is a divalent or trivalent linking group formed by removing two or three hydrogen atoms respectively from an unsubstituted or substituted monocyclic, bicyclic or tricyclic aromatic carbocycle. In further embodiments, the aromatic carbocycle is an unsubstituted or substituted benzene. In further embodiments, Y is a divalent or trivalent linking group formed by removing two or three hydrogen atoms respectively from unsubstituted benzene.

In some embodiments, Y of formula (I) is a divalent or trivalent linking group formed by removing two or three hydrogen atoms respectively from an unsubstituted or substituted monocyclic, bicyclic or tricyclic heterocycle. In further embodiments, the heterocycle is an unsubstituted or substituted pyridine. In further embodiments, Y is pyridylene.

In certain embodiments, Y of formula (I) is arylene or heteroarylene and each $H_{DA}$ is bonded to a ring atom of Y. In some embodiments, Y of formula (I) is monocyclic, bicyclic or tricyclic arylene. In other embodiments, Y of formula (I) is arylene or heteroarylene having only one 5-, 6-, or 7-membered ring; and each $H_{DA}$ is bonded to a ring atom of Y. In certain embodiments, Y of formula (I) is phenylene, pyridylene, substituted phenylene or substituted pyridylene.

In further embodiments, Y is arylene or heteroarylene; each $H_{DA}$ is bonded to a ring atom of Y; and each X is an unsubstituted or substituted hydrocarbyl having 1 to 14 carbon atoms.

In certain embodiments, $H_{DA}$ may be selected from a variety of organic units containing both hydrogen bond donors and hydrogen bond acceptors. For example, $H_{DA}$ may be substituted hydrocarbyl or heterocyclyl. Without being bound by any theory, it appears that the driving force for self-assembly of compounds to form an ion channel is contributed primarily by a large number of well-defined intermolecularly hydrogen-bonding interactions, which are favoured in the low-dielectric-constant medium of lipid bilayers. In certain embodiments, $H_{DA}$ will be substituted hydrocarbyl, having lower alkyl ether, ester, thioester, amide, hydroxyl, thiol, amino, azo, or halo substituents or other hydrogen bond donors and hydrogen bond acceptors. In one embodiment, for example, $H_{DA}$ contains two amide bonds, such as carboxamide bonds. In another embodiment, $H_{DA}$ is a peptide.

In other embodiments, the self-assembling efficiency of the compounds to form an ion channel may be enhanced when Y links the same or different $X-H_{DA}$ units together, allowing higher possibility for the formation of three-dimensionally intermolecular hydrogen bonding network. In these embodiments, the unit, Y, is in certain embodiments rigid enough to hold the $X-H_{DA}$ units at certain directions in which the compounds may self-assemble more effectively. Y units satisfying these design considerations may be selected from a variety of organic units. In general, these units are carbocyclic or heterocyclic. Non-cyclic Y units are also contemplated. For example, Y may be a 5- or 6-membered ring comprising carbon and optionally a nitrogen, oxygen, or sulfur ring atom wherein the X—H$_{DA}$ units are covalently linked to ring atoms. In one embodiment, Y is a phenylene ring.

The compounds provided herein may be made by one skilled in organic synthesis by known techniques as well as by the general synthetic procedures disclosed herein. The design, synthesis, and characterization of the compounds are described in detail in Examples. In one embodiment, for example, H$_{DA}$ is a peptide and therefore it can be linked with X and Y units through amide bonds, respectively, by using standard peptide coupling methods.

In other embodiments, H$_{DA}$ of formula (I) is represented by formula (III):

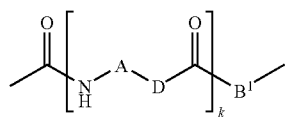

(III)

wherein k is 1 or 2;
A is O, S, NR$^2$ or a substituted or unsubstituted C$_{1-10}$ alkylene where R$^2$ is H, acyl, hydrocarbyl, carbocyclyl or heterocyclyl;
B$^1$ is O or NH; and
D is C$_{1-3}$ alkylene or C$_{1-3}$ alkylene substituted with one or more hydrocarbyl or heterocyclyl.

In other embodiments, H$_{DA}$ of formula (I) is represented by formula (IIIA):

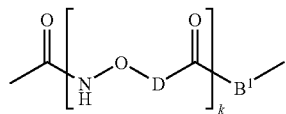

(IIIA)

wherein k is or 2;
B$^1$ is O or NH; and
D is C$_{1-3}$ alkylene or C$_{1-3}$ alkylene substituted with one or more hydrocarbyl or heterocyclyl.

In other embodiments, H$_{DA}$ of formula (I) is represented by formula (IIIB):

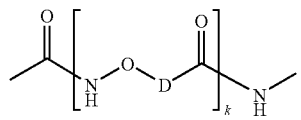

(IIIB)

wherein k is 1 or 2;
D is C$_{1-3}$ alkylene or C$_{1-3}$ alkylene substituted with one or more hydrocarbyl or heterocyclyl.

In other embodiments, H$_{DA}$ of formula (I) is represented by formula (IIIC):

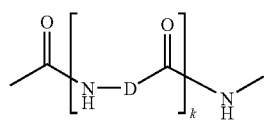

(IIIC)

wherein k is 1 or 2;

D is C$_{1-3}$ alkylene or C$_{1-3}$ alkylene substituted with one or more hydrocarbyl or heterocyclyl.

In other embodiments, H$_{DA}$ of formula (I) is represented by formula (IIID):

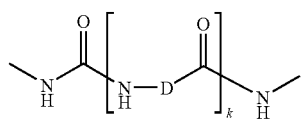

(IIID)

wherein k is 1 or 2;
D is C$_{1-3}$ alkylene or C$_{1-3}$ alkylene substituted with one or more hydrocarbyl or heterocyclyl.

In other embodiments, H$_{DA}$ of formula (I) is represented by formula (IIIE):

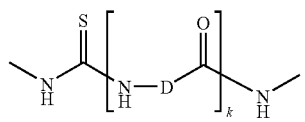

(IIIE)

wherein k is 1 or 2;
D is C$_{1-3}$ alkylene or C$_{1-3}$ alkylene substituted with one or more hydrocarbyl or heterocyclyl.

In certain embodiments, H$_{DA}$ of formula (I) is represented by formula (IV):

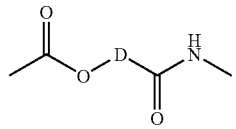

(IV)

wherein D is C$_{1-3}$ alkylene or C$_{1-3}$ alkylene substituted with one or more hydrocarbyl or heterocyclyl.

In other embodiments, H$_{DA}$ of formula (I) is represented by formula (IVB):

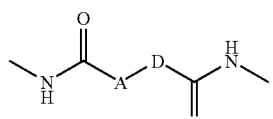

(IVB)

A is O, S, NR$^2$ or a substituted or unsubstituted C$_{1-10}$ alkylene where R$^2$ is H, acyl, hydrocarbyl, carbocyclyl or heterocyclyl; and
D is C$_{1-3}$ alkylene or C$_{1-3}$ alkylene substituted with one or more hydrocarbyl or heterocyclyl.

In certain embodiments, D of formula (III), (IIIA), (IIIB), (IIIC), (IIID), (IIIE) or (IV) is C$_{1-3}$ alkylene substituted with at least an alkyl, aryl, substituted alkyl or substituted aryl group. In certain embodiments, k of formula (III), (IIIA), (IIIB), (IIIC), (IIID), (IIIE), (IV) or (IVB) is 1. In further embodiments, D of formula (III), (IIIA), (IIIB), (IIIC), (IIID), (IIIE) or (IV) is C$_{1-3}$ alkylene substituted with at least an isobutyl group. In further embodiments, A of formula (III) is a bond; D is methylene or substituted methylene; and k is 1. In further embodiments, A of formula (III) is O; D is methylene or substituted methylene; and k is 1.

In other embodiments, D of formula (III), (IIIA), (IIIB), (IIIC), (IIID), (IIIE) or (IV) is one of the following formulae:

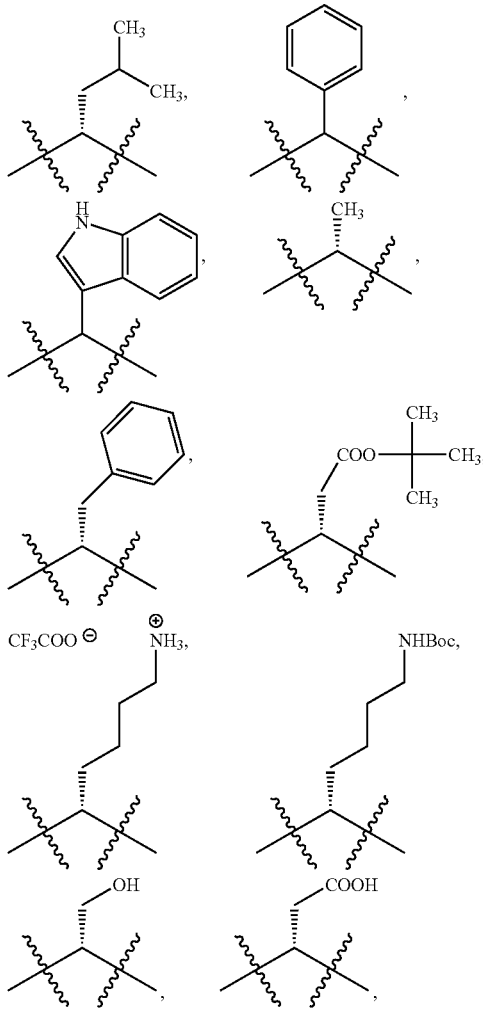

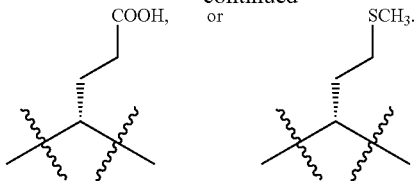

In some embodiments, the self-assembling compound has one of the following formulae:

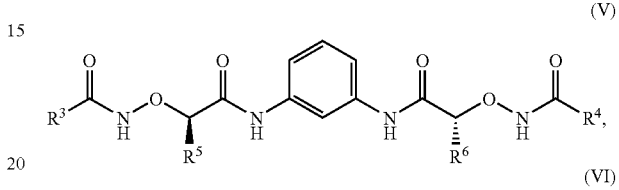
(V)

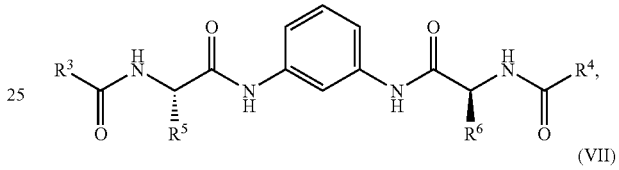
(VI)

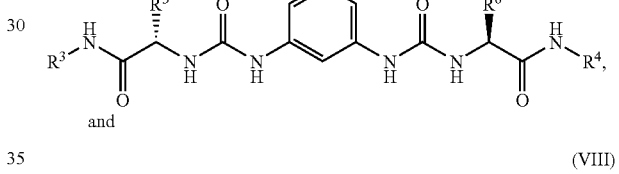
(VII)

and

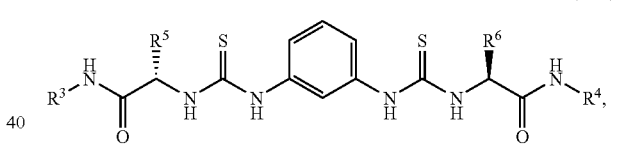
(VIII)

wherein each of $R^3$, $R^4$, $R^5$ and $R^6$ is independently H, acyl, hydrocarbyl, carbocyclyl or heterocyclyl.

In certain embodiments, the self-assembling compound is one of the following compounds:

Example 1

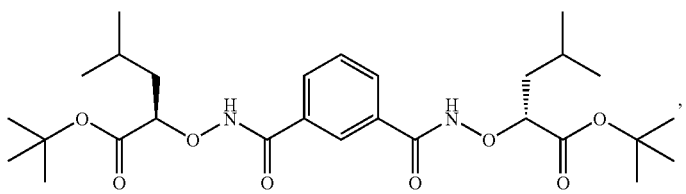

Example 2

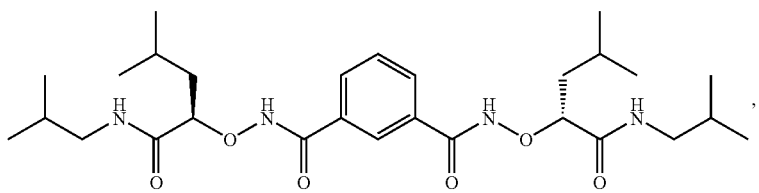

-continued
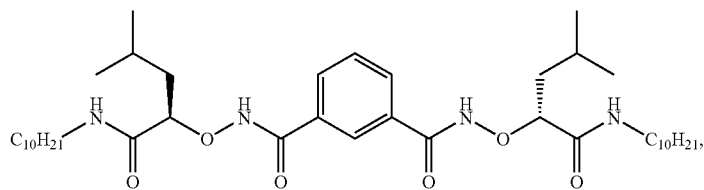
Example 3
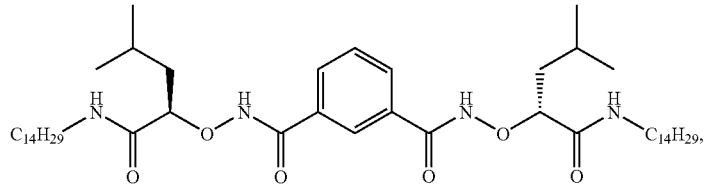
Example 4
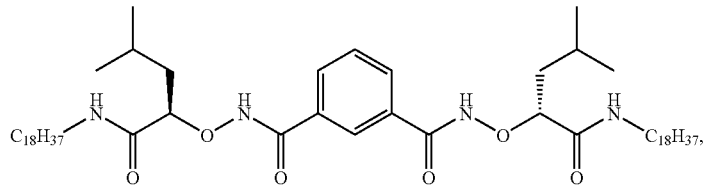
Example 5
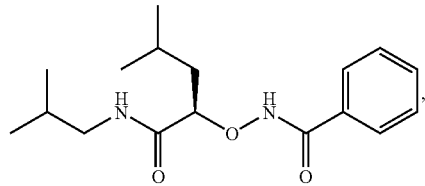
Example 6
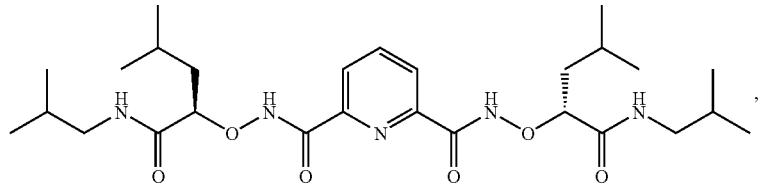
Example 7
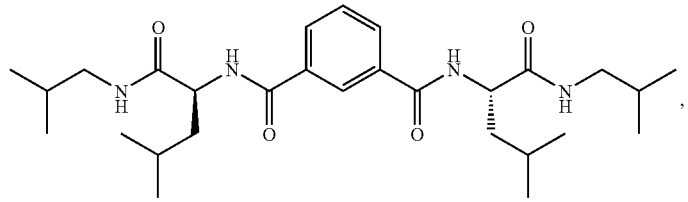
Example 8
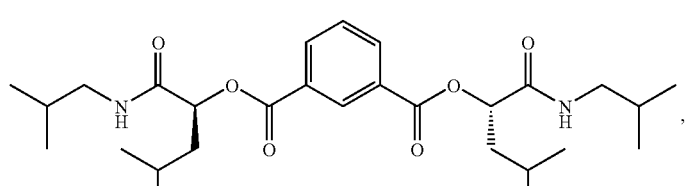
Example 9
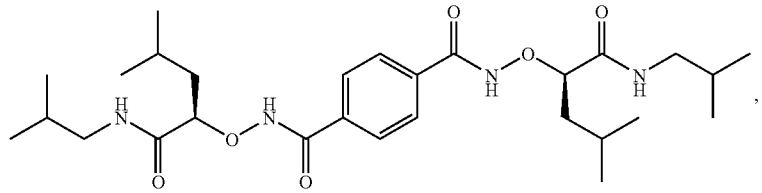
Example 10

-continued
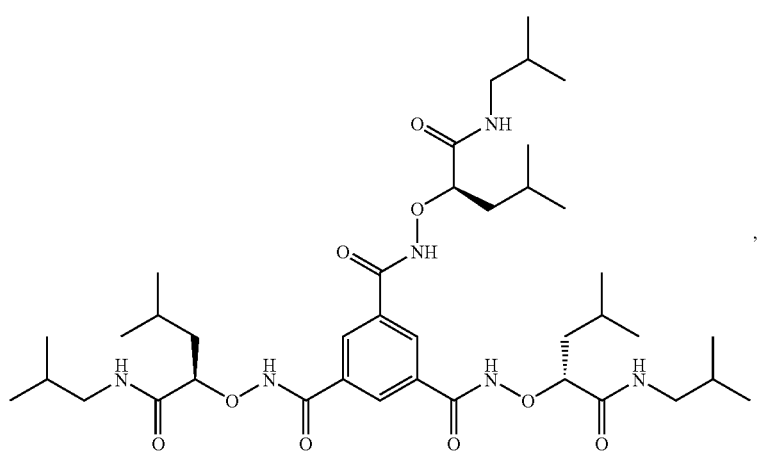
Example 11
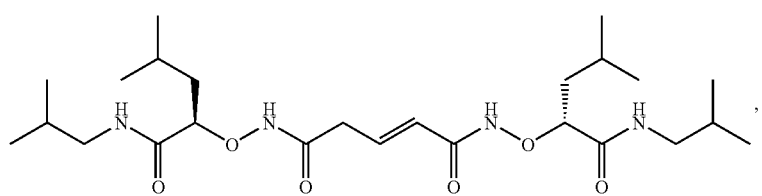
Example 12
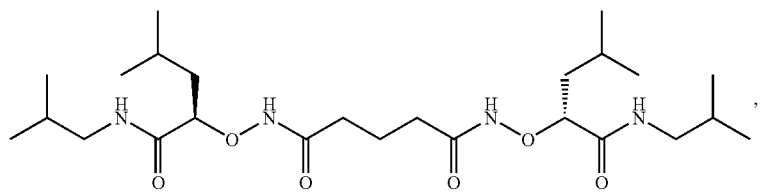
Example 13
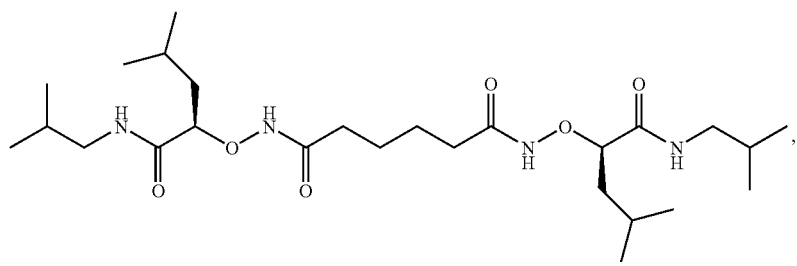
Example 14
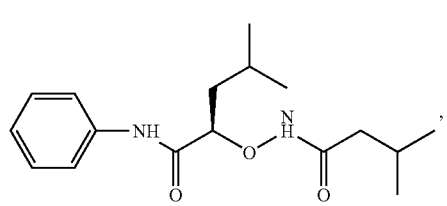
Example 15
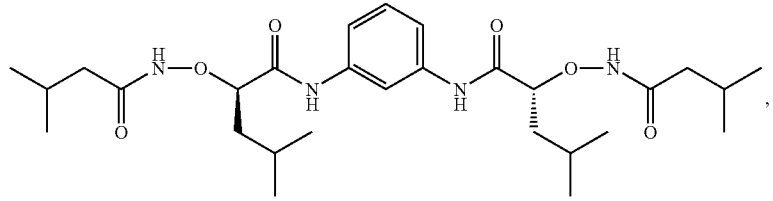
Example 16

Example 17
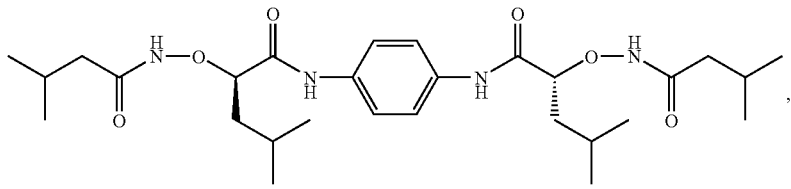
Example 18
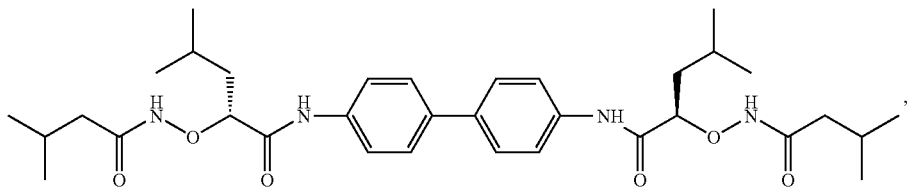
Example 19
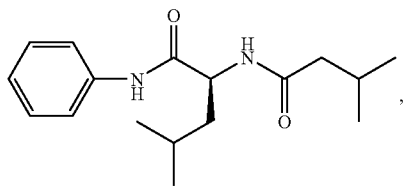
Example 20
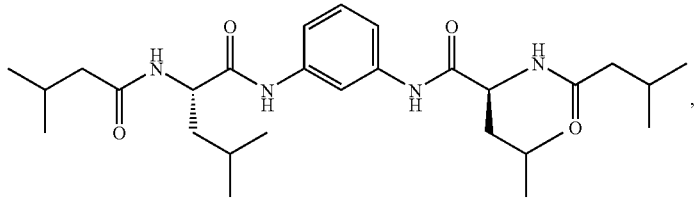
Example 21
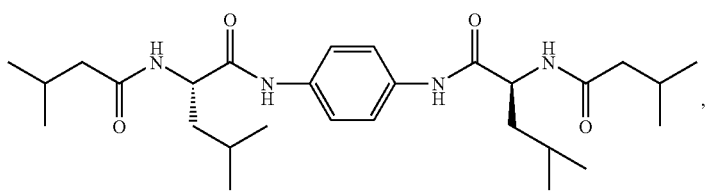
Example 22
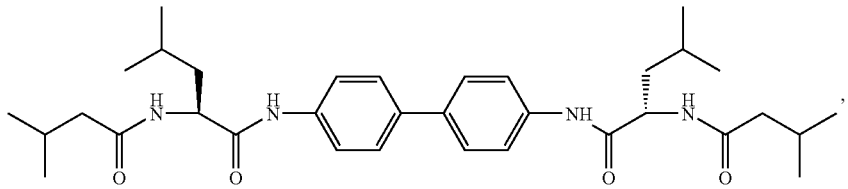
Example 23
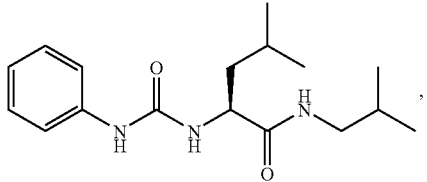
Example 24
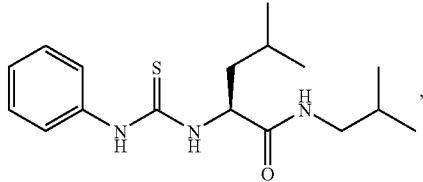
Example 25
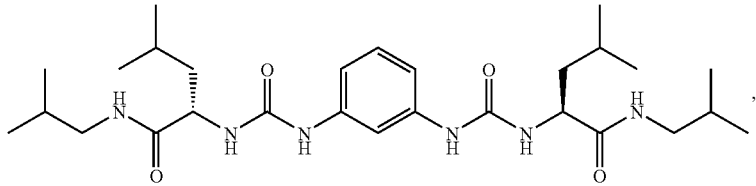

-continued
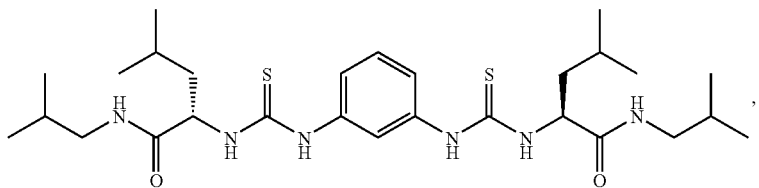
Example 26
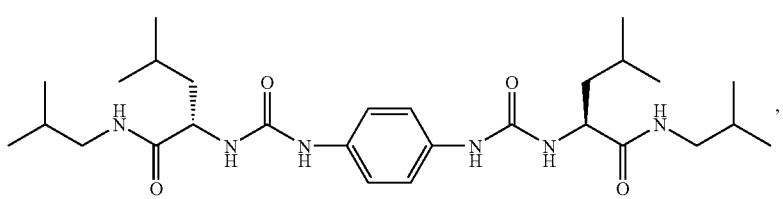
Example 27
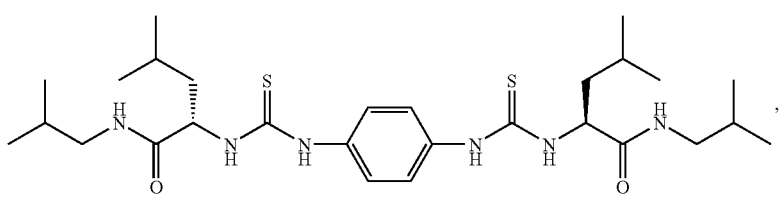
Example 28
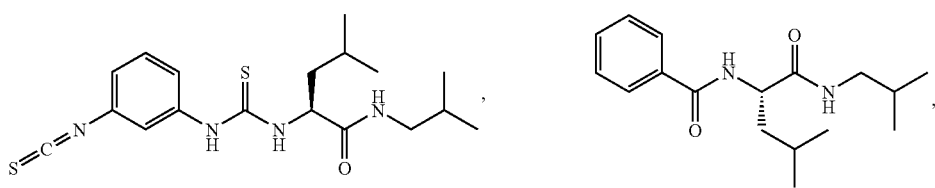
Example 29 Example 30
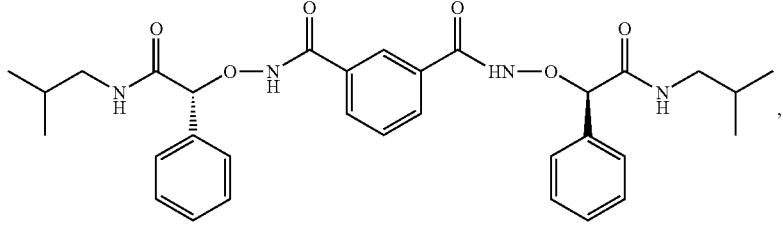
Example 31
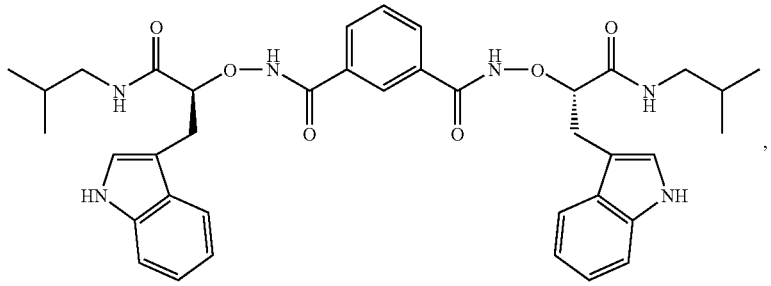
Example 32
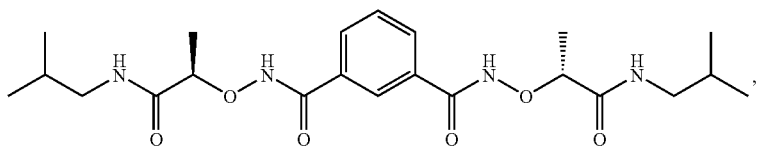
Example 33

-continued
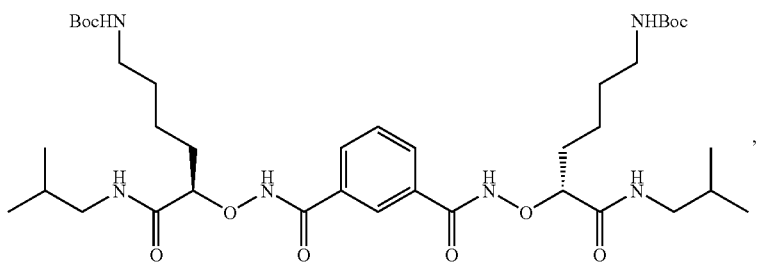
Example 34
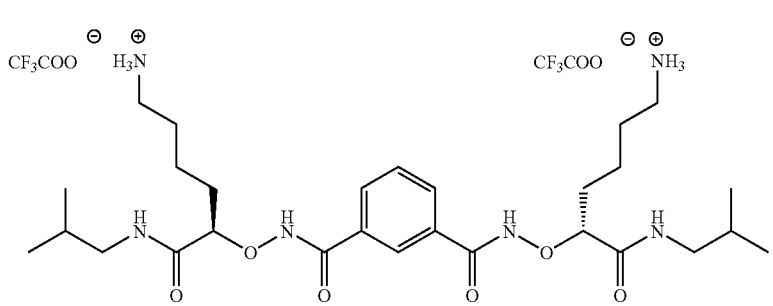
Example 35
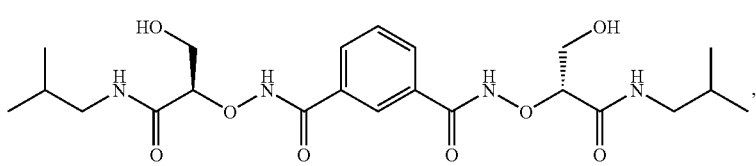
Example 36
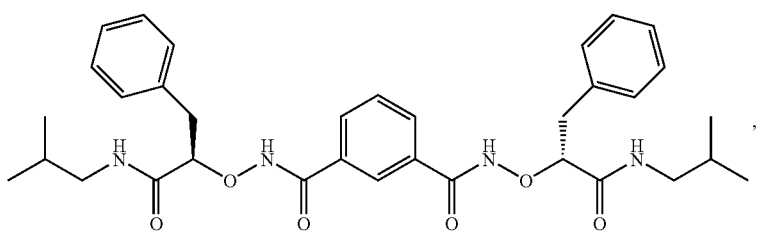
Example 37
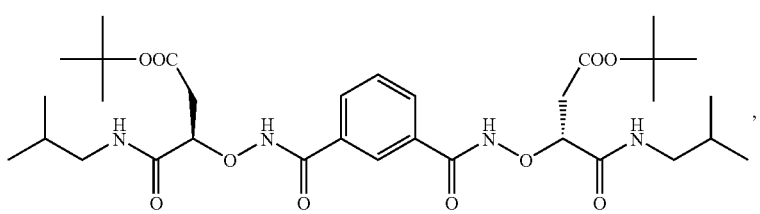
Example 38
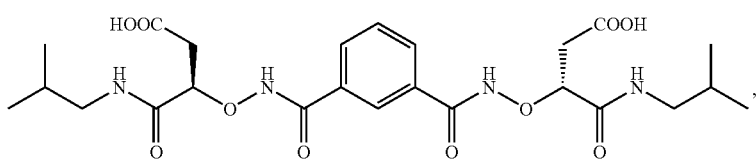
Example 39
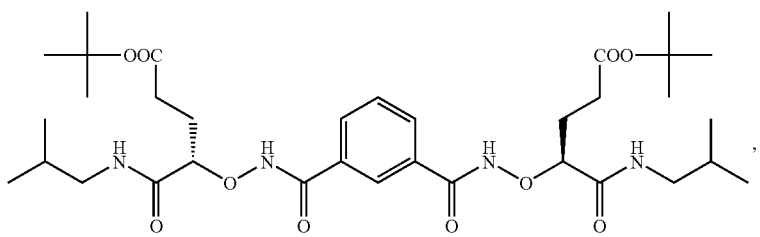
Example 40

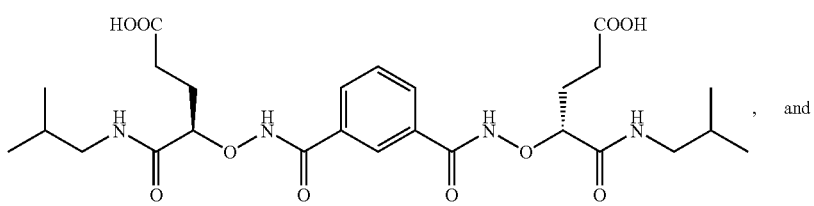

Example 41

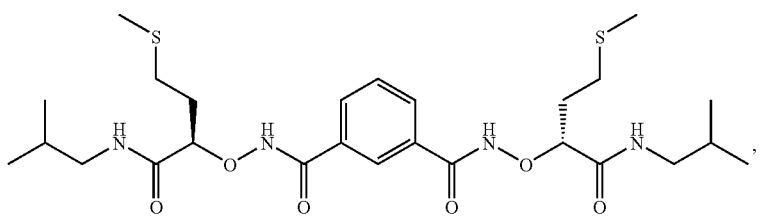

Example 42 or a salt, solvate, polymorph or stereoisomer thereof.

Synthetic ion channels can be prepared by constructing pore-like structures across the cell membranes. Synthetic ion channels can be classified based on their structures or "designs." Referring to FIG. 1, the simplest design of synthetic ion channels comprises a macromolecule of about 25-40 Å in length having a "unimolecular" pore-like structure. Other design strategies for preparing supramolecular assembly ion channels include the self-assembly of linear, stave-like monomers into a "barrel-stave" pore-like structure; and the stacking of macrocyclic, hoop-like monomers into a "barrel-hoop" pore-like structure. Some smaller macromolecules may self-assemble into a complex barrel-rosette' pore-like structure which can be conceivable either as the "barrel-stave" pore-like structure with fragmented staves or "barrel-hoop" pore-like structure with fragmented hoops.

Figure 2:
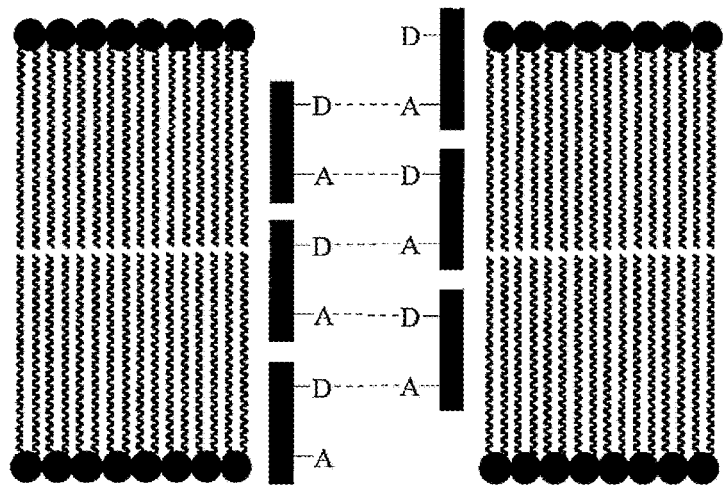
FIG. 2 depicts a synthetic ion channel across a lipid bilayer where the dashed lines represent hydrogen bonds and the thick solid lines represent self-assembling molecules, each of which comprises at least a hydrogen bond donor (represented by D) and at least a hydrogen bond acceptor (represented by A).
Figure 3:
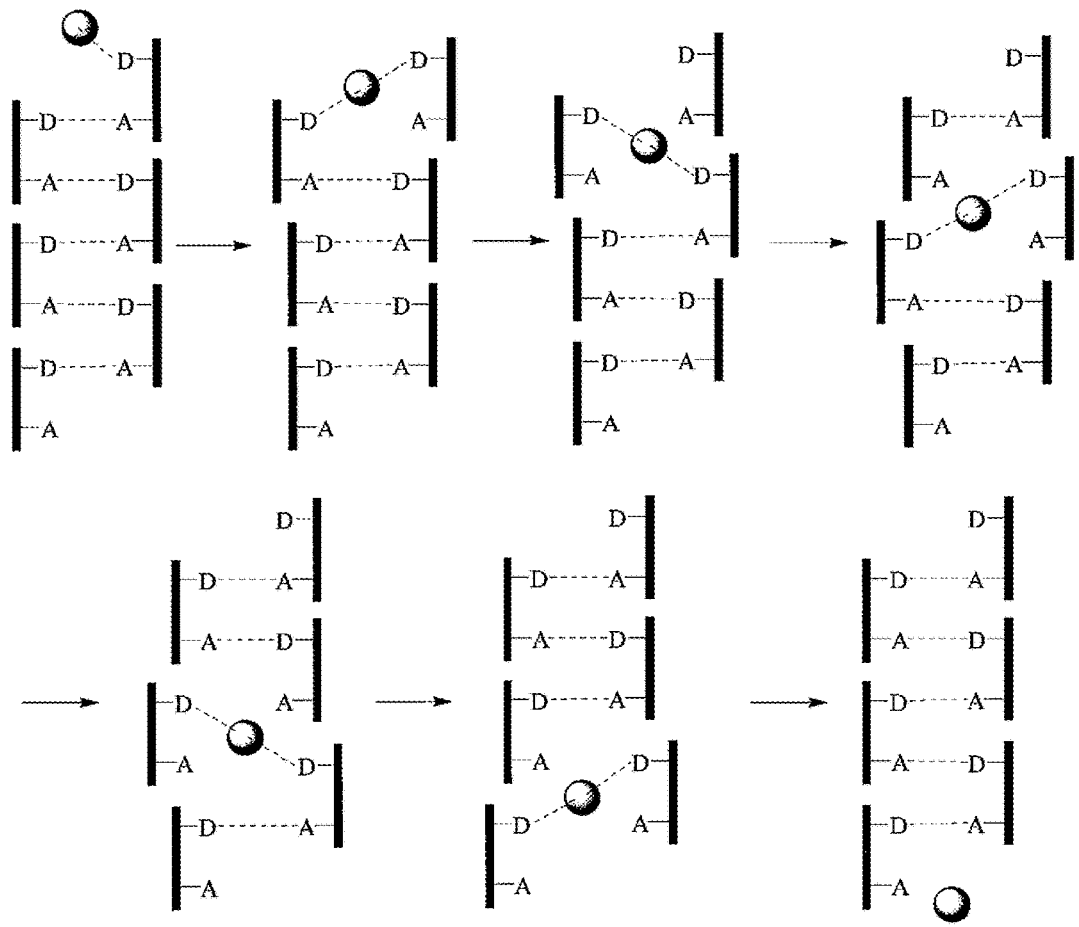
FIG. 3 depicts a possible anion transport process in the synthetic ion channel of FIG. 2 where the sphere represents an anion, the dashed lines represent hydrogen bonds and the thick solid lines represent self-assembling molecules, each of which comprises at least a hydrogen bond donor (represented by D) and at least a hydrogen bond acceptor (represented by A). The anion forms a hydrogen bond individually and sequentially with each of the hydrogen bond donors along the synthetic ion channel when it passes through the channel.
Figure 4:
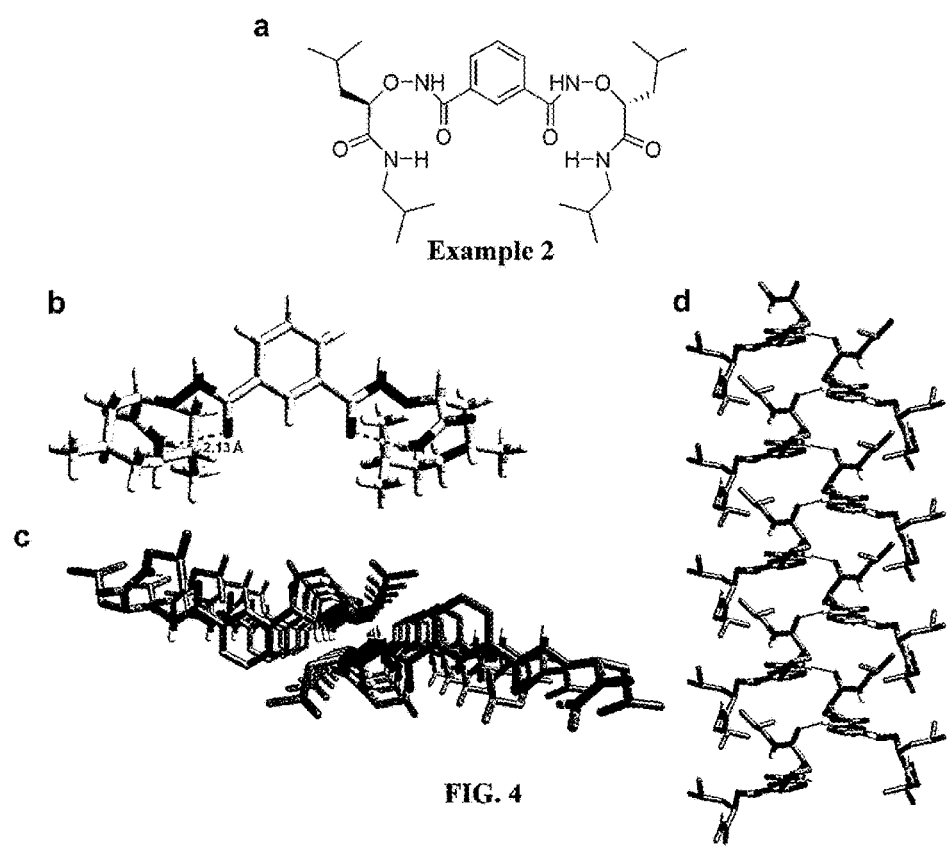
FIG. 4a-d depict various chemical representations Example 2.

Up to now, all of the synthetic ion channels are designed as pore-like structures through which ions transport across the membranes. Provided herein is a new strategy for the is design of self-assembling compounds, the molecules of which can self-assemble into ion channels. In some embodiments, the designed molecules can self-assemble through non-covalent interactions to form molecular columns in the transverse direction of lipid membranes. In one embodiment, between two parallel molecular columns, there are intermolecular hydrogen bonds in the lateral direction of the lipid membranes as shown in FIG. 2. When an anion or cation reaches membranes, these intermolecular hydrogen bonds can be reorganized. The donors or acceptors of the original intermolecular hydrogen bonds will afford successive binding sites for stabilization of the anion or the cation, respectively, when they transport across hydrophobic regions of lipid membranes as shown in FIG. 3. In one embodiment, the designed self-assembling compound shows its self-assembled structure in the solid state as shown in FIG. 4b-d having channels that can be used as chloride ion channels.

Without being bound by any theory, although the detailed mechanism is not yet known clearly, the self-assembling compounds disclosed herein have ability to partition into a lipid bilayer and therein self-assemble into an ion channel. These compounds are thought to assemble through well-defined intermolecularly hydrogen-bonding interactions, which are favored in the low-dielectric-constant medium of lipid bilayers. Such a hydrogen bonding induced assembly of compounds with a relatively lipophilic surface, which allows for stable integration and self-assembly in the non-polar environment of lipid bilayers, may penetrate the hydrophobic region of lipid bilayer membranes to form an ion channel.

Physiologically active anions, such as chloride ions, are involved in a number of biological processes. In nature, the transport of chloride ions through cell membranes is regulated by neutral anion binding proteins (chloride ion channels). The self-assembling compounds disclosed herein may partition into lipid bilayers of biological and synthetic cell membranes and function as synthetic ion channels. For example, the compound disclosed in Example 2 can be used to prepare such a synthetic chloride channel. Example 2 can insert into lipid bilayers of liposomes and self-assemble to form a 54 pS (pico-Siemens) chloride channel which shows chloride selectivity and voltage dependent gating. The compound of Example 2 can also efficiently form chloride channels in the membranes of human embryonic kidney (HEK 293) cells and thereby dramatically increases cell chloride currents at a remarkably low concentration of 50 nM (nano-molar). The ion channel behavior of the compound of Example 2 demonstrates that the synthetic ion channel structures disclosed herein can afford selective membrane permeability equivalent in many respects to that observed in natural protein channels.

The self-assembling compounds disclosed herein may modulate the concentration of a target anion to allow study on the behavior of physiological systems or models thereof. Alternatively, anion concentration may be varied or regulated by application of the self-assembling compounds in therapeutic systems, to increase or decrease anion concentrations in order to counteract or otherwise modify diseased or unwanted conditions. Accordingly, the self-assembling compounds disclosed herein may be used to modulate the influx or efflux of anions, including, but not limited to halides such as chloride and bromide, or other anions such as nitrate and bicarbonate, into a mammalian cell or other membrane systems, such as, mitochondria, endosomes, lysosomes, secretory vesicles, endoplasmic reticula, nucleii, Golgi apparatus, intracellular transport vesicles, MHC processing vesicles, reconstituted ruffled membrane vesicles from osteoclasts, and others having a lipid bilayer membrane.

In biological and synthetic systems, the composition of a cell membrane varies depending upon its location in a biological system and its desired function in synthetic systems. Therefore, provided is the formation of synthetic ion channels in a membrane irrespective of whether the membrane is of natural or synthetic origin. In certain embodiments, the self-assembling compounds disclosed herein have the ability to self-assemble through hydrogen bonds in physiological and non-physiological systems and form anion channels in lipid bilayers or cell membranes.

Also provided is a method of treating, preventing, managing or ameliorating symptoms of a disease or condition associated with abnormal membrane potential responses using the self-assembling compounds and compositions provided herein. Non-limiting examples of such a disease or condition include hypertension, autosomal-dominant long-QT syndrome with deafness, autosomal-reccessive long-QT syndrome, benign familial neonatal convulsions, Long-QT syndrome, Long-QT syndrome with dysmorphic features, generalised epilepsy with febrile seizures (GEFS+), generalised epilepsy with febrile and afebrile seizures, paramyotonia congenita, potassium-aggravated myotonia hyperkalaemic periodic paralysis and Brugada syndrome. In some embodiments, the self-assembling compounds disclosed herein are inserted into the lipid bilayer of a mammalian cell in an appropriate amount, and manner, as determined by characteristics of the particular compound, patient profile, and disease in question.

In certain embodiments, the compounds and compositions may be applied in vivo, to tissues such as the lungs, trachea, skin, muscle, brain, liver, heart, spleen, bone marrow, thymus, bladder, lymph, blood, pancreas, stomach, kidney, ovaries, testicles, rectum, peripheral or central nervous system, eyes, lymphoid organs, cartilage and endothelium. In certain embodiments, the target cell is a muscle cell (such as a skeleton muscle cell, a cardiac muscle cell and a smooth muscle cell), a nerve cell, a hematopoietic stem cell, a neuron cell, an epithelium cell or alternatively a cell of the airways. In other embodiments, the target cell is a tracheal or pulmonary cell. In further embodiments, the target cell is a cell of the respiratory epithelium.

The self-assembling compounds disclosed herein can be used as a medicament for curative or preventive purpose. Specifically, the self-assembling compounds may be used in a method of therapeutic treatment that consists of introducing the compound into the lipid bilayer of target cells which are engaged in ion transport. As such, the compounds may be used in the preparation of a medicament for curative or preventive purposes, intended for the treatment of the human or animal body.

The medicament may be administered directly in vivo, for example, into a muscle by infusion, into the lungs by aerosol and the like. It is also possible to adopt an ex vivo approach, which consists of collecting cells from the patient (bone marrow stem cells, peripheral blood lymphocytes, muscle cells, nerve cells, neuron cells, epithelial cells and the like), administering the compounds and re-administering the cells to the patient.

The self-assembling compounds provided herein may be administered by the intramuscular, intratracheal, intranasal, intracerebral, intrapleural, intratumoral, intracardiac, intragastric, intraperitoneal, epidermal, intravenous or intraarterial route by a syringe or by any other equivalent means, systems suitable for the treatment of the airways or of the mucous membranes such as inhalation, instillation or aerosolization. Other routes of administration include application of a cream, oral administration or any other means known to the person skilled in the art and applicable to the compounds and compositions provided herein.

Administration may be achieved by a variety of different routes. One route is oral administration of a composition such as a pill, capsule or suspension. Such composition may be prepared according to any method known in the art, and may comprise any of a variety of inactive ingredients. Suitable excipients for use within such compositions include insert diluents (which may be solid materials, aqueous solutions and/or oils) such as calcium, potassium, or sodium carbonate, lactose, calcium, potassium, or sodium phosphate, water, arachis oil, peanut oil, liquid paraffin or olive oil; granulating and disintegrating agents such as maize starch, gelatin or acacia and/or lubricating agents such as magnesium stearate, stearic acid, or talc. Other inactive ingredients that may, but need not, be present include one or more suspending agents (e.g., sodium carboxymethylcellulose, methylcellulose, hydroxypropylmethylcellulose, sodium alginate, polyvinylpyrrolidone, gum tragacanth, and gum acacia), thickeners (e.g., beeswax, paraffin or cetyl alcohol), dispersing or wetting agents, preservatives (e.g., antioxidants such as ascorbic acid), coloring agents, sweetening agents and/or flavoring agents.

A pharmaceutical composition may be prepared with carriers that protect active ingredients against rapid elimination from the body, such as time release formulations or coatings. Such carriers include controlled release formulations, such as, but not limited to, microencapsulated delivery systems, and biodegradable, biocompatible polymers, such as ethylene vinyl acetate, polyanhydrides, polyglycolic acid, polyorthoesters, polylactic acid, polyethylene glycols, polyethylene glycol ethers, and others known to those of ordinary skill in the art.

In other embodiments, provided are methods in which the compounds are directly administered as a pressurized aerosol or nebulized formulation to the patient's lungs via inhalation. Such formulations may contain any of a variety of known aerosol propellants useful for endopulmonary and/or intranasal inhalation administration. In addition, water may be present, with or without any of co-solvents, surfactants, stabilizers (e.g., antioxidants, chelating agents, insert gases and buffers). For compositions to be administered from multiple dose containers, antimicrobial agents are typically added. Such compositions may also be filtered and sterilized, and may be lyophilized to provide enhanced stability and to improve solubility.

Pharmaceutical compositions can be administered in an amount, and with a frequency, that is effective to inhibit or alleviate the symptoms of a disease or condition, such as cystic fibrosis, and/or delay the progression of the disease. The precise dosage and duration of treatment may be determined empirically using known testing protocols or by testing the composition in model systems known in the art and extrapolating therefrom. Dosages may also vary with the severity of the disease. A pharmaceutical composition may be formulated and administered to exert a therapeutically useful effect while minimizing undesirable side effects. It will be apparent that, for any particular subject, specific dosage regimens may be adjusted over time according to the individual need.

As noted above, a pharmaceutical composition may be administered to a mammal to stimulate chloride transport, or to treat, manage or prevent cystic fibrosis, Bartter's syndrome, Dent's disease, inherited kidney stone disease, myotonia congenita, Becker syndrome, epilepsy, vitelliform macular dystrophy, hyperekplexia, juvenile myoclonus epilepsy or osteopetrose. Patients that may benefit from administration of a self-assembling compound provided herein are those afflicted with cystic fibrosis, Bartter's syndrome, Dent's disease, inherited kidney stone disease, myotonia congenita, Becker syndrome, epilepsy, vitelliform macular dystrophy, hyperekplexia, juvenile myoclonus epilepsy or osteopetrose. Such patients may be identified based on standard criteria that are well known in the art, including the presence of abnormally high salt concentrations in the sweat test, the presence of high nasal potentials, or the presence of a cystic fibrosis-associated mutation. Activation of chloride transport may also be beneficial in other diseases that show abnormally high mucus accumulation in the airways, such as asthma and chronic bronchitis. Similarly, intestinal constipation may benefit from activation of chloride transport as provided herein.

Also provided are methods of administering the pharmaceutical compositions by intravenous, oral, instillation, inhalation, topical, intraperitoneal, subcutaneous, or intramuscular routes. The pharmaceutical compositions may be administered, for example, in the form of capsules, powders, tablets, liquids, solutions, and aerosolized solutions. Also provided are methods of treating diseases or other conditions in a mammal that give rise to defective anion transport across cell membranes.

Additional features and advantages of the invention will be set forth, and in part will be apparent from the description, or may be learned by practice of the invention.

Dosages of the compositions provided will vary, depending on factors such as half-life of the compound, potential adverse effects of the compound or of degradation products thereof, the route of administration, the condition of the patient, and the like. Such factors are capable of determination by those skilled in the art. The exact dose level given on a daily basis, of course, is meant to be adapted by a physician to provide the optimum therapeutic response.

EXAMPLES

The following Examples 1-42 are detailed descriptions of the methods of making and using the compounds represented by general formula (I). Other compounds with the scope of this disclosure may be prepared using the procedures with appropriate starting material which are apparent to those of skill in the art. These examples are presented for illustrative purposes only and are not intended to limit the scope of the invention.

Preparation of Example 1

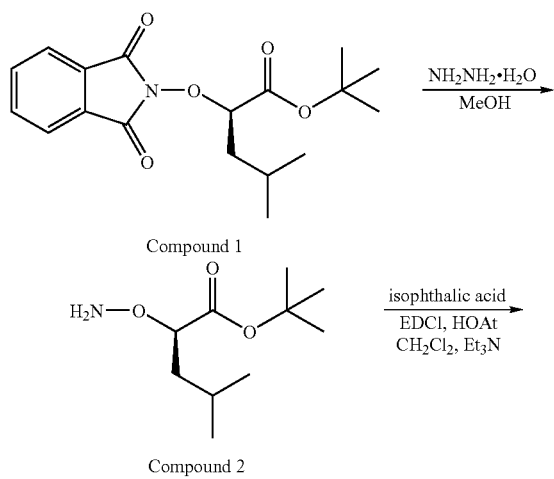

Compound 2

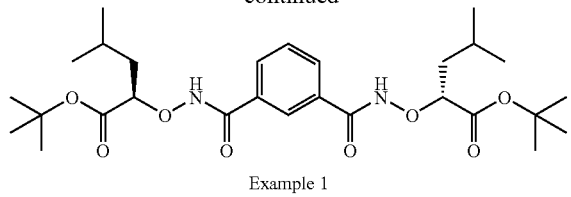

Example 1

Example 1 was prepared according to Scheme A above. The starting material, D-tert-butyl 2-phthalimidoxy-4-methylpentanoate (Compound 1), was synthesized according to the procedures described in Yang et al., *J. Org. Chem*, 2001, 66, 7303-7312. Compound 1, a white crystalline solid, was characterized by the following data: m.p. 92-93° C.; $[\alpha]^{20}_D$+77.0° (c 1.01, CHCl$_3$); $^1$H NMR (300 MHz, CDCl$_3$) δ 7.85-7.81 (m, 2H), 7.78-7.74 (m, 2H), 4.74 (dd, J=8.5, 5.4 Hz, 1H), 2.05-1.91 (m, 2H), 1.72-1.63 (m, 1H), 1.46 (s, 9H), 1.07 (d, J=6.3 Hz, 3H), 1.00 (d, J=6.3 Hz, 3H); $^{13}$C NMR (75 MHz, CDCl$_3$) δ 169.13, 163.21, 134.50, 128.87, 123.53, 84.74, 83.39, 39.89, 27.82, 24.47, 22.90, 21.96; IR (CHCl$_3$) 3032, 1793, 1738 cm$^{-1}$; LRMS (EI, 70 ev) m/z 333 (M$^+$, 1), 278 (6), 232 (17), 164 (15), 148 (100); HRMS (EI) for C$_{18}$H$_{23}$NO$_5$ (M$^+$): calculated 333.1576. found 333.1573.

To a solution of Compound 1 (2.00 g, 6.0 mmol) in CH$_3$OH (20 mL) was added NH$_2$NH$_2$.H$_2$O (900 mg, 18.0 mmol). A white precipitate appeared after 1 hour. After being stirred at room temperature for 2.5 hours, the reaction mixture was concentrated under vacuo. The residue was dissolved in CH$_2$Cl$_2$ and washed with 5% NaHCO$_3$ twice and ten with brine. The organic layer was dried over anhydrous Na$_2$SO$_4$ and concentrated to provide a mixture of the free amine (Compound 2) and phthahydroazide as a colorless oil. This mixture was immediately used in the peptide coupling reaction below without further purification.

Peptide Coupling Reaction.

Freshly distilled CH$_2$Cl$_2$ (80 mL) was added to a flask containing dried Compound 2 under nitrogen atmosphere, followed by the additions of 1-hydroxy-7-azabenzotriazole (HOAt, 2.11 g, 15.6 mmol), isophthalic acid (498 mg, 3.0 mmol), triethylamine (0.83 mL, 6.0 mmol), and finally 1-ethyl-3-(3-dimethylamino-propyl)-carbodiimide (EDCI, 5.35 g, 18.0 mmol). After stirred overnight, the reaction mixture was diluted with CH$_2$Cl$_2$. The organic layer was washed with 5% NaHCO$_3$ and brine, then dried over anhydrous MgSO$_4$ and concentrated. The crude oil was purified by flash column chromatography to afford 1.32 g (82% yield) of Example 1 as white solid. Example 1 was characterized by the following data: m.p. 57-59° C.; $[\alpha]^{20}_D$+78.1° (c 0.50, CHCl$_3$); $^1$H NMR (300 MHz, CDCl$_3$) δ 9.86 (br, 2H), 8.14 (t, J=1.5 Hz, 1H), 7.90 (dd, J=7.8, 1.5 Hz, 2H), 7.48 (t, J=7.8 Hz, 1H), 4.53 (dd, J=9.0, 4.2 Hz, 2H), 2.01-1.92 (m, 2H), 1.77-1.68 (m, 2H), 1.60-1.51 (m, 2H), 1.46 (s, 18H), 1.02 (d, J=6.5 Hz, 12H), 0.96 (d, J=6.5 Hz, 6H); $^{13}$C NMR (75 MHz, CDCl$_3$) δ 171.80, 164.58, 132.18, 130.41, 128.91, 125.58, 82.37, 82.17, 39.86, 27.97, 24.60, 23.18, 23.01, 21.79; IR (CHCl$_3$) 3403, 3019, 1730, 1688 cm$^{-1}$; LRMS (EI, 20 eV) m/z 536 (M$^+$); HRMS (EI, 20 eV) for C$_{28}$H$_{44}$N$_2$O$_8$ (M$^+$): calculated 536.3098. found 536.3078.

Preparation of Example 2

Scheme B

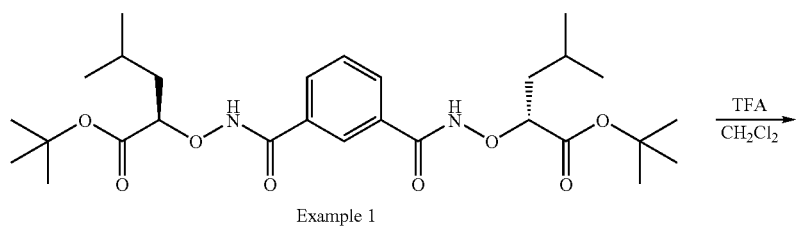

Example 1

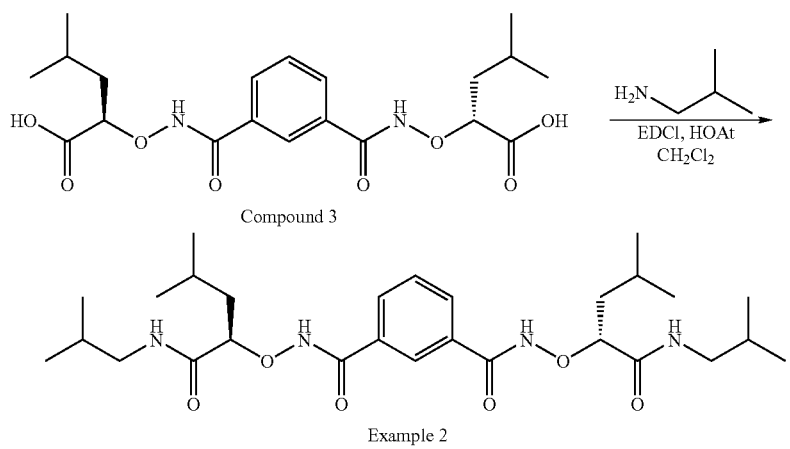

Example 2 was prepared according to Scheme B above. To the solution of Example 1 (537 mg, 1.0 mmol) in CH$_2$Cl$_2$ (5 mL) was carefully added an equal volume of CF$_3$COOH (5 mL) through a syringe at room temperature. After being stirred at room temperature for 3 hour, the reaction mixture was concentrated under vacuo. The residue was azeotroped with toluene twice to give free acid Compound 3 as a white solid and the white solid was used directly in the peptide coupling.

Freshly distilled CH$_2$Cl$_2$ (50 mL) was added to a flask containing dried free acid Compound 3 under nitrogen atmosphere, followed by the addition of HOAt (354 mg, 2.6 mmol), isobutylamine (0.21 mL, 2.1 mmol, and finally EDCI (891 mg, 3.0 mmol). After stirred overnight, the reaction mixture was diluted with CH$_2$Cl$_2$. The organic layer was washed with 5% NaHCO$_3$ and brine, then dried over anhydrous MgSO$_4$ and concentrated. The crude oil was purified by flash column chromatography to afford 492 mg of Example 2 (92% yield) as a white solid. Example 2 was characterized by the following data: m.p. 176-178° C.; $[\alpha]^{20}{}_D$+67.3° (c 0.50, CHCl$_3$); $^1$H NMR (600 MHz, CDCl$_3$) δ 10.43 (s, 2H), 8.12 (s, 1H), 8.07 (t, J=5.7 Hz, 2H), 8.04 (d, J=7.8 Hz, 2H), 7.57 (t, J=7.8 Hz, 1H), 4.40 (dd, J=9.5, 3.4 Hz, 2H), 3.05-3.01 (m, 2H), 2.91-2.88 (m, 2H), 1.86-1.62 (m, 8H), 0.92 (d, J=6.6 Hz, 12H), 0.84 (d, J=6.7 Hz, 6H), 0.78 (d, J=6.7 Hz, 6H); $^{13}$C NMR (75 MHz, CDCl$_3$) δ 171.89, 166.14, 131.97, 131.30, 129.69, 124.93, 85.60, 46.69, 41.15, 28.29, 24.85, 23.18, 21.81, 20.04, 19.99; IR (CHCl$_3$) 3332, 3185, 1663 cm$^{-1}$; LRMS (EI, 20 eV) m/z 534 (M$^+$); HRMS (EI, 20 eV) for C$_{28}$H$_{46}$N$_4$O$_6$ (M$^+$): calculated 534.3417. found 534.3435.

Preparation of Example 3

Scheme C

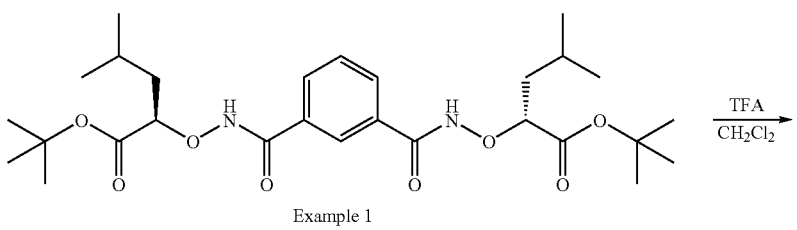

Example 1

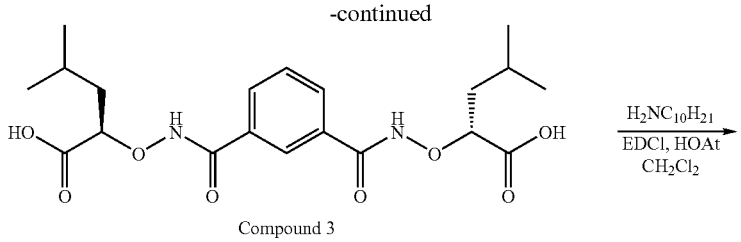

Compound 3

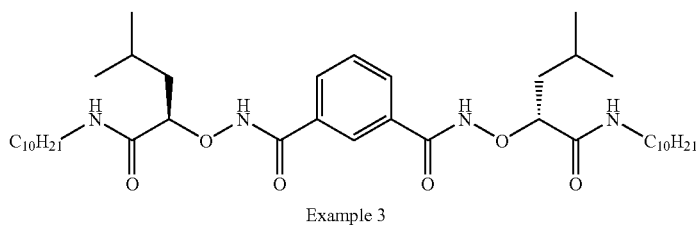

Example 3

Example 3 was prepared according to Scheme C above which was similar to Scheme B for Example 2 except that isobutylamine was replaced with decylamine. Example 3 was isolated as a colorless oil. Example 3 was characterized by the following data: $[\alpha]^{20}{}_D$ +34.5° (c 1.00, CHCl$_3$); $^1$H NMR (400 MHz, CDCl$_3$) δ 11.32 (s, 2H), 8.28 (br, 2H), 8.19 (s, 1H), 8.05 (d, J=7.5 Hz, 2H), 7.52 (t, J=7.5 Hz, 1H), 4.38 (br, 2H), 3.13-3.02 (m, 4H), 1.82 (m, 2H), 1.65-1.55 (m, 4H), 1.42 (br, 4H), 1.35-1.25 (m, 28H), 0.89-0.85 (m, 18H); $^{13}$C NMR (100 MHz, CDCl$_3$) δ 172.30, 165.91, 132.05, 131.29, 129.37, 124.98, 85.31, 41.17, 39.47, 31.89, 29.55, 29.53, 29.30, 29.12, 26.91, 24.73, 23.18, 22.67, 21.79, 14.10; IR (CHCl$_3$) 3446, 1662 cm$^{-1}$; LRMS (FAB) m/z 704 (M$^+$, 1); HRMS (FAB) for C$_{40}$H$_{71}$N$_4$O$_6$ (M$^+$, 1): calculated 703.5374. found 703.5354.

Preparation of Example 4

Scheme D

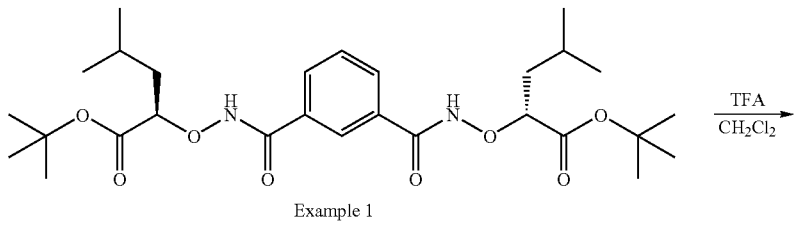

Example 1

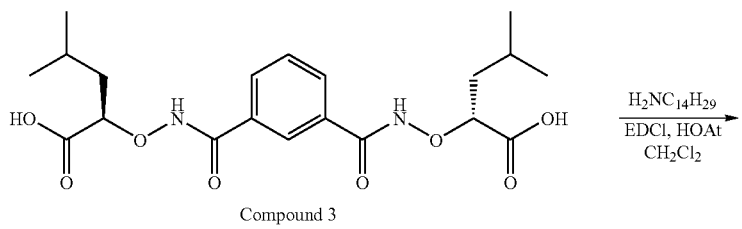

Compound 3

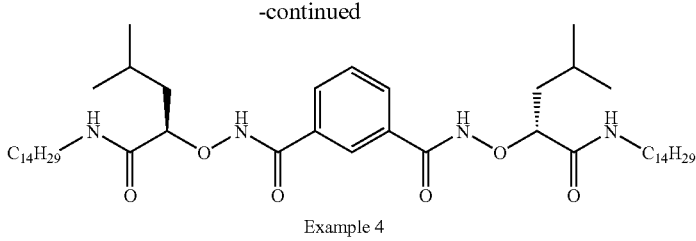

Example 4

Example 4 was prepared according to Scheme D above which was similar to Scheme B for Example 2 except that isobutylamine was replaced with tetradecylamine. Example 4 was isolated as a yellow oil. Example 4 was characterized by the following data: $[\alpha]^{20}_D$+52.2° (c 1.00, CHCl$_3$); $^1$H NMR (400 MHz, CDCl$_3$) δ 10.97 (s, 2H), 8.15 (br, 3H), 8.05 (d, J=7.8 Hz, 2H), 7.53 (t, J=7.8 Hz, 1H), 4.36 (dd, J=9.1, 3.7 Hz, 2H), 3.16-3.06 (m, 4H), 1.80 (m, 2H), 1.65-1.55 (m, 4H), 1.43 (br, 4H), 1.25-1.17 (m, 44H), 0.89-0.85 (m, 18H); $^{13}$C NMR (100 MHz, CDCl$_3$) δ 171.96, 165.92, 132.00, 131.26, 129.43, 124.93, 85.38, 41.07, 39.39, 31.89, 29.67, 29.64, 29.59, 29.53, 29.33, 29.27, 29.14, 26.89, 24.72, 23.12, 22.66, 21.77, 14.08; IR (CHCl$_3$) 3441, 3342, 1662 cm$^{-1}$; LRMS (FAB) m/z 816 (M$^+$, 1); HRMS (FAB) for C$_{48}$H$_{87}$N$_4$O$_6$ (M$^+$, 1): calculated 815.6626. found 815.6610.

Preparation of Example 5

Scheme E

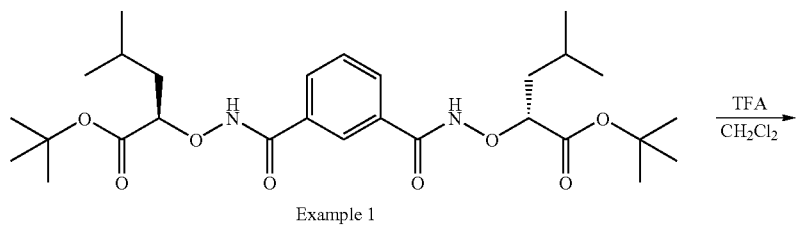

Example 1

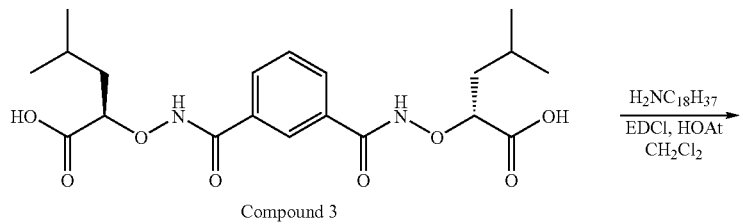

Compound 3

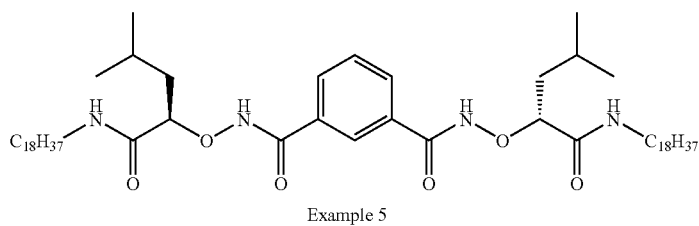

Example 5

Example 5 was prepared according to Scheme E above which was similar to Scheme B for Example 2 except that isobutylamine was replaced with octadecylamine. Example 5 was isolated as a white solid. Example 5 was characterized by the following data: m.p. 88-90° C.; $[\alpha]^{20}_D$+43.9° (c 1.00, CHCl$_3$); $^1$H NMR (300 MHz, CDCl$_3$) δ 11.11 (s, 2H), 8.18 (br, 3H), 8.05 (d, J=7.7 Hz, 2H), 7.55 (t, J=7.7 Hz, 1H), 4.36 (dd, J=8.8, 3.4 Hz, 2H), 3.15-3.05 (m, 4H), 1.80 (m, 2H), 1.65-1.54 (m, 4H), 1.41 (br, 4H), 1.30-1.16 (m, 60H), 0.89-0.84 (m, 18H); $^{13}$C NMR (75 MHz, CDCl$_3$) δ 172.03, 165.89, 131.98, 129.37, 124.98, 85.31, 41.06, 39.39, 31.89, 29.69, 29.60, 29.53, 29.33, 29.28, 29.12, 26.88, 24.68, 23.12, 22.56, 21.74, 14.08; IR (CHCl$_3$) 3444, 3345, 1662 cm$^{-1}$; LRMS (FAB) m/z 928 (M$^+$ 1); HRMS (MALDI) for C$_{56}$H$_{102}$N$_4$O$_6$ (M$^+$+Na): calculated 927.4323. found 949.7678.

Preparation of Example 6

Scheme F

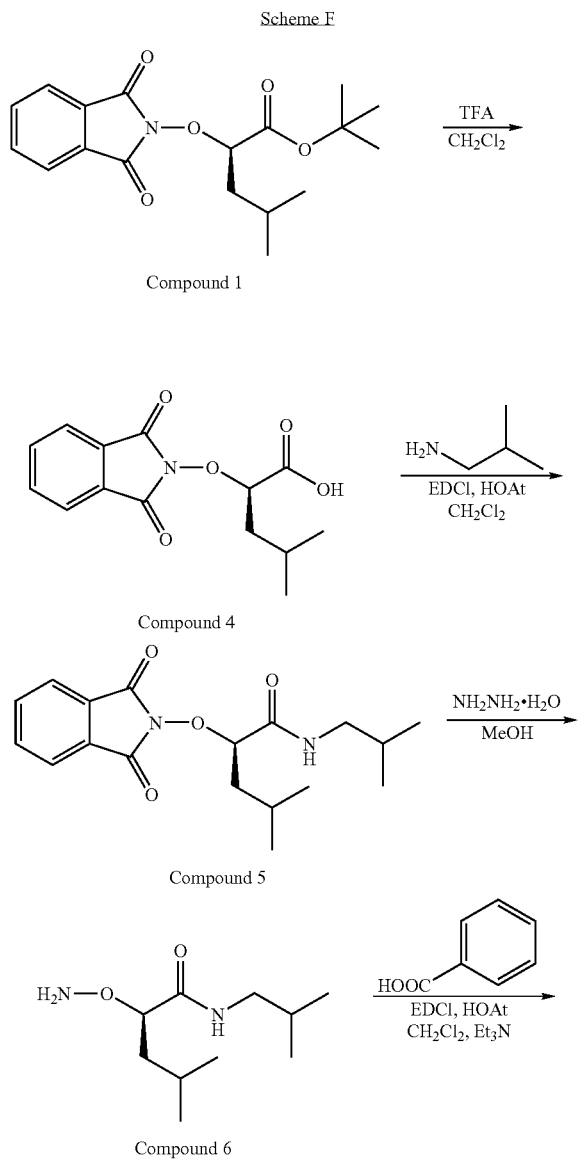

Compound 1

Compound 4

Compound 5

Compound 6

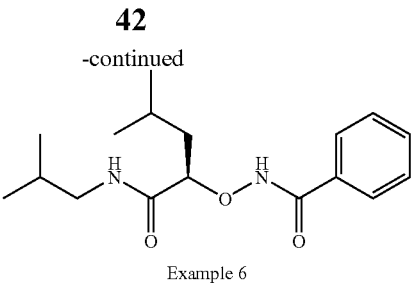

Example 6

Example 6 was prepared according to Scheme F above. To a solution of Compound 1 (1.00 g, 3.0 mmol) in CH$_2$Cl$_2$ (10 mL) was carefully added equal volume of CF$_3$COOH (10 mL) through a syringe at room temperature. After stirred at room temperature for 3 hours, the reaction mixture was concentrated under vacuo. The residue was azeotroped with toluene twice to give Compound 4 as a white solid and the white solid was used directly in the next step below.

Freshly distilled CH$_2$Cl$_2$ (80 mL) was added to a flask containing dried Compound 4 under nitrogen atmosphere, followed by the addition of HOAt (530 mg, 3.9 mmol), isobutylamine (0.32 mL, 3.15 mmol), and finally EDCI (1.34 g, 4.5 mmol). After being stirred overnight, the reaction mixture was diluted with CH$_2$Cl$_2$. The organic layer was washed with 5% NaHCO$_3$ and brine, then dried over anhydrous MgSO$_4$ and concentrated to afford compound 5 (0.99 g, 99%) as a white solid (Compound 5), which was used directly in the next step without further purification.

To a solution of Compound 5 in CH$_3$OH (10 mL) was added NH$_2$NH$_2$.H$_2$O (450 mg, 9.0 mmol). A white precipitate appeared after 1 hour. After stirred at room temperature for 2.5 hours, the reaction mixture was concentrated under vacuo. The residue was dissolved in CH$_2$Cl$_2$ and was washed with 5% NaHCO$_3$ twice and then with brine. The organic layer was dried over anhydrous NaSO$_4$ and concentrated to provide a mixture of Compound 6 and phthahydroazide as a colorless oil. This mixture was immediately used in the next step without further purification.

Freshly distilled CH$_2$Cl$_2$ (50 mL) was added to a flask containing dried Compound 6 under nitrogen atmosphere, followed by the addition of HOAt (530 mg, 3.9 mmol), benzoic acid (366 mg, 3.0 mmol), triethylamine (0.41 mL, 3.0 mmol), and finally EDCI (1.34 g, 4.5 mmol). After stirred overnight, the reaction mixture was diluted with CH$_2$Cl$_2$. The organic layer was washed with 5% NaHCO$_3$ and brine, then dried over anhydrous MgSO$_4$ and concentrated. The crude oil was purified by flash column chromatography to afford Example 6 (832 mg, 86%) as a white solid. Example 6 was characterized by the following data: m.p. 130-132° C.; $[\alpha]^{20}_D$+31.7° (c 1.00, CHCl$_3$); $^1$H NMR (400 M/z, CDCl$_3$) δ 9.98 (br, 1H), 8.21 (br, 1H), 7.75 (d, J=7.5 Hz, 2H), 7.52 (t, J=7.3 Hz, 1H), 7.52 (t, J=7.6 Hz, 2H), 4.40 (dd, J=9.4, 3.8 Hz, 1H), 3.13-2.97 (m, 2H), 1.85-1.61 (m, 4H), 0.92-0.85 (m, 12H); $^{13}$C NMR (75 MHz, CDCl$_3$) δ 171.94, 167.74, 132.41, 131.01, 128.65, 127.27, 85.40, 46.61, 40.97, 28.32, 24.71, 23.19, 21.62, 20.06, 19.88; IR (CHCl$_3$) 3345, 1659 cm$^{-1}$; LRMS (EI, 20 eV) m/z 307 (M$^+$, 1); HRMS (EI, 20 eV) for C$_{17}$H$_{26}$N$_2$O$_3$ (M$^+$): calculated 306.1943. found 306.1923.

Preparation of Example 7

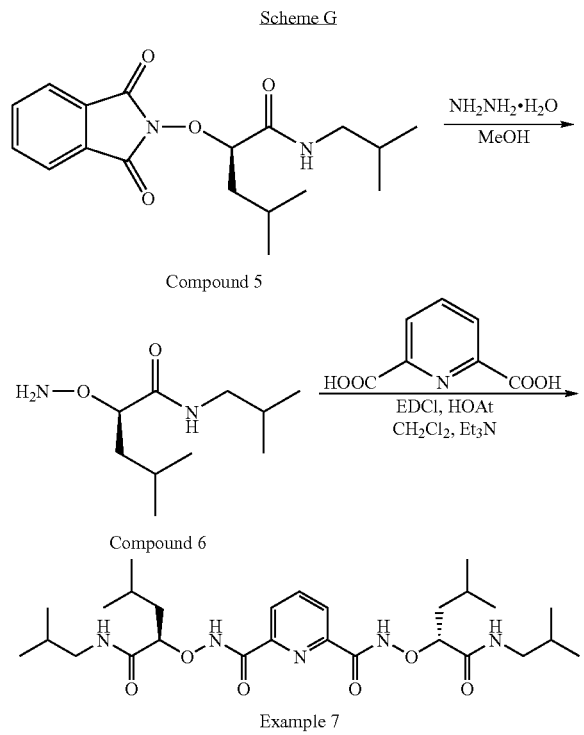

Preparation of Example 8

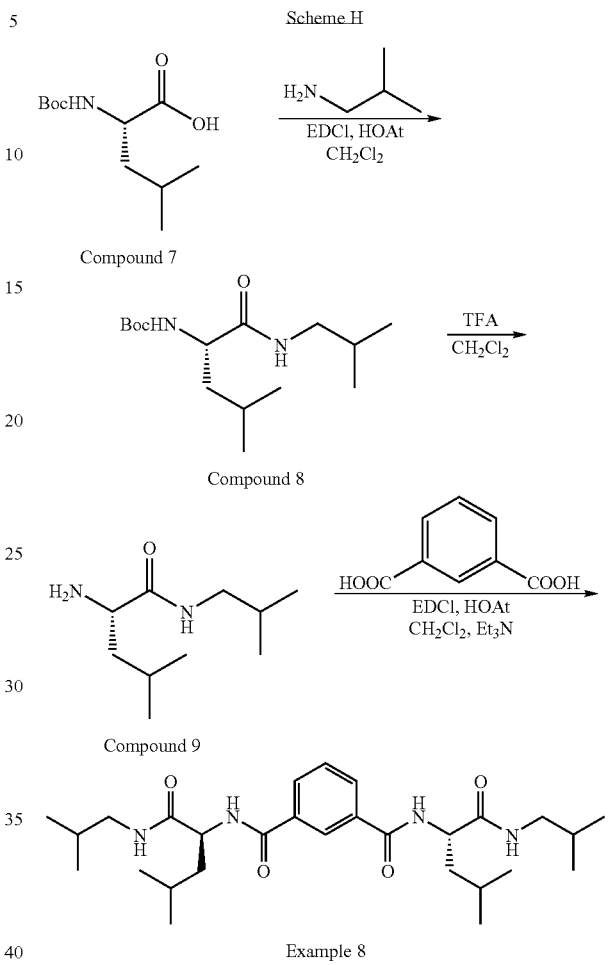

Example 7 was prepared according to Scheme G above. To a solution of Compound 5 (332 mg, 1 mmol) in CH$_3$OH (10 mL) was added NH$_2$NH$_2$—H$_2$O (150 mg, 3.0 mmol). A white precipitate appeared after 1 hour. After stirred at room temperature for 2.5 hours, the reaction mixture was concentrated under vacuo. The residue was dissolved in CH$_2$Cl$_2$ and was washed with 5% NaHCO$_3$ twice and then with brine. The organic layer was dried over anhydrous Na$_2$SO$_4$ and concentrated to provide a mixture of Compound 6 and phthahydroazide as a colorless oil. This mixture was immediately used in the next step without further purification.

Freshly distilled CH$_2$Cl$_2$ (50 mL) was added to a flask containing dried Compound 6 under nitrogen atmosphere, followed by the addition of HOAt (177 mg, 1.3 mmol), pyridine-2,6-dicarboxylic acid (366 mg, 0.5 mmol), triethylamine (0.14 mL, 1.0 mmol), and finally EDCI (447 mg, 1.5 mmol). After stirred overnight, the reaction mixture was diluted with CH$_2$Cl$_2$. The organic layer was washed with 5% NaHCO$_3$ and brine, then dried over anhydrous MgSO$_4$ and concentrated. The crude oil was purified by flash column chromatography to afford Example 7 (214 mg, 80%) as a white solid. Example 7 was characterized by the following data: m.p. 175-177° C.; [α]$^{20}_D$+117.2° (c 0.50, CHCl$_3$); $^1$H NMR (300 MHz, CDCl$_3$) δ 11.97 (s, 2H), 8.31 (d, J=7.8 Hz, 2H), 8.20 (t, J=5.7 Hz, 2H), 8.10 (t, J=7.8 Hz, 1H), 4.41 (dd, J=8.6, 4.2 Hz, 2H), 3.05-2.98 (m, 4H), 1.81-1.60 (m, 8H), 0.90-0.78 (m, 24H); $^{13}$C NMR (75 MHz, CDCl$_3$) δ 171.73, 162.30, 147.51, 139.20, 125.59, 85.30, 46.68, 41.12, 28.16, 24.65, 23.03, 21.97, 19.99, 19.95; IR (CHCl$_3$) 3321, 1673 cm$^{-1}$; LRMS (EI, 20 eV) m/z 535 (M$^+$); HRMS (EI, 20 eV) for C$_{27}$H$_{45}$N$_5$O$_6$ (M$^+$): calculated 535.3370. found 535.3371.

Example 8 was prepared according to Scheme H above. N-Boc-L-leucine (Compound 7) (693 mg 3.0 mmol) was dissolved in freshly distilled CH$_2$Cl$_2$ (50 mL) under nitrogen atmosphere, followed by the addition of HOAt (530 mg, 3.9 mmol), isobutylamine (0.32 mL, 3.15 mmol), and finally EDCI (1.34 g, 4.5 mmol). After stirred overnight, the reaction mixture was diluted with CH$_2$Cl$_2$. The organic layer was washed with 5% NaHCO$_3$ and brine, then dried over anhydrous MgSO$_4$ and concentrated to afford Compound 8 (851 mg, 99%) as a white solid, which was used directly in the next step without further purification.

To a solution of Compound 8 in CH$_2$Cl$_2$ (5 mL) was carefully added equal volume of CF$_3$COOH (5 mL) through a syringe at room temperature. After stirred at room temperature for 3 hour, the reaction mixture was concentrated under vacuo. The residue was dissolved in CHCl$_3$, washed with K$_2$CO$_3$ solution (pH=12) and brine, dried over anhydrous Na$_2$SO$_4$, and concentrated to give free amine Compound 9 as a colorless oil, which was used directly in the next step.

Freshly distilled CH$_2$Cl$_2$ (50 mL) was added to a flask containing dried Compound 9 under nitrogen atmosphere, followed by the addition of HOAt (530 mg, 3.9 mmol), isophthalic acid (249 mg, 1.5 mmol), triethylamine (0.41 mL, 3.0 mmol), and finally EDCI (1.34 g, 4.5 mmol). After being stirred overnight, the reaction mixture was diluted with $CH_2Cl_2$. The organic layer was washed with 5% $NaHCO_3$ and brine, then dried over anhydrous $MgSO_4$ and concentrated. The crude oil was purified by flash column chromatography to afford Example 8 (617 mg, 82%) as a white solid. Example 8 was characterized by the following data: m.p. 240-242° C.; $[\alpha]^{20}{}_D$32.1° (c 1.00, $CHCl_3$); $^1H$ NMR (500 MHz, $CDCl_3$) δ 8.20 (s, 1H), 7.92 (d, J=7.8 Hz 2H), 7.48 (t, J=7.8 Hz, 1H), 7.09 (d, J=8.2 Hz, 2H), 6.35 (t, J=5.8 Hz, 2H), 4.65 (m, 2H), 3.15-3.10 (m, 2H), 3.05-3.00 (m, 2H), 1.81-1.69 (m, 8H), 0.97 (d, J=6.7 Hz, 12H), 0.90 (d, J=6.7 Hz, 12H); $^{13}C$ NMR (125 MHz, $CDCl_3$) δ 172.01, 166.53, 134.19, 130.47, 128.98, 125.53, 52.48, 46.94, 41.27, 28.45, 24.93, 22.86, 22.31, 20.08, 20.06; IR ($CHCl_3$) 3400, 1653 $cm^{-1}$; LRMS (EI, 20 eV) m/z 503 ($M^+$); HRMS (EI, 20 eV) for $C_{28}H_{46}N_4O_4$ ($M^+$): calculated 502.3519. found 502.3486.

Preparation of Example 9

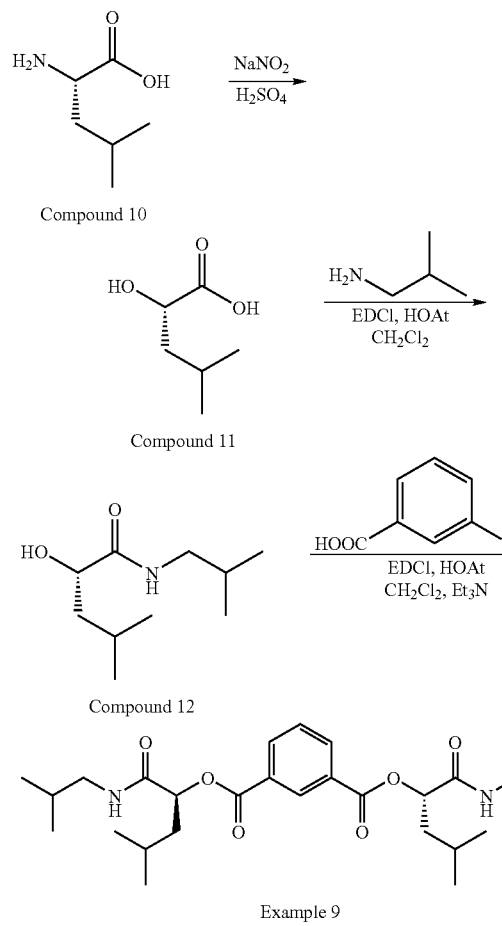

Example 9 was prepared according to Scheme I above. Concentrated sulphuric acid (0.48 mL) was added cautiously to water (22 mL) in a 100 mL round-bottom flask containing L-leucine (Compound 10) (787 mg, 6.0 mmol). A solution of $NaNO_2$ (1.24 g, 18 mmol) in water (40 mL) was added through a dropping funnel at such a rate that the temperature of the reaction mixture does not exceed 5° C. After stirred at 0° C. for 1 hour, the reaction mixture was slowly warmed to room temperature and stirred for another 1 hour. The product was extracted with ethyl acetate and the organic layer was washed with brine and then dried over anhydrous $MgSO_4$. The organic solvent was evaporated off to give a sticky light yellow oil Compound 11, which was used directly in the next step.

Freshly distilled $CH_2Cl_2$ (50 mL) was added to a flask containing Compound 11 under nitrogen atmosphere, followed by the addition of HOAt (1.06 g, 7.8 mmol), isobutylamine (0.63 mL, 6.3 mmol), and finally EDCI (2.68 g, 9.0 mmol). After being stirred overnight, the reaction mixture was diluted with $CH_2Cl_2$. The organic layer was washed with 5% $NaHCO_3$ and brine, then dried over anhydrous $MgSO_4$ and concentrated to afford Compound 12 as a white solid, which was used directly in the next step without further purification.

Freshly distilled $CH_2Cl_2$ (50 mL) was added to a flask containing Compound 12 under nitrogen atmosphere, followed by the addition of HOAt (1.06 g, 7.8 mmol), isophthalic acid (500 mg, 3 mmol), triethylamine (0.82 mL, 6.0 mmol), and finally EDCI (2.68 g, 9.0 mmol). After stirred overnight, the reaction mixture was diluted with $CH_2Cl_2$. The organic layer was washed with 5% $NaHCO_3$ and brine, then dried over anhydrous $MgSO_4$ and concentrated. The crude oil was purified by flash column chromatography to afford Example 9 (1.02 g, 68%) as a white solid. Example 9 was characterized by the following data: m.p. 137-139° C.; $[\alpha]^{20}{}_D$+22.6° (c 1.00, $CHCl_3$); $^1H$ NMR (400 MHz, $CDCl_3$) δ 8.74 (t, J=1.6 Hz, 1H), 8.32 (dd, J=7.8, 1.7 Hz, 2H), 7.63 (t, J=7.8 Hz, 1H), 6.06 (t, J=5.7 Hz, 2H), 5.43 (dd, J=9.4, 3.9 Hz, 2H), 3.11 (t, J=6.6 Hz, 4H), 1.96-1.75 (m, 8H) 1.00-0.97 (m, 12H), 0.90-0.87 (m, 12H) $^{13}C$ NMR (100 MHz, $CDCl_3$) δ 169.78, 164.66, 134.48, 130.85, 130.08, 129.20, 74.03, 46.50, 40.78, 28.45, 24.73, 23.13, 21.81, 19.94; IR ($CHCl_3$) 3450, 1729, 1679 $cm^{-1}$; LRMS (EI, 20 eV) m/z 504 ($M^+$); HRMS (EI, 20 eV) for $C_2H_{44}N_2O_6$ ($M^+$): calculated 504.3199. found 504.3199.

Alternative Preparation Method for Example 2

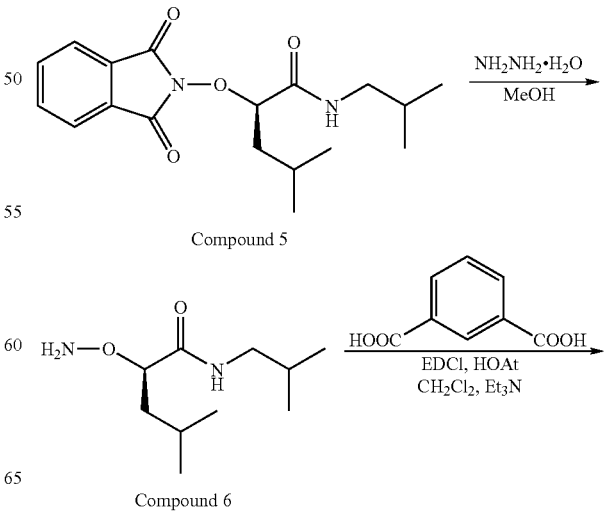

-continued

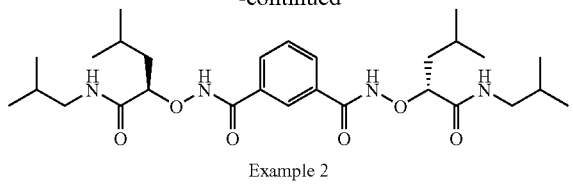

Example 2

Example 2 was also prepared according to Scheme J above which was similar to Scheme G for Example 7 except that pyridine-2,6-dicarboxylic acid was replaced with isophthalic acid. Example 2 was isolated as a white solid which was characterized by the following data: m.p. 176-178° C.; $[\alpha]^{20}{}_D$ (deg cm$^3$g$^{-1}$ dm$^{-1}$) +67.3° (c=0.01 g cm$^{-3}$ in CHCl$_3$); $^1$H-NMR (600 MHz, CDCl$_3$) δ 10.43 ppm (s, 2H), 8.12 (s, 1H), 8.07 (t, J=5.7 Hz, 2H), 8.04 (d, J=7.8 Hz, 2H), 7.57 (t, J=7.8 Hz, 1H), 4.40 (dd, J=9.5, 3.4 Hz, 2H), 3.05-3.01 (m, 2H), 2.91-2.88 (m, 2H), 1.86-1.62 (m, 8H), 0.92 (d, J=6.6 Hz, 12H), 0.84 (d, J=6.7 Hz, 6H), 0.78 (d, J=6.7 Hz, 6H); $^{13}$C-NMR (75 MHz, CDCl$_3$) δ 171.89, 166.14, 131.97, 131.30, 129.69, 124.93, 85.60, 46.69, 41.15, 28.29, 24.85, 23.18, 21.81, 20.04, 19.99; IR (CHCl$_3$) 3332 cm$^{-1}$, 3185, 1663 (C=O) cm$^{-1}$; LRMS (EI, 20 eV) m/z 534 (M$^+$); HRMS (EI, 20 eV) (m/z): [M$^+$] calculated for C$_{28}$H$_{46}$N$_4$O$_6$, 534.3417. found 534.3435.

Preparation of Example 10

Scheme K

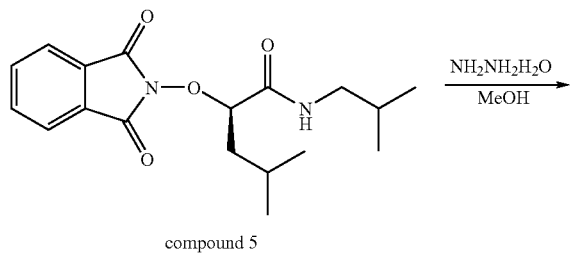

Example 10 was prepared according to Scheme K above. To a solution of Compound 5 (332 mg, 1 mmol) in CH$_3$OH (10 mL) was added NH$_2$NH$_2$·H$_2$O (150 mg, 3.0 mmol). A white precipitate appeared after 1 hour. After stirred at room temperature for 2.5 hours, the reaction mixture was concentrated under vacuo. The residue was dissolved in CH$_2$Cl$_2$ and was washed with 5% aqueous NaHCO$_3$ twice and then with brine. The organic layer was dried over with anhydrous Na$_2$SO$_4$ and concentrated to provide a mixture of Compound 6 and phthahydroazide as a colorless oil. This mixture was immediately used in the next step without Her purification.

Freshly distilled CH$_2$Cl$_2$ (50 mL) was added to a flask containing dried Compound 6 under nitrogen atmosphere, followed by the addition of HOAt (177 mg, 1.3 mmol), terephthalic acid (83 mg, 0.5 mmol), triethylamine (0.14 mL, 1.0 mmol), and finally N-(3-dimethylaminopropyl)-N'-ethylcarbodiimide hydrochloride (EDC.HCl, 300 mg, 1.5 mmol). After stirred overnight, the reaction mixture was diluted with CH$_2$Cl$_2$. The organic layer was washed with 5% aqueous NaHCO$_3$ twice and then with brine. The organic layer was dried over with anhydrous MgSO$_4$ and concentrated. The crude oil was purified by flash column chromatography to afford Example 10 (107 mg, 40%) as a white solid. Example 10 was characterized by the following data: $[\alpha]^{20}{}_D$+58.9° (c 1.00, DMSO); $^1$H NMR (300 MHz, DMSO-d$_6$) δ 12.03 (s, 2H), 8.24 (s, 2H), 7.82 (s, 4H), 4.38 (dd, J=8.5, 4.5 Hz, 2H), 2.96-2.90 (m, 4H), 1.83-1.50 (m, 8H), 0.98 (d, J=6.5 Hz, 6H) 0.93 (d, J=6.5 Hz, 6H), 0.81 (d, J=6.6 Hz, 6H), 0.79 (d, J=6.6 Hz, 6H); $^{13}$C NMR (75 MHz, DMSO-d$_6$) δ 170.93, 164.99, 135.00, 127.79, 84.01, 46.25, 28.42, 24.66, 23.47, 22.47, 20.40, 20.16; LRMS (EI, 20 eV) m/z 534 (M$^+$, 1), 131 (100); HRMS (EI) for C$_{28}$H$_{46}$N$_4$O$_6$ (M$^+$): calculated 534.3417. found 534.3419.

Preparation of Example 11

Scheme L

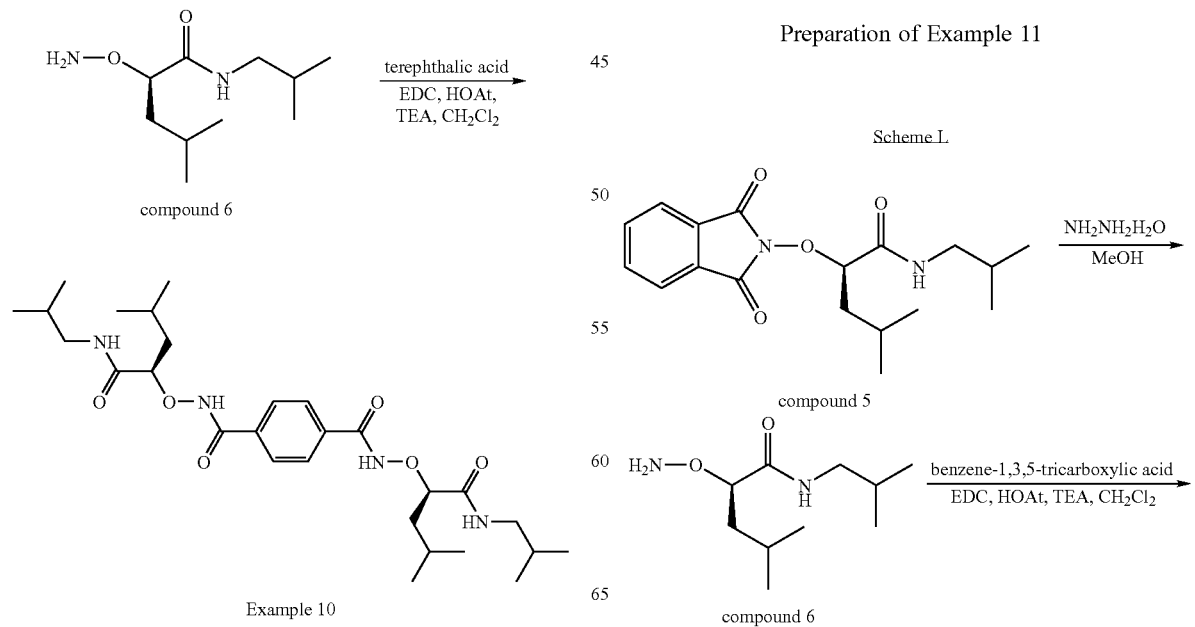

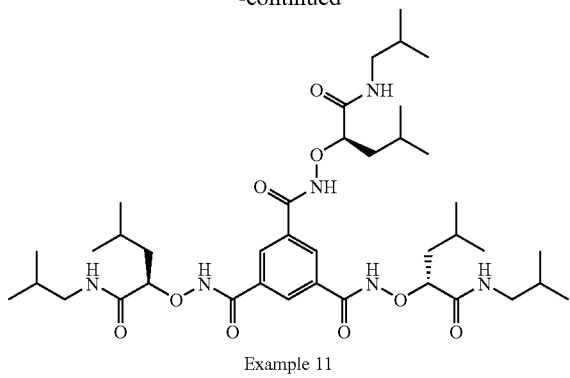

Example 11

Example 11 was prepared according to Scheme L above. To a solution of Compound 5 (332 mg, 1 mmol) in CH$_3$OH (10 mL) was added NH$_2$NH$_2$.H$_2$O (150 mg, 3.0 mmol). A white precipitate appeared after 1 hour. After stirred at room temperature for 2.5 hours, the reaction mixture was concentrated under vacuo. The residue was dissolved in CH$_2$Cl$_2$ and was washed with 5% aqueous NaHCO$_3$ twice and then with brine. The organic layer was dried over with anhydrous Na$_2$SO$_4$ and concentrated to provide a mixture of Compound 6 and phthahydroazide as a colorless oil. This mixture was immediately used in the next step without further purification.

Freshly distilled CH$_2$Cl$_2$ (50 mL) was added to a flask containing dried Compound 6 under nitrogen atmosphere, followed by the addition of HOAt (177 mg, 1.3 mmol), benzene-1,3,5-tricarboxylic acid (105 mg, 0.5 mmol), triethylamine (0.14 mL, 1.0 mmol), and finally EDC.HCl (300 mg, 1.5 mmol). After stirred overnight, the reaction mixture was diluted with CH$_2$Cl$_2$. The organic layer was washed with 5% aqueous NaHCO$_3$ twice and then with brine. The organic layer was dried over with anhydrous MgSO$_4$ and concentrated. The crude oil was purified by flash column chromatography to afford Example 11 (171 mg, 45%) as a white solid. Example 11 was characterized by the following data: [α]$^{20}_D$+46.1° (c 1.00, DMSO); $^1$H NMR (400 MHz, DMSO-d$_6$) δ 12.14 (s, 3H), 8.26 (s, 3H), 8.22 (s, 3H), 4.38 (dd, J=8.4, 4.0 Hz, 3H), 3.00-2.89 (m, 6H), 1.85-1.51 (m, 12H), 0.98 (d, J=6.5 Hz, 9H), 0.93 (d, J=6.6 Hz, 9H), 0.81 (d, J=7 Hz, 9H), 0.79 (d, J=8 Hz, 9H); $^{13}$C NMR (100 MHz, DMSO-d$_6$) δ 170.97, 164.43, 132.80, 129.45, 84.19, 46.25, 28.43, 24.69, 23.48, 22.42, 20.40; LRMS (FAB) m/z 763 (M$^+$+H); HRMS (FAB) for C$_{39}$H$_{67}$N$_6$O$_9$ (M$^+$+H): calculated 763.4891. found 763.4949.

Preparation of Examples 12 and 13

Scheme M

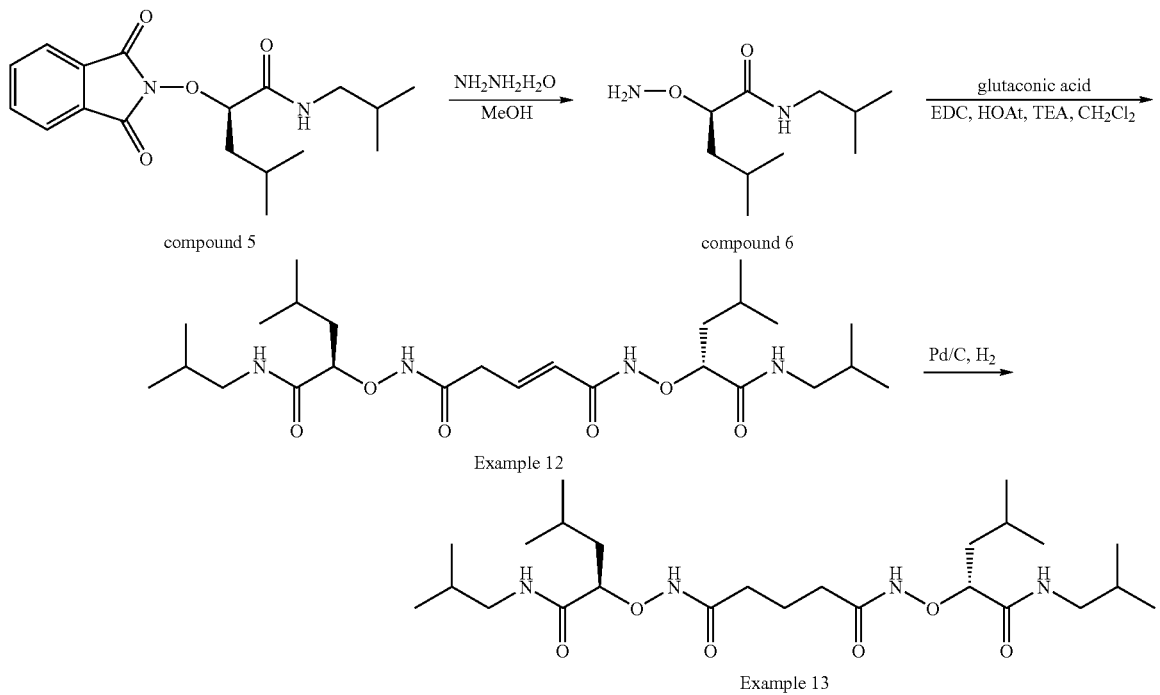

Examples 12 and 13 were prepared according to Scheme M above. To a solution of Compound 5 (332 mg, 1 mmol) in CH$_3$OH (10 mL) was added NH$_2$NH$_2$.H$_2$O (150 mg, 3.0 mmol). A white precipitate appeared after 1 hour. After stirred at room temperature for 2.5 hours, the reaction mixture was concentrated under vacuo. The residue was dissolved in CH$_2$Cl$_2$ and was washed with 5% aqueous NaHCO$_3$ twice and then with brine. The organic layer was dried over with anhydrous Na$_2$SO$_4$ and concentrated to provide a mixture of Compound 6 and phthahydroazide as a colorless oil. This mixture was immediately used in the next step without further purification.

Freshly distilled CH$_2$Cl$_2$ (50 mL) was added to a flask containing dried Compound 6 under nitrogen atmosphere, followed by the addition of HOAt (177 mg, 1.3 mmol), glutaconic acid (65 mg, 0.5 mmol), triethylamine (0.14 mL, 1.0 mmol), and finally EDC.HCl (300 mg, 1.5 mmol). After stirred overnight, the reaction mixture was diluted with $CH_2Cl_2$. The organic layer was washed with 5% aqueous $NaHCO_3$ twice and then with brine. The organic layer was dried over with anhydrous $MgSO_4$ and concentrated. The crude oil was purified by flash column chromatography to afford Example 12 (40 mg, 16%) as a white solid. Example 12 was characterized by the following data: $^1$H NMR (300 MHz, $CDCl_3$) δ 10.60 (br, 1H), 10.49 (br, 1H), 8.07 (br, 1H), 7.88 (br, 1H), 6.88 (dt, J=15.4, 6.9 Hz, 1H), 5.89 (d, J=15 Hz, 1H), 4.28 (d, J=5.2 Hz, 2H), 3.11-2.97 (m, 6H), 1.84-1.60 (m, 8H), 0.95-0.87 (m, 24H); $^{13}$C NMR (100 MHz, $CDCl_3$) δ 171.97, 167.92, 137.25, 123.45, 85.31, 85.22, 46.70, 46.66, 40.98, 28.34, 24.71, 23.16, 21.71, 20.07; LRMS (EI, 20 eV) m/z 498 (M$^+$, 1), 131 (100); HRMS (EI) for $C_{25}H_{46}N_4O_6$ (M$^+$): calculated 498.3417. found 498.3436.

Example 12 (40 mg, 0.08 mmol) was dissolved in 1 mL MeOH, and 4 mg 10% Pd/C was added to the mixture. Then the mixture was stirred with $H_2$ at rt under balloon pressure overnight. The reaction mixture was filtered through celite and concentrated to afford Example 13 (40 mg, quant). Example 13 was characterized by the following data: $[\alpha]^{20}_D$+27.9° (c 1.00, $CHCl_3$); $^1$H NMR (300 MHz, $CDCl_3$) δ 7.69 (br, 2H), 4.35 (dd, J=8.6, 3.8 Hz, 2H), 3.29-3.24 (m, 2H), 2.87-2.85 (m, 2H), 2.18-2.16 (m, 2H), 1.88-1.63 (m, 12H), 1.00-0.92 (m, 24H); $^{13}$C NMR (75 MHz, $CDCl_3$) δ 172.72, 170.30, 86.21, 46.59, 40.77, 30.58, 28.44, 24.75, 23.04, 21.80, 20.71, 20.05; LRMS (EI, 20 eV) m/z 500 (M$^+$, 1), 131 (100); HRMS (EI) for $C_{25}H_{48}N_4O_6$ (M$^+$): calculated 500.3574. found 500.3596.

Preparation of Example 14

Example 14 was prepared according to Scheme N above. To a solution of Compound 5 (332 mg, 1 mmol) in $CH_3OH$ (10 mL) was added $NH_2NH_2.H_2O$ (150 mg, 3.0 mmol). A white precipitate appeared after 1 hour. After stirred at room temperature for 2.5 hours, the reaction mixture was concentrated under vacuo. The residue was dissolved in $CH_2Cl_2$ and was washed with 5% aqueous $NaHCO_3$ twice and then with brine. The organic layer was dried over with anhydrous $Na_2SO_4$ and concentrated to provide a mixture of Compound 6 and phthahydroazide as colorless oil. This mixture was immediately used in the next step without further purification.

Freshly distilled $CH_2Cl_2$ (50 mL) was added to a flask containing dried Compound 6 under nitrogen atmosphere, followed by the addition of HOAt (177 mg, 1.3 mmol), adipic acid (73 mg, 0.5 mmol), triethylamine (0.14 mL, 1.0 mmol), and finally EDC.HCl (300 mg, 1.5 mmol). After stirred overnight, the reaction mixture was diluted with $CH_2Cl_2$. The organic layer was washed with 5% aqueous $NaHCO_3$ twice and then with brine. The organic layer was dried over with anhydrous $MgSO_4$ and concentrated. The crude oil was purified by flash column chromatography to afford Example 14 (110 mg, 40%) as a white solid. Example 14 was characterized by the following data: $[\alpha]^{20}_D$+31.4° (c 1.00, $CHCl_3$); $^1$H NMR (300 MHz, $CDCl_3$) δ 9.78 (s, 2H), 7.98 (br, 2H), 4.30-4.26 (m, 2H), 3.21-3.14 (m, 2H), 3.02-2.93 (m, 2H), 2.12-2.11 (m, 4H), 1.73-1.60 (m, 12H), 0.99-0.91 (m, 24H); $^{13}$C NMR (100 MHz, $CDCl_3$) δ 172.11, 171.89, 85.35, 46.55, 41.02, 32.37, 28.36, 24.71, 23.16, 21.71, 20.07; LRMS (EI, 20 eV) m/z 515 (M$^+$+1, 10), 131 (100); HRMS (EI) for $C_{26}H_{50}N_4O_6$ (M$^+$): calculated 514.373. found 514.3768.

Scheme N

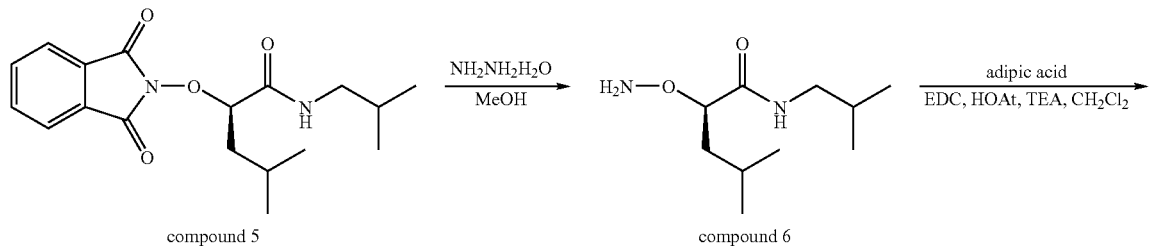

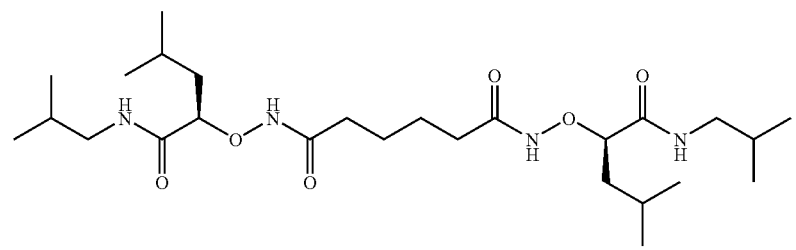

Example 14

Preparation of Example 15

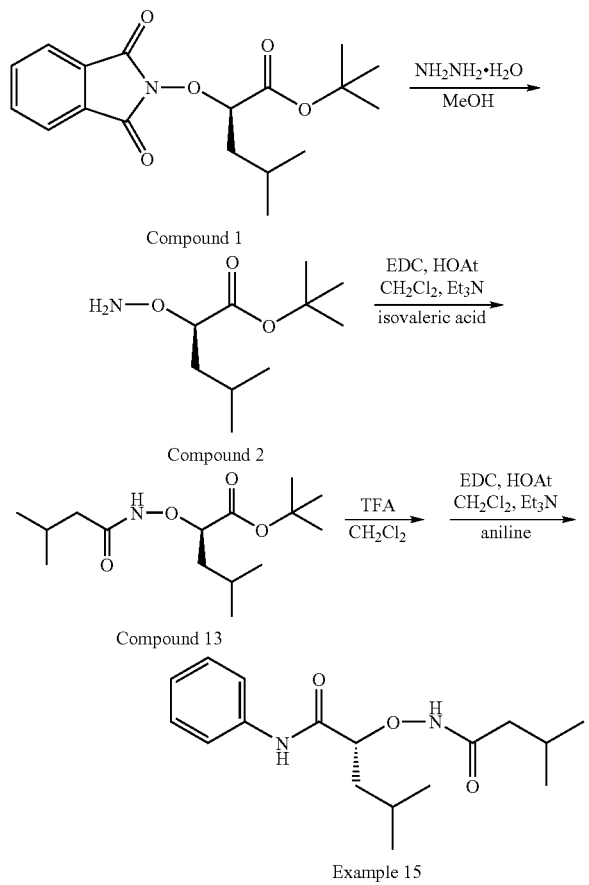

Example 15 was prepared according to Scheme O above. To a solution of Compound 1 (2.00 g, 6.0 mmol) in CH$_3$OH (20 mL) was added NH$_2$NH$_2$·H$_2$O (900 mg, 18.0 mmol). A white precipitate appeared after 1 hour. After being stirred at room temperature for 2.5 hours, the reaction mixture was concentrated under vacuo. The residue was dissolved in CH$_2$Cl$_2$ and washed with 5% aqueous NaHCO$_3$ twice and then with brine. The organic layer was dried over with anhydrous Na$_2$SO$_4$ and concentrated to provide a mixture of the free amine (Compound 2) and phthahydroazide as colorless oil. This mixture was immediately used in the peptide coupling reaction below without further purification.

Freshly distilled CH$_2$Cl$_2$ (80 mL) was added to a flask containing dried Compound 2 under nitrogen atmosphere, followed by the additions of 1-hydroxy-7-azabenzotriazole (HOAt, 1.05 g, 7.8 mmol), isovaleric acid (0.66 ml, 6.0 mmol), triethylamine (0.83 mL, 6.0 mmol), and finally EDC.HCl (1.80 g, 9 mmol). After stirred overnight, the reaction mixture was diluted with CH$_2$Cl$_2$. The organic layer was washed with 5% aqueous NaHCO$_3$ twice and then with brine. The organic layer was dried over with anhydrous MgSO$_4$ and concentrated. The crude oil was purified by flash column chromatography to afford compound 13 (1.07 g, 62% yield) of. Compound 13 was characterized by the following data: $[\alpha]^{20}_D$+138.1° (c 1.00, CH$_2$Cl$_2$); $^1$H NMR (300 MHz, CDCl$_3$) δ 8.78 (s, 1H), 4.44 (br, 1H), 2.13-1.93 (m, 4H), 1.70-1.51 (m, 2H), 1.48 (s, 9H), 1.03-0.93 (m, 12H); $^{13}$C NMR (75 MHz, CDCl$_3$) δ 171.85, 169.62, 81.99, 42.37, 39.85, 28.02, 25.84, 24.56, 23.09, 22.45, 22.27, 21.74; LRMS (EI, 20 eV) m/z 287 (M$^+$, 2), 186 (88), 102 (100); HRMS (EI) for C$_{15}$H$_{29}$NO$_4$ (M$^+$): calculated 287.2100. found 287.2101.

Freshly distilled CH$_2$Cl$_2$ (30 mL) was added to a flask containing dried Compound 13 (860 mg, 3.0 mmol) under nitrogen atmosphere, followed by the addition of TFA (6 mL, 75 mmol). The mixture was stirred at room temperature till Compound 13 was consumed. Then the reaction mixture was concentrated in vacuum and azeotroped with toluene 3 times to give the acid, which was used for next step without further purification.

Freshly distilled CH$_2$Cl$_2$ (80 mL) was added to a flask containing the acid afforded in the last step under nitrogen atmosphere, followed by the additions of 1-hydroxy-7-azabenzotriazole (HOAt, 0.525 g, 3.9 mmol), aniline (0.3 mL, 3.3 mmol), triethylamine (0.42 mL, 3 mmol), and finally EDC.HCl (0.90 g, 4.5 mmol). After stirred overnight, the reaction mixture was diluted with CH$_2$Cl$_2$. The organic layer was washed with 5% aqueous NaHCO$_3$ twice and then with brine. The organic layer was dried over with anhydrous MgSO$_4$ and concentrated. The crude oil was purified by flash column chromatography to afford Example 15 (0.8 g, 88% yield). Example 15 was characterized by the following data: $[\alpha]^{20}_D$+128.6° (c 1.00, CH$_2$Cl$_2$); $^1$H NMR (300 MHz, CDCl$_3$) δ 10.17 (s, 1H), 8.58 (s, 1H), 7.69 (d, J=7.8 Hz, 2H), 7.32 (t, J=7.7 Hz, 2H), 7.1 (t, J=7.4 Hz, 1H), 4.34 (t, J=6.8 Hz, 1H), 2.10-1.90 (m, 4H), 1.80-1.76 (m, 2H), 0.99 (t, J=6.5 Hz, 6H), 0.91 (d, J=6.6 Hz, 3H), 0.84 (d, J=6.6 Hz, 3H); $^{13}$C NMR (75 MHz, CDCl$_3$) δ 173.02, 169.97, 137.76, 128.86, 124.28, 119.97, 86.12, 41.89, 40.80, 25.86, 24.82, 23.20, 22.28, 22.02, 21.70; LRMS (EI, 20 eV) m/z 306 (M$^+$, 38), 151 (100); HRMS (EI) for C$_{17}$H$_{26}$N$_2$O$_3$ (M$^+$): calculated 306.1900. found 306.1937.

Preparation of Example 16

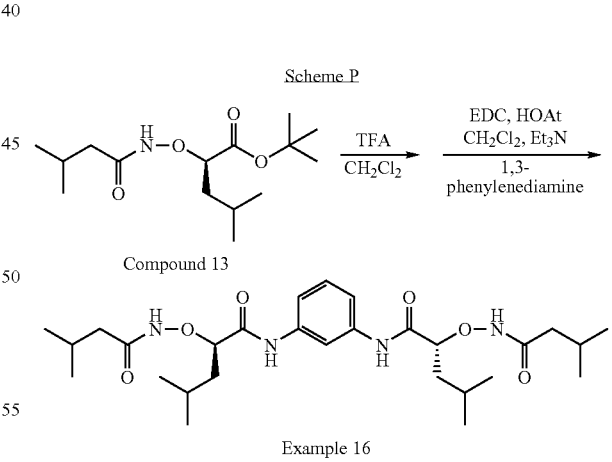

Example 16 was prepared according to Scheme P above. Freshly distilled CH$_2$Cl$_2$ (30 mL) was added to a flask containing dried Compound 13 (860 mg, 3.0 mmol) under nitrogen atmosphere, followed by the addition of TFA (6 mL, 75 mmol). The mixture was stirred at room temperature till Compound 13 was consumed. Then the reaction mixture was concentrated in vacuum and azeotroped with toluene 3 times to give the acid, which was used for next step without further purification.

Freshly distilled CH$_2$Cl$_2$ (80 mL) was added to a flask containing the acid afforded in the last step under nitrogen atmosphere, followed by the additions of 1-hydroxy-7-azabenzotriazole (HOAt, 0.525 g, 3.9 mmol), 1,3-phenylenediamine (162 mg, 1.5 mmol), triethylamine (0.42 mL, 3 mmol), and finally EDC.HCl (0.90 g, 4.5 mmol). After stirred overnight, the reaction mixture was diluted with CH$_2$Cl$_2$. The organic layer was washed with 5% aqueous NaHCO$_3$ twice and then with brine. The organic layer was dried over with anhydrous MgSO$_4$ and concentrated. The crude oil was purified by flash column chromatography to afford Example 16 (0.24 g, 30% yield). Example 16 was characterized by the following data: $[\alpha]^{20}_D$+163.0° (c 1.00, CH$_2$Cl$_2$); $^1$H NMR (400 MHz, DMSO-d$_6$) δ 11.33 (s, 2H), 10.34 (s, 2H), 7.98 (s, 1H), 7.35 (d, J=8.2 Hz, 2H), 7.24 (t, J=8 Hz, 1H), 4.37 (dd, J=9.1, 4.2 Hz, 2H), 1.95-1.85 (m, 8H), 1.77-1.55 (m, 2H), 1.55-1.45 (m, 2H), 0.97 (d, J=6.6 Hz, 6H), 0.93 (d, J=6.6 Hz, 6H), 0.84-0.80 (m, 12H); $^{13}$C NMR (100 MHz, CDCl$_3$) δ 170.70, 170.12, 139.18, 129.32, 115.30, 111.19, 84.33, 41.51, 40.71, 25.78, 24.65, 23.52, 22.49, 22.46, 22.28; LRMS (EI, 20 eV) m/z 535 (M$^+$+1, 22), 222 (100); HRMS (EI, 20 eV) for C$_{29}$H$_{46}$N$_4$O$_6$ (M$^+$): calculated 534.3417. found 534.3428.

Preparation of Example 17

Example 16 was prepared according to Scheme Q above. Freshly distilled CH$_2$Cl$_2$ (30 mL) was added to a flask containing dried Compound 13 (860 mg, 3.0 mmol) under nitrogen atmosphere, followed by the addition of TFA (6 mL, 75 mmol). The mixture was stirred at room temperature till Compound 13 was consumed. Then the reaction mixture was concentrated in vacuum and azeotroped with toluene 3 times to give the acid, which was used for next step without further purification.

Freshly distilled CH$_2$Cl$_2$ (80 mL) was added to a flask containing the acid afforded in the last step under nitrogen atmosphere, followed by the additions of 1-hydroxy-7-azabenzotriazole (HOAt, 0.525 g, 3.9 mmol), 1,4-phenylenediamine (162 mg, 1.5 mmol), triethylamine (0.42 mL, 3 mmol), and finally EDC·HCl (0.90 g, 4.5 mmol). After stirred overnight, the reaction mixture was diluted with CH$_2$Cl$_2$. The organic layer was washed with 5% aqueous NaHCO$_3$ twice and then with brine. The organic layer was dried over with anhydrous MgSO$_4$ and concentrated. The crude oil was purified by flash column chromatography to afford Example 17 (0.33 g, 41% yield). Example 17 was characterized by the following data: $[\alpha]^{20}_D$+236.2° (c 1.00, DMSO); $^1$H NMR (400 MHz, DMSO-d$_6$) δ 11.36 (s, 2H), 10.31 (s, 2H), 7.56 (s, 4H), 4.33 (dd, J=9.3, 4.1 Hz, 2H), 1.95-1.85 (m, 8H), 1.65-1.62 (m, 2H), 1.55-1.52 (m, 2H), Scheme Q

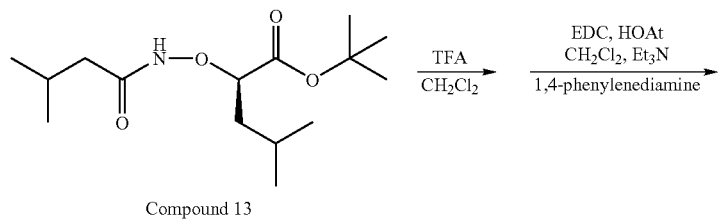

Compound 13

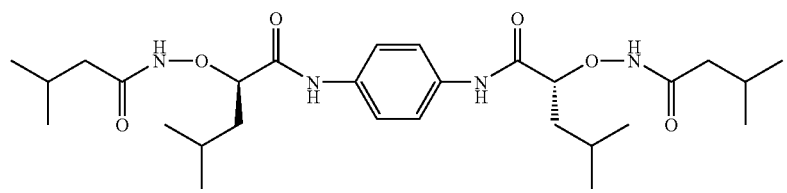

Example 17

0.97 (d, J=6.6 Hz, 6H), 0.93 (d, J=6.7 Hz, 6H), 0.83 (d, J=6.3 Hz, 6H), 0.80 (d, J=6.3 Hz, 6H); $^{13}$C NMR (100 MHz, DMSO-$d_6$) δ 170.75, 169.86, 134.64, 120.15, 84.44, 41.51, 40.74, 25.79, 25.57, 24.67, 23.52, 22.48, 22.43, 22.23; LRMS (EI, 20 eV) m/z 535 (M$^+$+1, 55), 222 (84), 108 (100); HRMS (EI, 20 eV) for $C_2H_{46}N_4O_6$ (M$^+$): calculated 534.3417. found 534.3405.

Preparation of Example 18

Scheme R

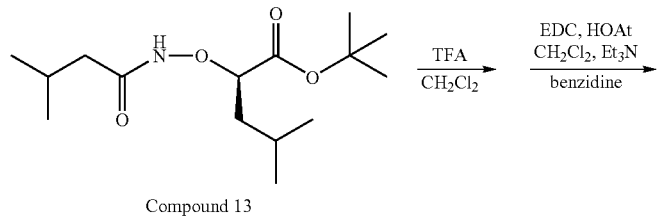

Compound 13

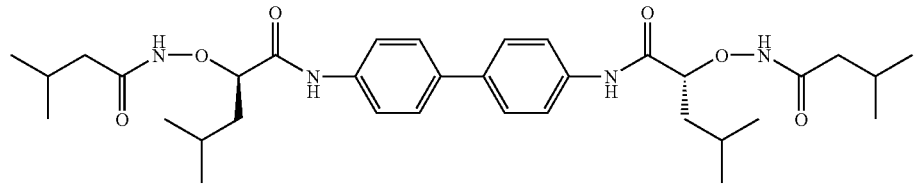

Example 18

Example 16 was prepared according to Scheme R above. Freshly distilled $CH_2Cl_2$ (30 mL) was added to a flask containing dried Compound 13 (860 mg, 3.0 mmol) under nitrogen atmosphere, followed by the addition of TFA (6 mL, 75 mmol). The mixture was stirred at room temperature till Compound 13 was consumed. Then the reaction mixture was concentrated in vacuum and azeotroped with toluene 3 times to give the acid, which was used for next step without further purification.

Freshly distilled $CH_2Cl_2$ (80 mL) was added to a flask containing the acid afforded in the last step under nitrogen atmosphere, followed by the additions of 1-hydroxy-7-azabenzotriazole (HOAt, 0.525 g, 3.9 mmol), benzidine (276 mg, 1.5 mmol), triethylamine (0.42 mL, 3 mmol), and finally EDC.HCl (0.90 g, 4.5 mmol). After stirred overnight, the reaction mixture was diluted with $CH_2Cl_2$. The organic layer was washed with 5% aqueous $NaHCO_3$ twice and then with brine. The organic layer was dried over with anhydrous $MgSO_4$ and concentrated. The crude oil was purified by flash column chromatography to afford Example 18 (0.6 g, 66% yield). Example 18 was characterized by the following data: $[\alpha]^{20}_D$+275.4° (c 1.00, Acetone); $^1$H NMR (400 MHz, DMSO-$d_6$) δ 11.40 (s, 2H), 10.45 (s, 2H), 7.70 (d, J=8.7 Hz, 4H), 7.62 (d, J=8.8 Hz, 4H), 4.37 (dd, J=9.3, 4.2 Hz, 2H), 1.95-1.86 (m, 8H), 1.78-1.55 (m, 2H), 1.45-1.23 (m, 2H), 0.98 (d, J=6.6 Hz, 6H), 0.94 (d, J=6.7 Hz, 6H), 0.84 (d, J=6.3 Hz, 6H), 0.82 (d, J=6.3 Hz, 6H); $^{13}$C NMR (100 MHz, DMSO-$d_6$) δ 170.85, 170.16, 138.01, 135.27, 126.94, 120.20, 84.57, 41.52, 40.74, 25.79, 24.68, 23.52, 22.49, 22.45, 22.26; LRMS (FAB) m/z 611 (M$^+$+H); HRMS (FAB) for $C_{34}H_{51}N_4O_6$ (M$^+$+H): calculated 611.373. found 611.3811.

Preparation of Example 19

Scheme S

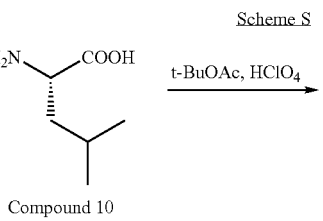

Compound 10

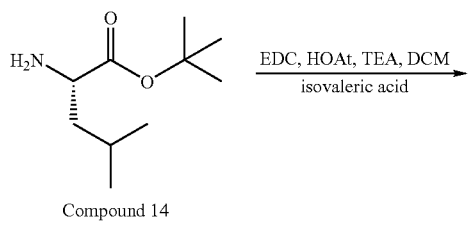

Compound 14

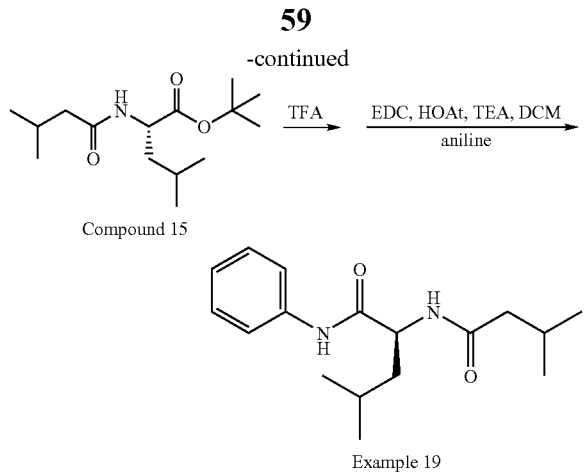

Example 19

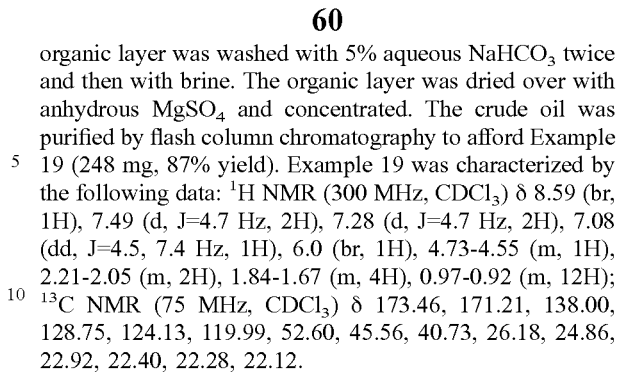

Compound 15

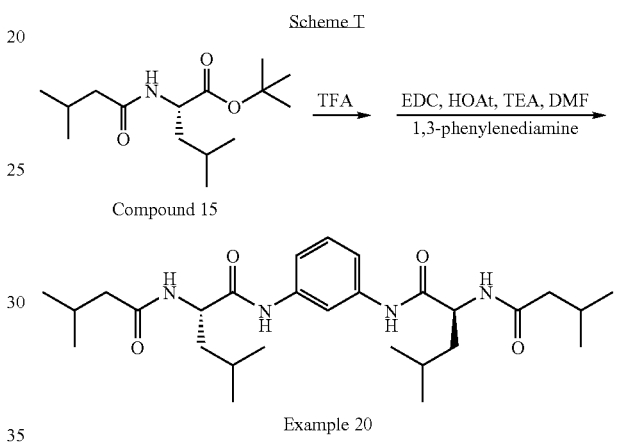

Example 20

Example 19 was prepared according to Scheme S above. Compound 14 was synthesized according to the procedures described in Miller et al., *J. Org. Chem.*, 1986, 51, 5332-5337. L-Leucine (2.88 g, 22 mmol) was dissolved in aqueous 60% perchloric acid (4 g, 24 mmol) with stirring in an ice bath. tert-Butyl acetate (75 mL) was added and the stirring was continued until a homogeneous solution was obtained. The mixture was kept at room temperature for 2 days, then 0.1N HCl (100 mL) was added to the mixture. The aqueous phase was separated from the ether phase, and the aqueous phase was adjusted with aqueous $Na_2CO_3$ to pH about 9. The aqueous phase was extracted 3 times with EtOAc and the organic layer was combined, washed with brine, dried over with anhydrous $MgSO_4$ and concentrated to afford Compound 14 (3.05 g, 74% yield) as a colorless oil, which was used directly in the next step.

Freshly distilled $CH_2Cl_2$ (80 mL) was added to a flask containing dried Compound 14 (540 mg, 2.9 mmol) under nitrogen atmosphere, followed by the additions of 1-hydroxy-7-azabenzotriazole (HOAt, 513 mg, 3.77 mmol), isovaleric acid (0.32 mL, 2.9 mmol), triethylamine (0.4 mL, 2.9 mmol), and finally EDC.HCl (870 mg, 4.35 mmol). After stirred overnight, the reaction mixture was diluted with $CH_2Cl_2$. The organic layer was washed with 5% aqueous $NaHCO_3$ twice and then with brine. The organic layer was dried over with anhydrous $MgSO_4$ and concentrated. The crude oil was purified by flash column chromatography to afford compound 15 (918 mg, 93% yield). Compound 15 was characterized by the following data: $^1$H NMR (300 MHz, $CDCl_3$) δ 5.8 (br, 1H), 4.64-4.45 (m, 1H), 2.12-2.05 (m, 3H), 1.70-1.50 (m, 3H), 1.46 (s, 9H), 0.97-0.89 (m, 12H); $^{13}$C NMR (75 MHz, $CDCl_3$) δ 172.5, 172.05, 81.78, 51.10, 45.99, 42.02, 27.95, 26.12, 24.94, 22.77, 22.44, 22.38, 22.08.

Freshly distilled $CH_2Cl_2$ (10 mL) was added to a flask containing dried Compound 15 (270 mg, 1.0 mmol) under nitrogen atmosphere, followed by the addition of TFA (5 mL). The mixture was stirred at room temperature till Compound 15 was consumed. Then the reaction mixture was concentrated in vacuum and azeotroped with toluene 3 times to give the acid, which was used for next step without further purification.

Distilled DMF (10 mL) was added to a flask containing the acid (215 mg, 1 mmol) afforded in the last step under nitrogen atmosphere, followed by the additions of 1-hydroxy-7-azabenzotriazole (HOAt, 177 mg, 1.3 mmol), aniline (0.1 mL, 1.1 mmol), triethylamine (0.14 mL, 1 mmol), and finally EDC.HCl (300 mg, 1.5 mmol). After stirred overnight, the reaction mixture was diluted with EtOAc. The organic layer was washed with 5% aqueous $NaHCO_3$ twice and then with brine. The organic layer was dried over with anhydrous $MgSO_4$ and concentrated. The crude oil was purified by flash column chromatography to afford Example 19 (248 mg, 87% yield). Example 19 was characterized by the following data: $^1$H NMR (300 MHz, $CDCl_3$) δ 8.59 (br, 1H), 7.49 (d, J=4.7 Hz, 2H), 7.28 (d, J=4.7 Hz, 2H), 7.08 (dd, J=4.5, 7.4 Hz, 1H), 6.0 (br, 1H), 4.73-4.55 (m, 1H), 2.21-2.05 (m, 2H), 1.84-1.67 (m, 4H), 0.97-0.92 (m, 12H); $^{13}$C NMR (75 MHz, $CDCl_3$) δ 173.46, 171.21, 138.00, 128.75, 124.13, 119.99, 52.60, 45.56, 40.73, 26.18, 24.86, 22.92, 22.40, 22.28, 22.12.

Preparation of Example 20

Example 20 was prepared according to Scheme T above. Freshly distilled $CH_2Cl_2$ (10 mL) was added to a flask containing dried Compound 15 (270 mg, 1.0 mmol) under nitrogen atmosphere, followed by the addition of TFA (5 mL). The mixture was stirred at room temperature till Compound 15 was consumed. Then the reaction mixture was concentrated in vacuum and azeotroped with toluene 3 times to give the acid, which was used for next step without further purification.

Distilled DMF (10 mL) was added to a flask containing the acid (215 mg, 1 mmol) afforded in the last step under nitrogen atmosphere, followed by the additions of 1-hydroxy-7-azabenzotriazole (HOAt, 177 mg, 1.3 mmol), 1,3-phenylenediamine (54 mg, 0.5 mmol), triethylamine (0.14 mL, 1 mmol), and EDC-HCl (300 mg, 1.5 mmol). After stirred overnight, the reaction mixture was diluted with EtOAc. The organic layer was washed with 5% aqueous $NaHCO_3$ and brine, then dried over with anhydrous $MgSO_4$ and concentrated. The crude oil was purified by flash column chromatography to afford Example 20 (173 mg, 69% yield). Example 20 was characterized by the following data: $[\alpha]^{20}_D$+26.7° (c 1.00, DMSO); $^1$H NMR (400 MHz, DMSO-$d_6$) δ 10.03 (s, 1H), 8.03 (d, J=7.8 Hz, 2H), 7.91 (d, J=1.6 Hz, 1H), 7.28 (dd, J=1.7, 7.6 Hz, 2H), 7.18 (dd, J=7.4, 8.7 Hz, 1H), 4.49-4.38 (m, 2H), 2.50-2.48 (m, 6H), 1.54-1.43 (m, 6H), 0.89-0.84 (m, 24H); $^{13}$C NMR (75 MHz, DMSO-$d_6$) δ 172.12, 171.89, 139.69, 129.24, 114.79, 110.91, 52.20, 44.81, 26.11, 24.78, 23.43, 22.72, 22.68, 21.93.

Preparation of Example 21

Scheme U

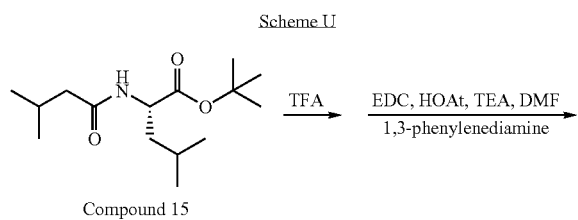

Compound 15

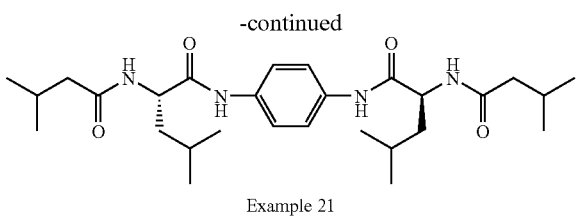

Example 21

Example 21 was prepared according to Scheme U above. Freshly distilled CH$_2$Cl$_2$ (10 mL) was added to a flask containing dried Compound 15 (270 mg, 1.0 mmol) under nitrogen atmosphere, followed by the addition of TFA (5 mL). The mixture was stirred at room temperature till Compound 15 was consumed. Then the reaction mixture was concentrated in vacuum and azeotroped with toluene 3 times to give the acid, which was used for next step without further purification.

Distilled DMF (10 mL) was added to a flask containing the acid (215 mg, 1 mmol) afforded in the last step under nitrogen atmosphere, followed by the additions of 1-hydroxy-7-azabenzotriazole (HOAt, 177 mg, 1.3 mmol), 1,4-phenylenediamine (54 mg, 0.5 mmol), triethylamine (0.14 mL, 1 mmol), and finally EDC.HCl (300 mg, 1.5 mmol). After stirred overnight, the reaction mixture was diluted with EtOAc. The organic layer was washed with 5% aqueous NaHCO$_3$ and brine, then dried over with anhydrous MgSO$_4$ and concentrated. The crude oil was purified by flash column chromatography to afford Example 21 (143 mg, 57% yield). Example 21 was characterized by the following data: [α]$^{20}$$_D$+16.6° (c 1.00, DMSO); $^1$H NMR (400 MHz, DMSO-d$_6$) δ9.99 (s, 2H), 8.05 (d, J=7.9 Hz, 2H), 7.52 (s, 4H), 4.56-4.38 (m, 2H), 2.55-2.40 (m, 6H), 1.65-1.44 (m, 6H), 0.91-0.86 (m, 24H); $^{13}$C NMR (400 MHz, DMSO-d$_6$) δ 172.07, 171.56, 134.93, 120.02, 52.08, 44.82, 26.10, 24.77, 23.46, 22.74, 22.67, 21.93;

Preparation of Example 22

Scheme V

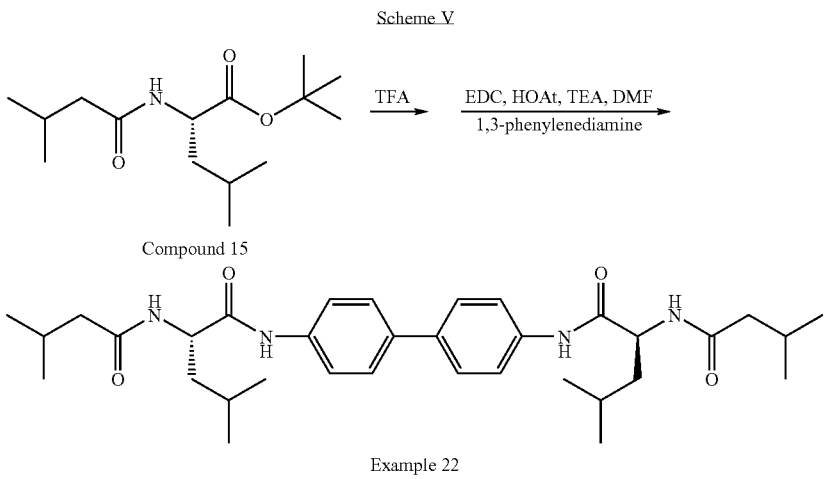

Compound 15

Example 22

Example 22 was prepared according to Scheme V above. Freshly distilled CH$_2$Cl$_2$ (10 mL) was added to a flask containing dried Compound 15 (270 mg, 1.0 mmol) under nitrogen atmosphere, followed by the addition of TFA (5 mL). The mixture was stirred at room temperature till Compound 15 was consumed. Then the reaction mixture was concentrated in vacuum and azeotroped with toluene 3 times to give the acid, which was used for next step without further purification.

Distilled DMF (10 mL) was added to a flask containing the acid (215 mg, 1 mmol) afforded in the last step under nitrogen atmosphere, followed by the additions of 1-hydroxy-7-azabenzotriazole (HOAt, 177 mg, 1.3 mmol), benzidine (92 mg, 0.5 mmol), triethylamine (0.14 mL, 1 mmol), and finally EDC.HCl (300 mg, 1.5 mmol). After stirred overnight, the reaction mixture was diluted with EtOAc. The organic layer was washed with 5% aqueous NaHCO$_3$ and brine, then dried over with anhydrous MgSO$_4$ and concentrated. The crude oil was purified by flash column chromatography to afford Example 22 (120 mg, 42% yield). Example 22 was characterized by the following data: [α]$^{20}$$_D$+24.2° (c 1.00, DMSO); $^1$H NMR (400 MHz, DMSO-d$_6$) δ 10.20 (s, 2H), 8.08 (d, J=7.8 Hz, 2H), 7.68 (d, J=8.5 Hz, 4H), 7.59 (d, J=8.4 Hz, 4H), 4.58-4.40 (dd, J=8.6, 13.3 Hz, 2H), 2.03-1.95 (m, 6H), 1.65-1.47 (m, 6H), 0.93-0.87 (m, 24H); $^{13}$C NMR (400 MHz, DMSO-d$_6$) δ 172.15, 171.92, 138.58, 134.93, 126.85, 120.04, 52.22, 44.82, 26.12, 24.80, 23.45, 22.73, 22.68, 21.96.

Preparation of Example 23

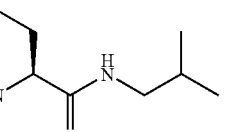

Example 23 was prepared according to Scheme W above. Freshly distilled CH$_2$Cl$_2$ (50 mL) was added to a flask containing Boc-Leu-OH (1.25 g, 5 mmol) under nitrogen atmosphere, followed by the addition of HOAt (0.88 g, 6.5 mmol), isobutylamine (1 mL, 10 mmol), and finally EDC.HCl (1.50 g, 7.5 mmol). After being stirred overnight, the reaction mixture was diluted with CH$_2$Cl$_2$. The organic layer was washed with 5% aqueous NaHCO$_3$ and brine, then dried over with anhydrous MgSO$_4$ and concentrated to afford Compound 8 as an oil (1.33 g, 93%), which was characterized by the following data: $^1$H NMR (400 MHz, CDCl$_3$) δ 6.25 (br, 1H), 4.91 (br, 1H), 4.16-3.98 (m, 1H), 3.08 (t, J=5.6 Hz, 2H), 1.80-1.66 (m, 4H), 1.44 (s, 9H), 0.94-0.90 (m, 12H); $^{13}$C NMR (75 MHz, CDCl$_3$) δ 172.46, 155.00, 53.15, 46.69, 41.04, 28.45, 28.27, 24.74, 22.84, 22.08, 19.99.

Freshly distilled CH$_2$Cl$_2$ (10 mL) was added to a flask containing dried Compound 8 (286 mg, 1.0 mmol) under nitrogen atmosphere, followed by the addition of TFA (5 mL). The reaction mixture was stirred at room temperature till Compound 8 was consumed. Then the reaction mixture was concentrated on a rotary evaporator and azeotroped with toluene 3 times to give the amine (TFA salt), which was used for next step without further purification.

Freshly distilled CH$_2$Cl$_2$ (10 mL) was added to a flask containing the amine afforded in the last step under nitrogen atmosphere, followed by the addition of DIPEA (0.16 mL, 1.0 mmol), and phenyl isocyanate (0.11 mL, 1 mmol). After stirred overnight, the reaction mixture was diluted with CH$_2$Cl$_2$. The organic layer was washed with 5% aqueous NaHCO$_3$ and brine, then dried over with anhydrous MgSO$_4$ and concentrated. The crude oil was purified by flash column chromatography to afford Example 23 (220 mg, 70%) as a white solid. Example 23 was characterized by the following data: $^1$H NMR (300 MHz, DMSO-d$_6$) δ 8.57 (s, 1H), 8.09 (t, J=5.6 Hz, 1H), 7.35 (d, J=8.0 Hz, 2H), 7.21 (t J=7.8 Hz, 2H), 6.88 (t, J=7.3 Hz, 1H), 6.29 (d, J=8.5 Hz, 1H), 4.34-4.26 (m, 1H), 2.97-2.80 (m, 2H), 1.71-1.58 (m, 2H), 1.44-1.38 (m, 2H), 0.92-0.82 (m, 12H); $^{13}$C NMR (75 MHz, DMSO-d$_6$) δ172.94, 155.04, 140.81, 129.12, 121.48, 117.87, 51.72, 46.40, 43.03, 28.44, 24.79, 23.39, 22.56, 20.51.

Preparation of Example 24

Example 24 was prepared according to Scheme X above. Freshly distilled CH$_2$Cl$_2$ (10 mL) was added to a flask containing dried Compound 8 (286 mg, 1.0 mmol) under nitrogen atmosphere, followed by the addition of TFA (5 mL). The reaction mixture was stirred at room temperature till Compound 8 was consumed. Then the reaction mixture was concentrated on a rotary evaporator and azeotroped with toluene 3 times to give the amine (TFA salt), which was used for next step without further purification.

Freshly distilled CH$_2$Cl$_2$ (10 mL) was added to a flask containing the amine afforded in the last step under nitrogen atmosphere, followed by the addition of DIPEA (0.16 mL, 1.0 mmol), and phenyl isothiocyanate (0.12 mL, 1 mmol). After stirred overnight, the reaction mixture was diluted with CH$_2$Cl$_2$. The organic layer was washed with 5% aqueous NaHCO$_3$ and brine, then dried over with anhydrous MgSO$_4$ and concentrated. The crude oil was purified by flash column chromatography to afford Example 24 (210 mg, 65%) as a white solid. Example 24 was characterized by the following data: $^1$H NMR (300 MHz, CDCl$_3$) δ 7.96 (s, 1H), 7.42 (d, J=7.5 Hz, 1H), 7.39 (d, J=7.8 Hz, 1H), 7.32-7.23 (m, 3H), 6.68 (d, J=8.3 Hz, 1H), 6.54 (br, 1H), 5.15-5.00 (m, 1H), 3.12-3.03 (m, 2H), 1.83-1.57 (m, 4H), 0.97-0.90 (m, 12H); $^{13}$C NMR (75 MHz, CDCl$_3$) δ180.57, 172.17, 136.51, 129.67, 126.85, 125.00, 56.97, 46.98, 40.73, 28.34, 24.85, 22.77, 22.55, 20, 05, 20.04;

Preparation of Example 25

Scheme Y

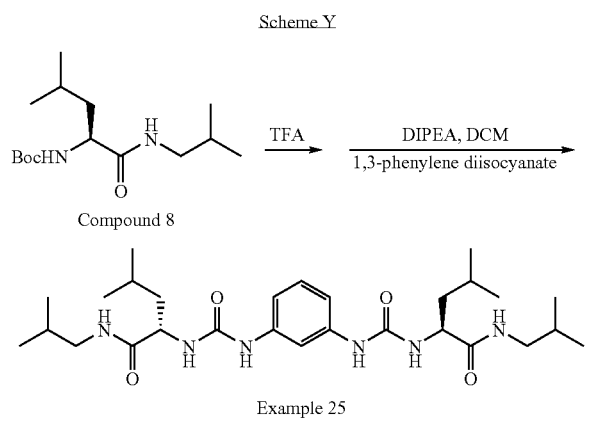

Example 25

Example 25 was prepared according to Scheme Y above. Freshly distilled CH$_2$Cl$_2$ (10 mL) was added to a flask containing dried Compound 8 (286 mg, 1.0 mmol) under nitrogen atmosphere, followed by the addition of TFA (5 mL). The reaction mixture was stirred at room temperature till Compound 8 was consumed. Then the reaction mixture was concentrated on a rotary evaporator and azeotroped with toluene 3 times to give the amine (TFA salt), which was used for next step without further purification.

Freshly distilled CH$_2$Cl$_2$ (10 mL) was added to a flask containing the amine afforded in the last step under nitrogen atmosphere, followed by the addition of DIPEA (0.16 mL, 1.0 mmol), and 1,3-phenylene diisocyanate (80 mg, 0.5 mmol). After stirred overnight, the reaction mixture was diluted with CH$_2$Cl$_2$. The organic layer was washed with 5% aqueous NaHCO$_3$ and brine, then dried over with anhydrous MgSO$_4$ and concentrated. The crude oil was purified by flash column chromatography to afford Example 25 (194 mg, 73%) as a white solid. Example 25 was characterized by the following data: $^1$H NMR (300 MHz, DMSO-d$_6$) δ 8.53 (s, 2H), 8.09 (t, J=5.6 Hz, 2H), 7.40 (s, 1H), 7.13-6.98 (m, 3H), 6.98-6.90 (m, 2H), 6.22 (d, J=8.5 Hz, 2H), 4.30-4.20 (m, 2H), 2.96-2.82 (m, 4H), 1.70-1.58 (m, 4H), 1.43-1.37 (m, 4H), 0.90 (d, J=2.2 Hz, 6H), 0.88 (d, J=2.1 Hz, 6H), 0.82 (d, J=6.7 Hz, 12H); $^{13}$C NMR (75 MHz, CDCl$_3$) δ 172.96, 154.97, 141.13, 129.30, 110.90, 107.00, 51.69, 46.40, 43.04, 28.44, 24.78, 23.41, 22.53, 20.52.

Preparation of Example 26

Scheme Z

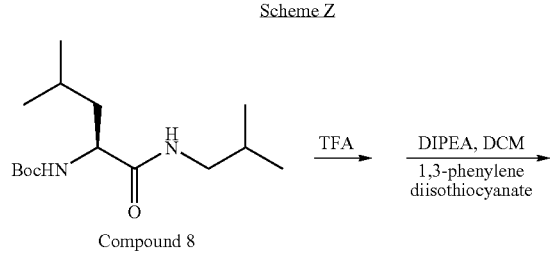

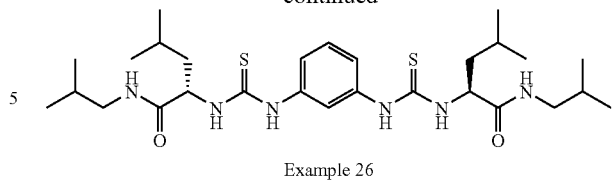

Example 26

Example 26 was prepared according to Scheme Z above. Freshly distilled CH$_2$Cl$_2$ (10 mL) was added to a flask containing dried Compound 8 (286 mg, 1.0 mmol) under nitrogen atmosphere, followed by the addition of TFA (5 mL). The reaction mixture was stirred at room temperature till Compound 8 was consumed. Then the reaction mixture was concentrated on a rotary evaporator and azeotroped with toluene 3 times to give the amine (TFA salt), which was used for next step without further purification.

Freshly distilled CH$_2$Cl$_2$ (10 mL) was added to a flask containing the amine afforded in the last step under nitrogen atmosphere, followed by the addition of DIPEA (0.16 mL, 1.0 mmol), and 1,3-phenylene diisothiocyanate (96 mg, 0.5 mmol). After stirred overnight, the reaction mixture was diluted with CH$_2$C$_2$. The organic layer was washed with 5% aqueous NaHCO$_3$ and brine, then dried over with anhydrous MgSO$_4$ and concentrated. The crude oil was purified by flash column chromatography to afford Example 26 (220 mg, 78%) as a white solid. Example 26 was characterized by the following data: $^1$H NMR (300 MHz, CDCl$_3$) δ 8.47 (s, 2H), 7.63 (br, 2H), 7.35-7.28 (m, 1H), 7.23-7.13 (m, 3H), 6.71 (t, J=5.5 Hz, 2H), 5.02-4.95 (m, 2H), 3.11-2.98 (m, 4H), 1.82-1.66 (m, 8H), 0.96-0.84 (m, 24H); $^{13}$C NMR (100 MHz, CDCl$_3$) δ 180.63, 173.21, 138.02, 129.46, 121.26, 120.56, 57.17, 47.12, 41.01, 28.38, 24.86, 22.93, 22.31, 20.18, 20.14.

Preparation of Example 27

Scheme AA

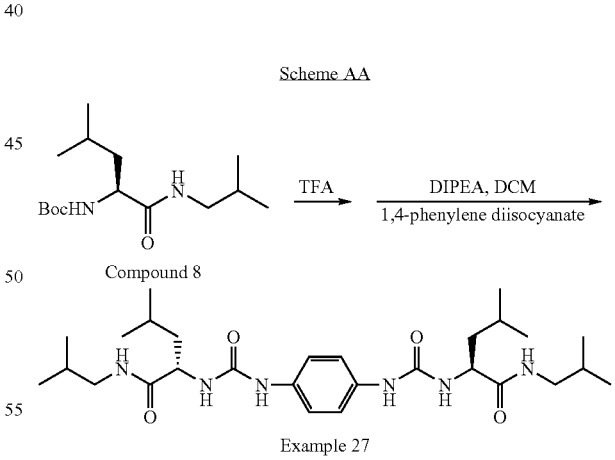

Example 27

Example 27 was prepared according to Scheme AA above. Freshly distilled CH$_2$Cl$_2$ (10 mL) was added to a flask containing dried Compound 8 (286 mg, 1.0 mmol) under nitrogen atmosphere, followed by the addition of TFA (5 mL). The reaction mixture was stirred at room temperature till Compound 8 was consumed. Then the reaction mixture was concentrated on a rotary evaporator and azeotroped with toluene 3 times to give the amine (TFA salt), which was used for next step without further purification.

Freshly distilled CH$_2$Cl$_2$ (10 mL) was added to a flask containing the amine afforded in the last step under nitrogen atmosphere, followed by the addition of DIPEA (0.16 mL, 1.0 mmol), and 1,4-phenylene diisocyanate (80 mg, 0.5 mmol). After stirred overnight, the reaction mixture was diluted with CH$_2$Cl$_2$. The organic layer was washed with 5% aqueous NaHCO$_3$ and brine, then dried over with anhydrous MgSO$_4$ and concentrated. The crude oil was purified by flash column chromatography to afford Example 27 (200 mg, 76%) as a white solid. Example 27 was characterized by the following data: $^1$H NMR (300 MHz, DMSO-d$_6$) δ 8.38 (s, 2H), 8.07 (t, J=5.5 Hz, 2H), 7.20 (s, 4H), 6.18 (d, J=8.4 Hz, 2H), 4.28-4.15 (m, 2 μl), 2.98-2.90 (m, 2H), 2.86-2.81 (m, 2H), 1.70-1.58 (m, 4H), 1.43-1.37 (m, 4H), 0.90-0.88 (m, 12H), 0.82 (d, J=6.6 Hz, 12H); $^{13}$C NMR (75 MHz, DMSO-d$_6$) δ 173.07, 155.20, 134.63, 118.66, 51.76, 46.39, 42.99, 28.43, 24.77, 23.39, 22.54, 20.50.

Preparation of Example 28

Scheme AB

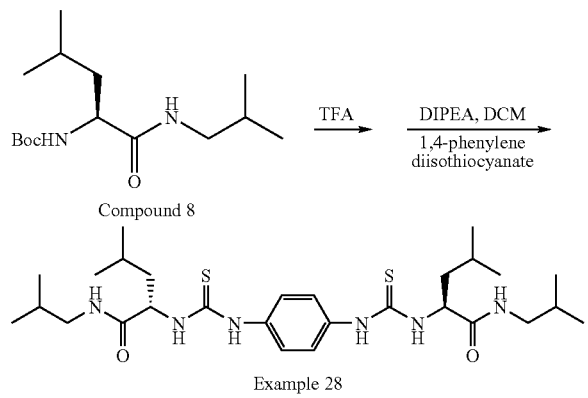

Example 28 was prepared according to Scheme AB above. Freshly distilled CH$_2$Cl$_2$ (10 mL) was added to a flask containing dried Compound 8 (286 mg, 1.0 mmol) under nitrogen atmosphere, followed by the addition of TFA (5 mL). The reaction mixture was stirred at room temperature till Compound 8 was consumed. Then the reaction mixture was concentrated on a rotary evaporator and azeotroped with toluene 3 times to give the amine (TEA salt), which was used for next step without further purification.

Freshly distilled CH$_2$Cl$_2$ (10 mL) was added to a flask containing the amine afforded in the last step under nitrogen atmosphere, followed by the addition of DIPEA (0.16 mL, 1.0 mmol), and 1,4-phenylene diisocyanate (96 mg, 0.5 mmol). After stirred overnight, the reaction mixture was diluted with CH$_2$Cl$_2$. The organic layer was washed with 5% aqueous NaHCO$_3$ and brine, then dried over with anhydrous MgSO$_4$ and concentrated. The crude oil was purified by flash column chromatography to afford Example 28 (254 mg, 90%) as a yellow solid. Example 28 was characterized by the following data: $^1$H NMR (400 MHz, CDCl$_3$) δ 8.50 (s, 2H), 7.65 (br, 2H), 7.09 (s, 4H), 6.82 (br, 2H), 5.02-4.95 (m, 2H), 3.15-3.09 (m, 2H), 3.04-2.99 (m, 2H), 1.80-1.67 (m, 8H), 0.98 (d, J=5.9 Hz, 12H), 0.90-0.88 (m, 12H); $^{13}$C NMR (100 MHz, DMSO-d$_6$) δ 180.93, 173.53, 135.23, 125.25, 57.00, 47.12, 41.18, 28.43, 24.87, 22.92, 22.29, 20.17, 20.11.

Preparation of Example 29

Scheme AC

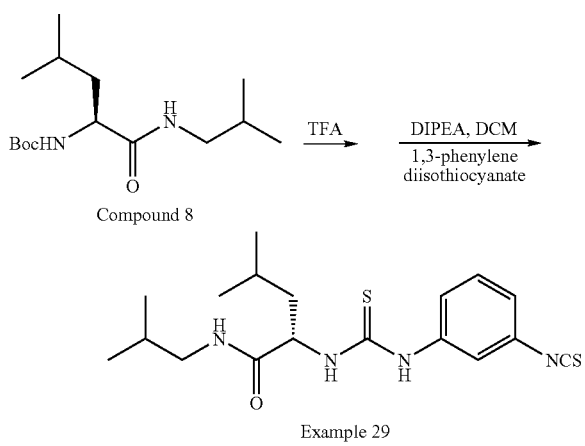

Example 29 was prepared according to Scheme AC above. Freshly distilled CH$_2$Cl$_2$ (10 mL) was added to a flask containing dried Compound 8 (286 mg, 1.0 mmol) under nitrogen atmosphere, followed by the addition of TFA (5 mL). The reaction mixture was stirred at room temperature till Compound 8 was consumed. Then the reaction mixture was concentrated on a rotary evaporator and azeotroped with toluene 3 times to give the amine (TFA salt), which was used for next step without further purification.

Freshly distilled CH$_2$Cl$_2$ (10 mL) was added to a flask containing the amine afforded in the last step under nitrogen atmosphere, followed by the addition of DIPEA (0.16 mL, 1.0 mmol), and 1,4-phenylene diisocyanate (192 mg, 1 mmol). After stirred overnight, the reaction mixture was diluted with CH$_2$Cl$_2$. The organic layer was washed with 5% aqueous NaHCO$_3$ and brine, then dried over with anhydrous MgSO$_4$ and concentrated. The crude oil was purified by flash column chromatography to afford Example 29 (320 mg, 85%) as a foamy solid. Example 29 was characterized by the following data: $^1$H NMR (300 MHz, CDCl$_3$) δ 8.56 (s, 1H), 7.92 (d, J=6.3 Hz, 1H), 7.49 (s, 1H), 7.40-7.19 (m, 2H), 7.00-6.97 (m, 1H), 6.44 (t, J=5.8 Hz, 1H), 5.05-4.98 (m, 1H), 3.12-3.06 (m, 2H), 1.81-1.70 (m, 4H), 1.02-0.98 (m, 6H), 0.92-0.88 (m, 6H); $^{13}$C NMR (100 MHz, CDCl$_3$) δ 181.06, 173.89, 139.31, 135.81, 131.51, 129.68, 122.88, 122.66, 121.25, 56.94, 47.32, 41.21, 28.38, 24.88, 22.86, 22.34, 20.09, 20.06.

Preparation of Example 30

Scheme AD

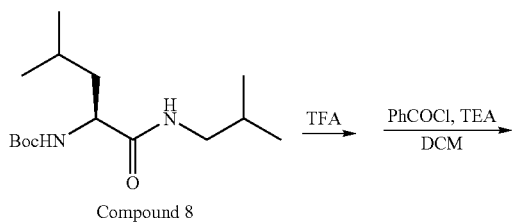

69
-continued

Example 30

Example 30 was prepared according to Scheme AD above. Freshly distilled CH$_2$Cl$_2$ (10 mL) was added to a flask containing dried Compound 8 (286 mg, 1.0 mmol) under nitrogen atmosphere, followed by the addition of TFA (5 mL). The reaction mixture was stirred at room temperature till Compound 8 was consumed. Then the reaction mixture was concentrated on a rotary evaporator and azeotroped with toluene 3 times to give the amine (TFA salt), which was used for next step without further purification.

Freshly distilled CH$_2$Cl$_2$ (10 mL) was added to a flask containing the amine afforded in the last step under nitrogen atmosphere, followed by the addition of TEA (0.42 ml, 3.0 mmol), and benzoyl chloride (0.12 mL, 1 mmol). After stirred overnight, the reaction mixture was diluted with CH$_2$Cl$_2$. The organic layer was washed with 5% aqueous NaHCO$_3$ and brine, then dried over with anhydrous MgSO$_4$ and concentrated. The crude oil was purified by flash column chromatography to afford Example 30 (210 mg, 70%) as a white solid. Example 30 was characterized by the following data: $[\alpha]^{20}_D$ -57.3° (c 1.00, CHCl$_3$); $^1$H NMR (400 MHz, CDCl$_3$) δ 7.79-7.77 (m, 2H), 7.52-7.48 (m, 1H), 7.43-7.39 (m, 2H), 6.88 (br, 1H), 6.60 (br, 1H), 4.73-4.67 (m, 1H), 3.10-3.03 (m, 2H), 1.81-1.71 (m, 4H), 0.99-0.97 (m, 6H), 0.88 (d, J=6.7 Hz, 6H); $^{13}$C NMR (100 MHz, CDCl$_3$) δ 172.28, 167.48, 133.88, 131.64, 128.47, 127.14, 52.31, 46.86, 41.26, 28.40, 24.95, 22.85, 22.41, 20.05; LRMS (EI, 20 eV) m/z 290 (M$^+$, 1), 105 (100); HRMS (EI) for C$_{17}$H$_{26}$N$_2$O$_2$ (M$^+$): calculated 290.1994. found 290.1991.

Preparation of Example 31

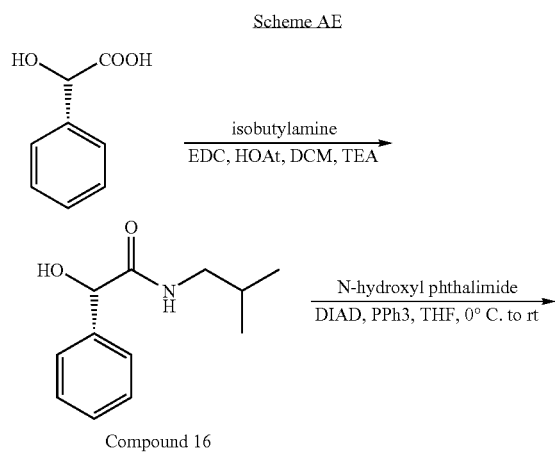

Scheme AE

70
-continued

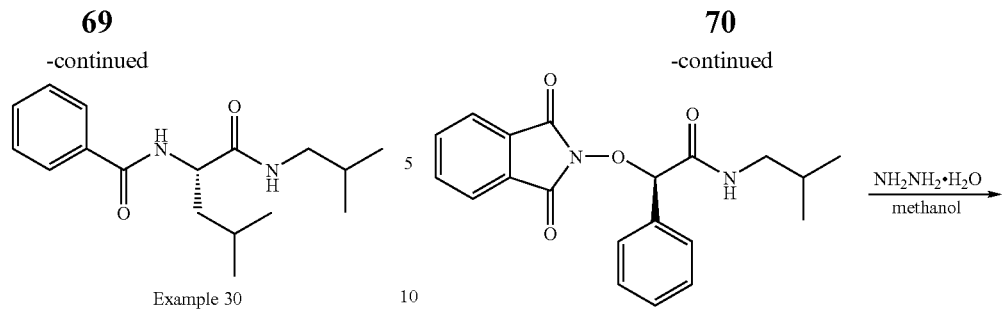

Example 31

Example 31 was prepared according to Scheme AE above. Freshly distilled CH$_2$Cl$_2$ (50 mL) was added to a flask containing L-(+)-Mandelic acid (1.52 g, 10 mmol) under nitrogen atmosphere, followed by the addition of HOAt (1.633 g, 12 mmol), isobutylamine (1.2 mL, 12 mmol), and finally EDC.HCl (2.60 g, 13 mmol). After being stirred overnight, the reaction mixture was diluted with CH$_2$Cl$_2$. The organic layer was washed with 5% aqueous NaHCO$_3$ and brine, then dried over with anhydrous MgSO$_4$ and concentrated to afford Compound 16 as an oil (1.94 g, 94%).

Compound 16 (1.22 g, 5.9 mmol), N-hydroxy phthalimide (1.01 g, 6.2 mmol) and PPh$_3$ (1.73 g, 6.5 mmol) were dissolved in dry THF (100 mL) in a 250 ml dry round bottom flask. Then DIAD (diisopropyl azodicarboxylate, 1.24 mL, 6.2 mmol) was added dropwisely using a syringe under ice bath. After stirred for 1.5 hours, the solvent was removed on a rotary evaporator. The residue was dissolved in ethyl acetate and washed with water and brine, then dried over with anhydrous MgSO$_4$ and concentrated. The crude oil was purified by flash column chromatography to afford compound 17 (1.5 g, 72%) as a white solid.

To a solution of Compound 17 (1.5 g, 4.25 mmol) in CH$_3$OH (40 mL) was added NH$_2$NH$_2$.H$_2$O (0.4 mL, 12.8 mmol). A white precipitate appeared after 1 hour. After stirred at room temperature for 2.5 hours, the reaction mixture was concentrated under vacuo. The residue was dissolved in CH$_2$Cl$_2$ and was washed with 5% NaHCO$_3$ twice and then with brine. The organic layer was dried over anhydrous Na$_2$SO$_4$ and concentrated to provide a mixture of Compound 18 and phthahydroazide as a colorless oil. This mixture was immediately used in the next step without further purification.

Freshly distilled CH$_2$Cl$_2$ (50 mL) was added to a flask containing dried Compound 18 under nitrogen atmosphere, followed by the addition of HOAt (752 mg, 5.13 mmol), isophthalic acid (353 mg, 2.13 mmol), triethylamine (0.6 mL, 4.3 mmol), and finally EDC-HCl (1.27 g, 6.38 mmol). After stirred overnight, the reaction mixture was diluted with CH$_2$Cl$_2$. The organic layer was washed with 5% aqueous NaHCO$_3$ and brine, then dried over anhydrous MgSO$_4$ and concentrated. The crude oil was purified by flash column chromatography to afford Example 31 (734 mg, 60% yield) as a white solid. Example 31 was characterized by the following data: [α]$^{20}_D$–58.2° (c 1.00, DMSO); $^1$H NMR (400 MHz, DMSO-d$_6$) δ 12.19 (s, 2H), 8.47 (br, 2H), 8.16 (s, 1H), 7.89 (d, J=7.4 Hz, 2H), 7.60-7.55 (m, 1H), 7.49 (d, J=7.2 Hz, 4H), 7.42-7.39 (m, 6H), 5.43 (s, 2H), 3.02-2.89 (m, 4H), 1.74-1.67 (m, 2H), 0.80-0.78 (m, 12H); $^{13}$C NMR (75 MHz, DMSO-d$_6$) δ 168.9, 165.2, 136.4, 132.4, 130.8, 129.2, 129.1, 128.7, 128.2, 126.9, 86.1, 46.3, 28.5, 20.4; LRMS (FAB) m/z 575 (M$^+$+H); HRMS (FAB) for C$_{32}$H$_{39}$N$_4$O$_6$ (M$^+$+H): calculated 575.2791. found 575.2871.

Preparation of Example 32

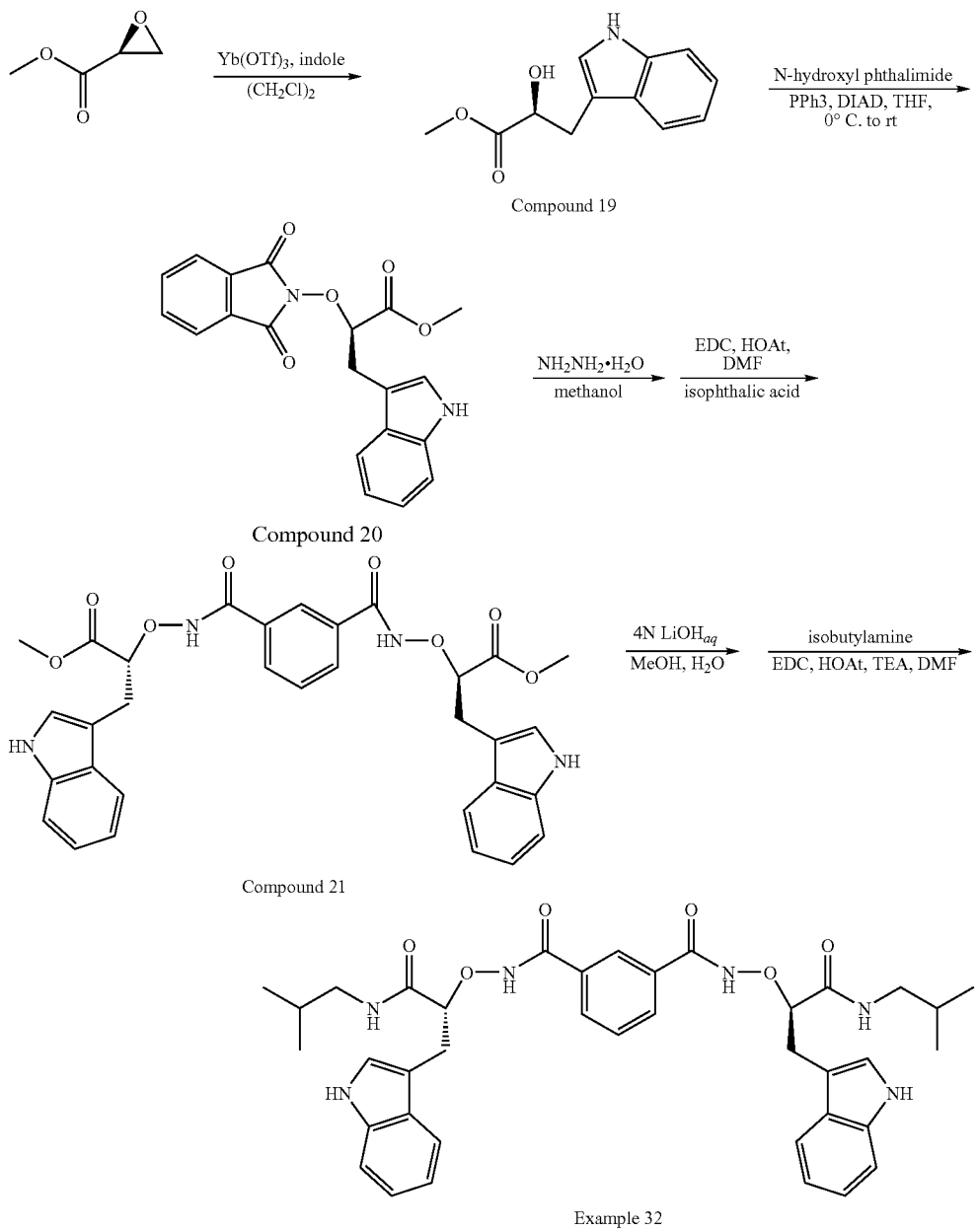

Example 32 was prepared according to Scheme AF above. Compound 19 was synthesized according to the procedures described in Satoshi mura et al., *Org. Lett*, 2005, 7, 941-943. Compound 19 (2.0 g, 9.1 mmol), N-hydroxy phthalimide (1.64 g, 10.1 mmol) and PPh$_3$ (2.9 g, 11 mmol) were dissolved in dry THF (100 mL) in a 250 mL dry round bottom flask. Then DIAD (diisopropyl azodicarboxylate, 2 mL, 10.1 mmol) was added dropwisely using a syringe in an ice bath. After stirred for 1.5 hours, the solvent was removed on a rotary evaporator. The residue was dissolved in ethyl acetate and washed with water and brine, then dried over with anhydrous MgSO$_4$ and concentrated. The crude oil was purified by flash column chromatography to afford compound 20 (2.18 g, 67% yield) as a white solid. Compound 20 was characterized by the following data: $[\alpha]^{20}{}_D$ –12.4° (c 1.00, acetone); $^1$H NMR (400 MHz, CDCl$_3$) δ 8.17 (s, 1H), 7.86-7.78 (m, 2H), 7.78-7.70 (m, 2H), 7.64 (d, J=7.7 Hz, 1H), 7.35-7.29 (m, 2H), 7.20-7.11 (m, 2H), 5.07 (t, J=6.8 Hz, 1H), 3.67 (s, 3H), 3.59-3.47 (m, 2H); $^{13}$C NMR (75 MHz, CDCl$_3$) δ 169.50, 163.19, 136.02, 134.57, 128.81, 127.31, 123.65, 123.49, 122.09, 119.58, 118.50, 111.13, 108.77, 85.30, 52.46, 26.70; LRMS (EI, 20 eV) m/z 364 (M$^+$, 10), 201 (100); HRMS (EI) for $C_{20}H_{16}N_2O_5$ (M$^+$): calculated 364.1059. found 364.1056.

To a solution of Compound 20 (1.68 g, 4.6 mmol) in CH$_3$OH (40 mL) was added NH$_2$NH$_2$.H$_2$O (0.3 mL, 5.1 mmol). A white precipitate appeared after 1 hour. After stirred at room temperature for 2.5 hours, the reaction mixture was concentrated on a rotary evaporator. The residue was dissolved in CH$_2$Cl$_2$ and washed with 5% aqueous NaHCO$_3$ and brine. The organic layer was dried over with anhydrous Na$_2$SO$_4$ and concentrated to provide a mixture of amine and phthahydroazide as solid. This mixture was immediately used in the next step without further purification.

Freshly distilled DMF (50 mL) was added to a flask containing the mixture got in the last step under Argon atmosphere, followed by the addition of HOAt (817 mg, 6 mmol), isophthalic acid (382 mg, 2.3 mmol), and finally EDC-HCl (1.38 g, 6.9 mmol). After stirred overnight, the reaction mixture was diluted with EtOAc. The organic layer was washed with 5% aqueous NaHCO$_3$ and brine, then dried over with anhydrous MgSO$_4$ and concentrated. The crude oil was purified by flash column chromatography to afford compound 21 (1.18 g, 86%) as a white solid. compound 21 was characterized by the following data: $[\alpha]^{20}{}_D$ 24.4° (c 1.00, acetone); $^1$H NMR (400 MHz, acetone-d$_6$) δ 10.10 (s, 2H), 8.23 (s, 1H), 7.98-7.96 (m, 2H), 7.60-7.54 (m, 3H), 7.43-7.37 (m, 4H), 7.09-7.02 (m, 4H), 4.96 (t, J=6.3 Hz, 2H), 3.61 (s, 6H), 3.34 (d, J=6.3 Hz, 4H); $^{13}$C NMR (100 MHz, acetone-d$_6$) δ 171.04, 136.57, 135.02, 132.44, 130.15, 128.75, 127.73, 125.90, 123.94, 123.78, 123.62, 121.21, 118.68, 118.28, 111.25, 110.29, 109.68, 108.95, 83.52, 51.23, 26.89; LRMS (FAB) m/z 599 (M$^+$+H); HRMS (FAB) for $C_{32}H_{30}N_4O_8$ (M$^+$): calculated 598.2064. found 598.2069.

Compound 21 (490 mg, 0.82 mmol) was dissolved in THF (6 mL) in an ice bath. Aqueous LiOH (140 mg dissolved in 3 mL water) was added dropwisely into the above solution and the reaction mixture was stirred at rt for 1.5 hours. After removal of THF on a rotary evaporator. The residue was diluted with water and extracted with EtOAc to remove the organic impurity. Then the aqueous phase was acidified with 1M HCl to pH about 4 and extracted with EtOAc. Finally the organic layer was combined and concentrated to afford the foamy acid (400 mg, 86% yield) which directly used in the next coupling reaction.

DMF (10 mL) was added to a flask containing the acid above (400 mg, 0.7 mmol) under nitrogen atmosphere, followed by the addition of HOAt (124 mg, 0.91 mmol), isobutylamine (0.2 mL, 2.1 mmol), and finally EDC.HCl (220 mg, 1.1 mmol). After being stirred overnight, the reaction mixture was diluted with EtOAc. The organic layer was washed with 5% aqueous NaHCO$_3$ and brine, then dried over with anhydrous MgSO$_4$ and concentrated. The crude oil was purified by flash column chromatography to afford Example 32 (130 mg, 28% yield). Example 32 was characterized by the following data: $[\alpha]^{20}{}_D$+64.8° (c 1.00, CHCl$_3$); $^1$H NMR (300 MHz, CDCl$_3$) δ 9.48 (s, 2H), 8.26 (s, 2H), 8.08 (t, J=5.7 Hz, 2H), 7.60 (d, J=7.7 Hz, 2H), 7.52 (d, J=7.7 Hz, 2H), 7.30-7.25 (m, 2H), 7.17-7.15 (m, 2H), 7.05-6.94 (m, 6H), 4.47 (dd, J=9.2, 3.1 Hz, 2H), 3.37-3.31 (m, 2H), 3.14-2.93 (m, 6H), 1.73-1.64 (m, 2H), 0.82-0.77 (m, 12H); $^{13}$C NMR (75 MHz, CDCl$_3$) δ 170.88, 165.88, 135.99, 131.44, 130.80, 129.29, 127.18, 123.99, 123.49, 122.08, 119.59, 118.66, 111.28, 110.82, 87.37, 46.73, 28.25, 28.09, 19.98; LRMS (FAB) m/z 681 (M$^+$+H); HRMS (FAB) for $C_{38}H_{44}N_6O_6$ (M$^+$): calculated 680.3322. found 680.3239.

Preparation of Example 33

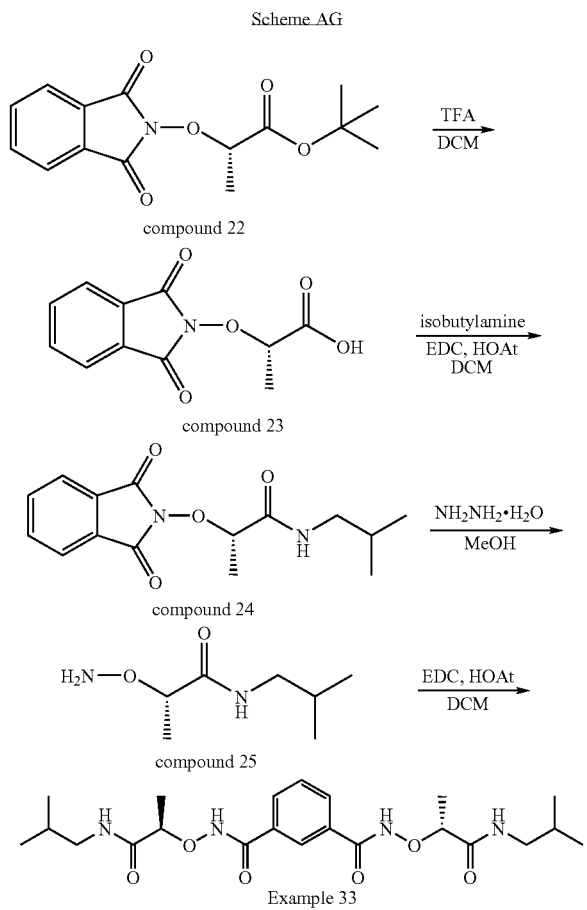

Example 33 was prepared according to Scheme AG above. Compound 22 was synthesized according to the procedures described in Yang et al., *J. Org. Chem.*, 2001, 66, 7303-7312. Freshly distilled CH$_2$Cl$_2$ (10 mL) was added to a flask containing dried Compound 22 (880 mg, 3.0 mmol) under nitrogen atmosphere, followed by the addition of TFA (5 mL). The mixture was stirred at room temperature till Compound 22 was consumed. Then the reaction mixture was concentrated on a rotary evaporator and azeotroped with toluene 3 times to give the compound 23, which was used for next step without further purification.

Freshly distilled CH$_2$Cl$_2$ (50 mL) was added to a flask containing compound 23 under nitrogen atmosphere, followed by the addition of HOAt (0.53 g, 3.9 mmol), isobutylamine (0.3 mL, 3 mmol), and finally EDC.HCl (900 mg, 4.5 mmol). After being stirred overnight, the reaction mixture was diluted with $CH_2Cl_2$. The organic layer was washed with 5% aqueous $NaHCO_3$ and brine, then dried over with anhydrous $MgSO_4$ and concentrated to afford Compound 24 as an oil (850 mg, 93%), To a solution of Compound 24 (850 mg, 3 mmol) in $CH_3OH$ (40 ml) was added $NH_2NH_2$—$H_2O$ (0.23 mL, 3.8 mmol). A white precipitate appeared after 1 hour. After stirred at room temperature for 2.5 hours, the reaction mixture was concentrated on a rotary evaporator. The residue was dissolved in $CH_2Cl_2$ and washed with 5% aqueous $NaHCO_3$ and brine. The organic layer was dried over with anhydrous $Na_2SO_4$ and concentrated to provide a mixture of compound 25 and phthahydroazide as solid. This mixture was immediately used in the next step without further purification Freshly distilled DMF (30 mL) was added to a flask containing the mixture got in the last step under nitrogen atmosphere, followed by the addition of HOAt (530 mg, 3.9 mmol), isophthalic acid (250 mg, 1.5 mmol), and finally EDC-HCl (900 mg, 4.5 mmol). After stirred overnight, the reaction mixture was diluted with EtOAc. The organic layer was washed with 5% aqueous $NaHCO_3$ and brine and then dried over with anhydrous $MgSO_4$ and concentrated. The crude oil was purified by flash column chromatography to afford Example 33 (350 mg, 4 steps: 86%) as a white solid. Example 33 was characterized by the following data: $[\alpha]^{20}_D$+44.1° (c 1.00, $CHCl_3$); $^1H$ NMR (300 MHz, $CDCl_3$) δ 10.98 (s, 2H), 8.20-8.17 (m, 3H), 8.06 (d, J=7.8 Hz, 2H), 7.58 (t, J=7.8 Hz, 1H), 4.46 (m, 2H), 3.05-2.88 (m, 4H), 1.78-1.69 (m, 2H), 1.44 (d, J=6.9 Hz, 6H), 0.82 (t, J=6.5 Hz, 12H); $^{13}C$ NMR (75 MHz, $CHCl_3$) δ 172.26, 166.19, 131.81, 131.29, 129.50, 125.03, 82.72, 46.67, 28.26, 19.95, 17.59; LRMS (EI, 20 eV) m/z 451 ($M^+$+1, 17), 148 (100); HRMS (EI) for $C_{22}H_{34}N_4O_6$ ($M^+$): calculated 450.2478. found 450.2478.

Preparation of Examples 34 and 35

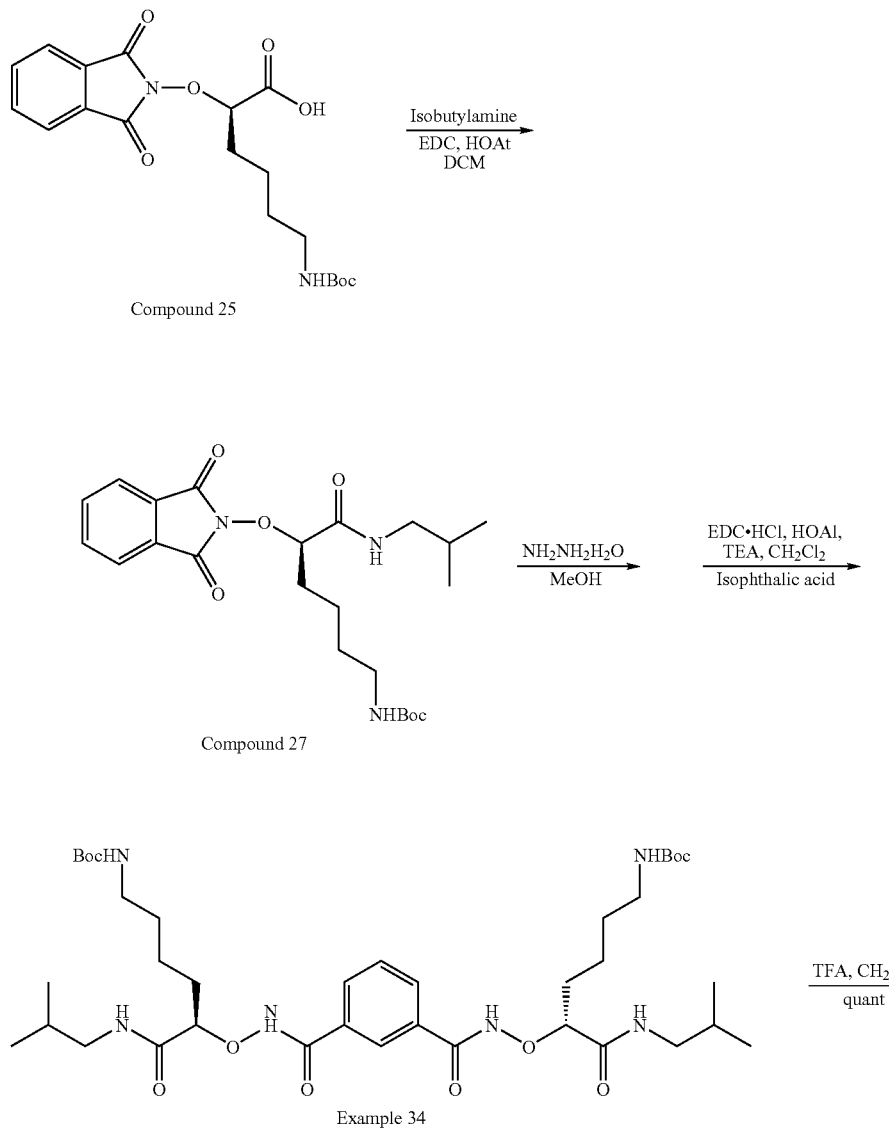

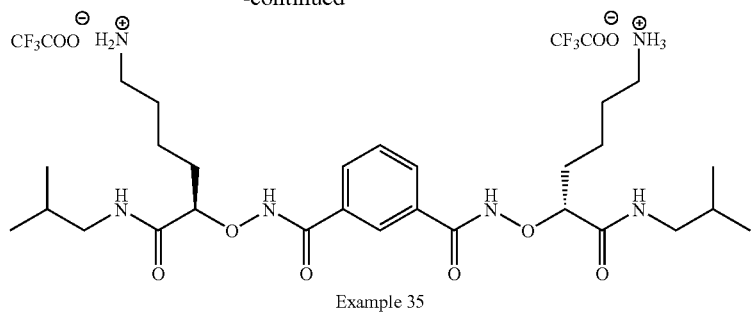

Example 35

Example 34 and 35 were prepared according to Scheme AH above Compound 26 was synthesized according to the procedures described in Yoon et al., *J. Org. Chem*, 2000, 65, 7667-7675. Freshly distilled $CH_2Cl_2$ (50 mL) was added to a flask containing compound 26 (1.18 g, 3 mmol) under nitrogen atmosphere, followed by the addition of HOAt (0.53 g, 3.9 mmol), isobutylamine (0.3 mL, 3 mmol), and finally EDC.HCl (900 mg, 4.5 mmol). After being stirred overnight, the reaction mixture was diluted with $CH_2Cl_2$. The organic layer was washed with 5% aqueous $NaHCO_3$ and brine and then dried over with anhydrous $MgSO_4$ and concentrated to afford Compound 27 as an oil (1.2 g, 93%).

To a solution of Compound 27 (1.2 g, 2.7 mmol) in $CH_3OH$ (40 mL) was added $NH_2NH_2 \cdot H_2O$ (0.58 mL, 9.6 mmol). A white precipitate appeared after 1 hour. After stirred at room temperature for 2.5 hours, the reaction mixture was concentrated on a rotary evaporator. The residue was dissolved in $CH_2Cl_2$ and washed with 5% aqueous $NaHCO_3$ and brine. The organic layer was dried over with anhydrous $Na_2SO_4$ and concentrated to provide a mixture of amine and phthahydroazide as solid. This mixture was immediately used in the next step without further purification.

Freshly distilled $CH_2Cl_2$ (30 mL) was added to a flask containing the mixture got in the last step under nitrogen atmosphere, followed by the addition of HOAt (530 mg, 3.9 mmol), isophthalic acid (225 mg, 1.35 mmol), and finally EDC.HCl (900 mg, 4.5 mmol). After stirred overnight, the reaction mixture was diluted with EtOAc. The organic layer was washed with 5% aqueous $NaHCO_3$ and brine and then dried over with anhydrous $MgSO_4$ and concentrated. The crude oil was purified by flash column chromatography to afford Example 34 (688 mg, 4 steps: 30%) as a white solid. Example 34 was characterized by the following data: $^1H$ NMR (300 MHz, $CDCl_3$) δ 11.04 (hr, 2H), 8.26 (m, 3H), 8.05 (d, J=7.7 Hz, 2H), 7.61-7.50 (m, 1H), 4.98 (br, 2H), 4.40-4.32 (m, 2H), 3.16-2.96 (m, 4H), 1.94-1.75 (m, 6H), 1.52-1.45 (m, 8H), 1.36 (s, 18H), 0.92-0.85 (m, 12H); $^{13}C$ NMR (75 MHz, $CHCl_3$) δ 170.70, 166.28, 156.89, 131.56, 131.40, 129.27, 125.63, 86.42, 79.58, 46.64, 39.85, 30.59, 29.69, 28.36, 28.09, 21.80, 20.07.

Example 34 (270 mg, 0.35 mmol) was dissolved in $CH_2Cl_2$ (2 mL). In an ice bath, TFA (1 mL) was added dropwisely. 4 hours later, the reaction mixture was concentrated on a rotary evaporator and azeotroped with toluene 3 times to give the Example 35. Example 35 was characterized by the following data: $^1H$ NMR (400 MHz, $D_2O$) δ 7.94 (d, J=1.6 Hz, 1H), 7.87 (d, J=7.8 Hz, 1H), 7.86 (d, J=7.9 Hz, 1H), 7.60 (t, J=7.9 Hz, 1H), 4.49 (dd, J=12.6, 6.4 Hz, 2H), 3.12-2.98 (m, 8H), 1.90-1.86 (m, 4H), 1.77-1.70 (m, 6H), 1.57-1.53 (m, 4H), 0.84-0.80 (m, 12H); $^{13}C$ NMR (75 MHz, $D_2O$) 5172.43, 167.76, 131.25, 131.18, 129.63, 126.16, 85.36, 72.09, 46.60, 39.12, 30.16, 27.81, 26.43, 21.29, 19.23, 19.20; LRMS (FAB) m/z 565 (M$^+$+H); HRMS (FAB) for $C_{28}H_{48}N_6O_6$ (M$^+$): calculated 564.3635. found 564.3598.

Preparation of Example 36

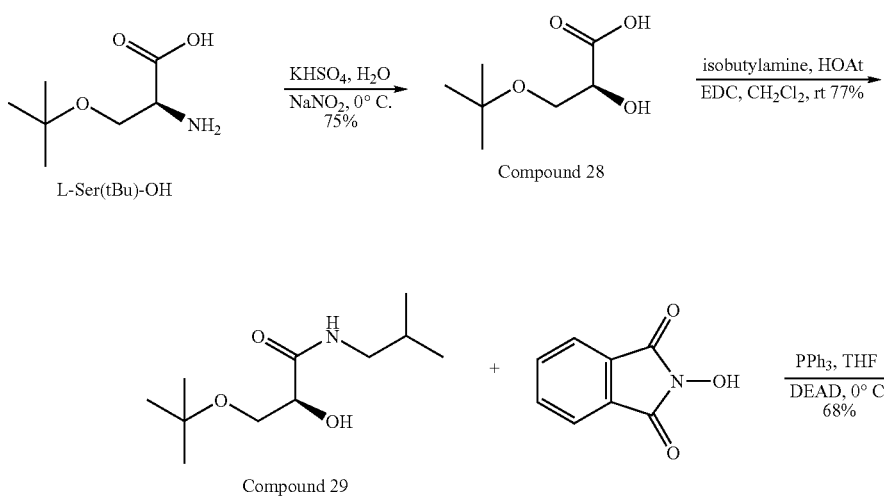

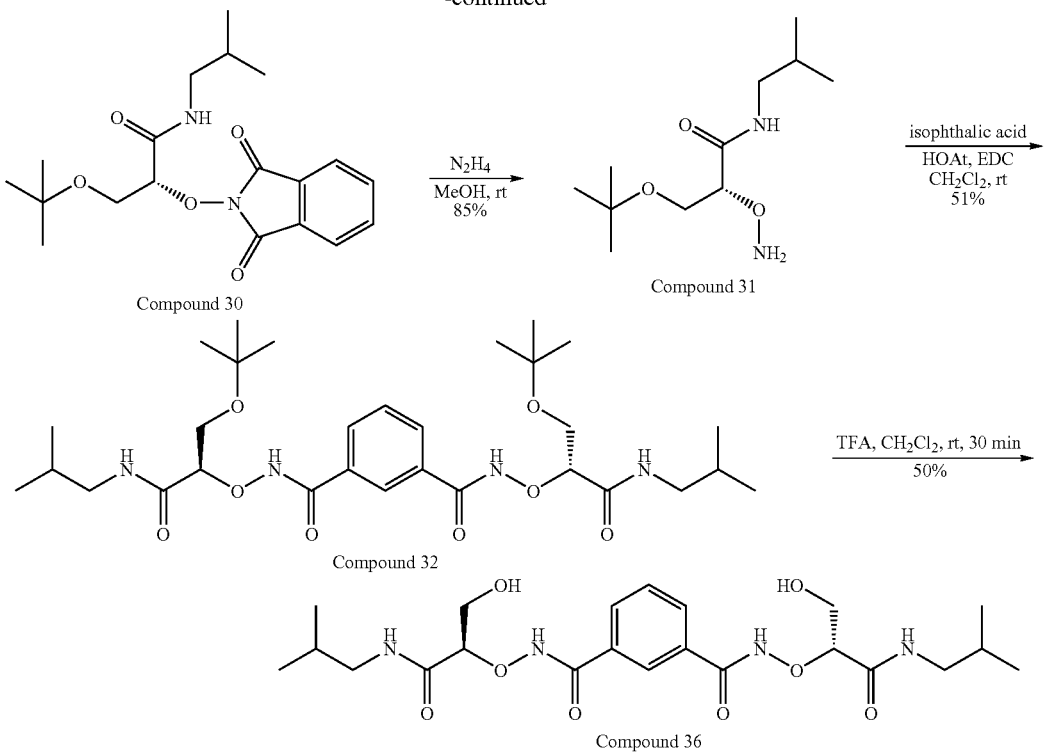

Example 36 was prepared according to Scheme AI. L-Ser (tBu)-OH (1.61 g, 10 mmol) was dissolved in aqueous KHSO$_4$ solution (2.04 g in 40 ml water). The solution was cooled to 0° C., followed by addition of aqueous NaNO$_2$ solution (1.04 g in 20 mL water) dropwisely during 30 minutes. Then stirring was continued overnight at room temperature. The solution was extracted with ethyl acetate 3 times and the combined organic phase was dried and concentrated to afford compound 28 (1.21 g, 75% yield) as a yellow oil, which can be used directly in the next step without further purification.

Compound 28 and isobutylamine (1.11 mL, 11.2 mmol) were dissolved in 50 mL CH$_2$Cl$_2$, followed by addition of HOAt (1.12 g, 8.25 mmol) and EDC.HCl (1.80 g, 9 mmol) successively. The solution was stirring for 5 hours, then diluted with CH$_2$Cl$_2$ and washed successively with 5% KHSO$_4$ (2 times), 10% NaHCO$_3$ (2 times), and dried with Na$_2$SO$_4$. After concentration, the residue was purified by flash column chromatography using ethyl acetate/hexane as eluent to afford compound 29 (1.25 g, 77% yield) as colorless oil. [α]$^{20}_D$–13.8° (c 1.00, CHCl$_3$); $^1$H NMR (400 MHz, CDCl$_3$) δ6.92 (br, 1H), 4.14-4.10 (m, 1H), 3.64 (d, J=4.2 Hz, 1H), 3.60-3.58 (m, 2H), 3.17-3.08 (m, 2H), 1.80 (sept, J=6.7 Hz, 1H), 1.21 (s, 9H), 0.93 (d, J=6.7 Hz, 6H); $^{13}$C NMR (100 MHz, CDCl$_3$) δ 172.1, 74.0, 70.5, 63.1, 46.4, 28.5, 27.4, 20.0; LRMS (EI, 20 eV) m/z 217 (M$^+$, 4), 131 (100); HRMS (EI, 20 eV) for C$_{11}$H$_{23}$NO$_3$ (M$^+$): calculated 217.1678. found 217.1666.

Compound 29 (1.09 g, 5.0 mmol), triphenylphosine (1.97 g, 7.5 mmol) and N-hydroxyphthlalimide (0.98 g, 6.0 mmol) were dissolved in 50 mL dry THF. The solution was cooled to 0° C., followed by addition of DEAD (1.31 g, 7.5 mmol) dropwisely in 5 minutes. Then the solution was stirring at room temperature for additional 2 hours. After concentration, the residue was purified by silica gel using ethyl acetate/hexane as eluent to afford compound 30 (1.23 g, 68% yield) as colorless oil. [α]$^{20}_D$+70.2° (c 1.00, CHCl$_3$); $^1$H NMR (400 MHz, CDCl$_3$) δ7.86-7.78 (m, 4H), 7.69 (br, 1H), 4.78 (dd, J=3.6, 2.3 Hz, 1H), 4.06 (dd, J=10.7, 2.3 Hz, 1H), 3.93 (dd, J=10.7, 4.0 Hz, 1H), 3.367-3.30 (m, 1H), 3.05-3.00 (m, 1H), 1.90 (sept, J=6.7 Hz, 1H), 1.16 (s, 9H), 0.99 (dd, J=6.6, 4.1 Hz, 6H); $^{13}$C NMR (100 MHz, CDCl$_3$) δ 167.4, 163.7, 134.8, 128.7, 123.8, 87.7, 73.6, 61.8, 46.7, 28.4, 27.2, 20.1; LRMS (EI, 20 eV) m/z 362 (M$^+$, 3.5), 144 (100); HRMS (EI, 20 eV) for C$_{19}$H$_{26}$N$_2$O$_5$ calculated (M$^+$): 362.1842. found 362.1833.

Compound 30 (362 mg, 1.0 mmol) was dissolved in 5 mL MeOH. Then hydrazine hydrate (80% in water, 0.19 mL, 3.0 mmol) was added into the solution in one portion. After 2 hours (TLC showed complete conversion), MeOH and excessive hydrazine were removed in vacuum. The residue was suspended in ether/hexane (2:1, v/v); the white solid (phthalhydrazide, a byproduct of hydrazinolysis) was filtered off and washed with ether/hexane (2:1, v/v). The filtrate was collected and concentrated to afford compound 31 (197 mg, 85% yield) as colorless oil which can be used in the next step without further purification.

Isopbthalic acid (41.5 mg, 0.25 mmol) was added to a solution of compound 31 (116 mg, 0.5 mmol) in 5 mL CH$_2$Cl$_2$ followed by addition of HOAt (75 mg, 0.55 mmol) and EDC-HCl (120 mg, 0.6 mmol) successively. The solution was stirring for 10 hours, then diluted with CH$_2$Cl$_2$ (50 mL) and washed successively with 5% KHSO$_4$ (2 times), 10% NaHCO$_3$ (2 times), and dried with Na$_2$SO$_4$. After concentration, the residue was purified by flash column chromatography using ethyl acetate/hexane as eluent to afford compound 32 (77 mg, 52% yield) as colorless foam. [α]$^{20}_D$+27.5° (c 1.00, CHCl$_3$); $^1$H NMR (400 MHz, CDCl$_3$) δ 10.70 (s, 2H), 8.30 (br, 2H), 8.16 (s, 1H), 7.98 (d, J=7.6 Hz, 2H), 7.54 (t, J=7.6 Hz, 1H), 4.53 (dd, J=7.4, 2.6 Hz, 2H), 3.90 (d, J=8.7 Hz, 2H), 3.74 (dd, J=10.0, 8.0 Hz, 2H), 3.17-3.04 (m, 4H), 1.82 (sept, J=6.7 Hz, 2H), 1.20 (s, 18H), 0.91 (t, J=6.4 Hz, 6H); $^{13}$C NMR (100 MHz, CDCl$_3$) δ 168.5, 165.7, 131.7, 131.3, 129.4, 125.3, 86.6, 74.4, 62.4, 46.7, 28.3, 27.4, 20.1; LRMS (FAB) m/z 595 (M$^+$+H); HRMS (FAB) for C$_{30}$H$_{50}$N$_4$O$_8$ (M$^+$): calculated 594.3629. found 594.3620.

Compound 32 (77 mg, 0.13 mmol) was dissolved in 3 mL CH$_2$Cl$_2$, followed by addition of 1 mL TFA. After 30 min (TLC showed complete conversion), solvents were removed under reduced pressure and the remaining solid was washed with CH$_2$Cl$_2$ and collected to afford compound 36 (31 mg, 50% yield) as a white powder. M.p. 174-176° C.; [α]$^{20}_D$+ 50.8° (c 1.00, CHCl$_3$); $^1$H NMR (400 MHz, DMSO-d$_6$) δ12.29 (s, 2H), 8.31 (br, 2H), 8.1 (s, 1H), 7.91 (d, J=7.6 Hz, 2H), 7.54 (t, J=7.8 Hz, 1H), 4.33 (dd, J=5.2, 3.2 Hz, 2H), 3.77 (dd, J=12.2, 3.2 Hz, 4H), 2.95 (t, J=6.4 Hz, 4H), 1.69 (sept, J=6.7 Hz, 2H), 0.80 (dd, J=7.6, 6.2 Hz, 6H); $^{13}$C NMR (100 MHz, DMSO-d$_6$) δ168.9, 165.5, 132.0, 130.9, 129.6, 126.6, 87.6, 61.3, 46.3, 28.4, 20.2; LRMS (FAB) m/z 483 (M$^+$+H); HRMS (FAB) for C$_{22}$H$_{35}$N$_4$O$_8$ (M$^+$+H) calculated 483.2455. found 483.2451.

Preparation of Example 37

Scheme AJ

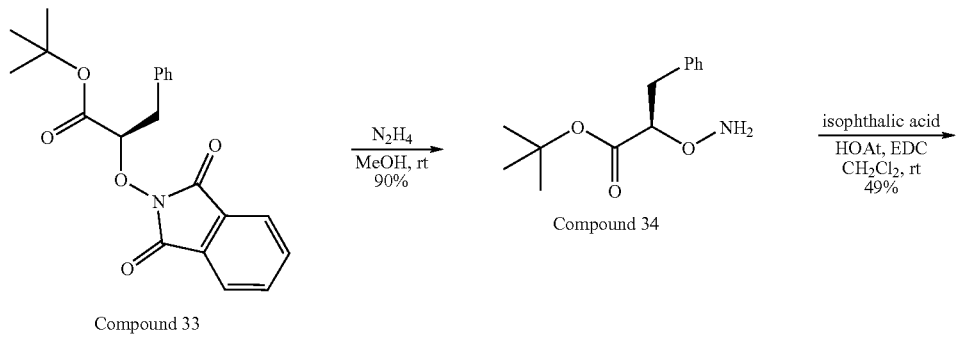

Compound 33

Compound 34

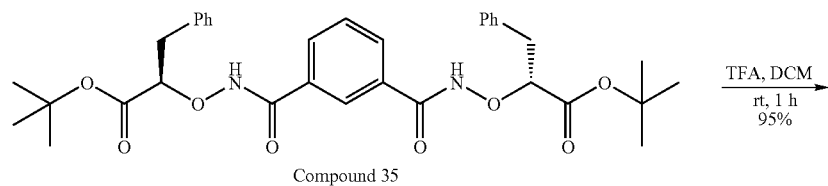

Compound 35

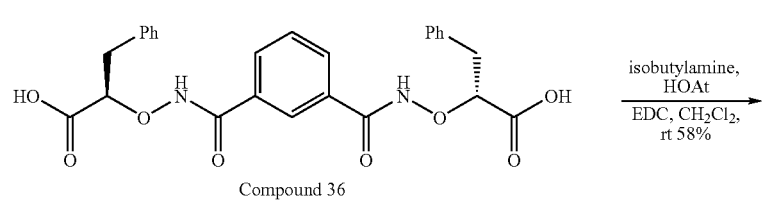

Compound 36

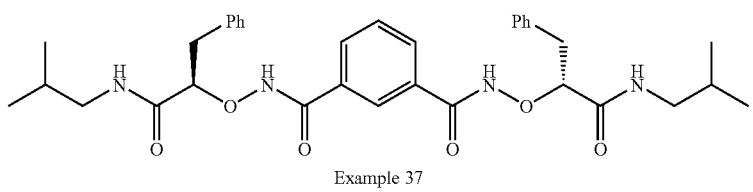

Example 37

Example 37 was prepared according to Scheme AJ. Compound 33 (735 mg, 2 mmol) was dissolved in 10 mL MeOH, then hydrazine hydrate (80% in water, 0.5 mL, 6 mmol) was added into the solution in one portion. After 2 hours (TLC showed complete conversion), MeOH and excessive hydrazine were removed in vacuum. The residue was suspended in ether/hexane (2:1, v/v). The white solid (phthalhydrazide, a byproduct of hydrazinolysis) was filtered off and washed with ether/hexane (2:1, v/v). The filtrate was collected and concentrated to afford compound 34 (426 mg, 90% yield) which can be used in the next step without further purification.

Isophthalic acid (83 mg, 0.5 mmol) was added to a solution of 34 (237 mg, 0.5 mmol) in 5 mL $CH_2Cl_2$, followed by addition of HOAt (75 mg, 0.55 mmol) and EDC.HCl (120 mg, 0.6 mmol) successively. The solution was stirring for 10 hours, then diluted with $CH_2Cl_2$ (10 mL) and washed successively with 5% $KHSO_4$ (2 times), 10% $NaHCO_3$ (2 times), and dried with $Na_2SO_4$. After concentration, the residue was purified by flash column chromatography using ethyl acetate/hexane as eluent to afford compound 35 (149 mg, 49% yield) as colorless syrup. $[\alpha]^{20}_D$+21.8° (c 1.00, $CHCl_3$); $^1$H NMR (300 MHz, $CDCl_3$) δ9.79 (br, 2H), 8.09 (s, 1H), 7.85 (d, J=6.0 Hz, 2H), 7.45 (t, J=7.5 Hz, 1H), 7.30-7.20 (m, 10H), 4.79 (t, J=6.0 Hz, 2H), 3.21 (d, J=6.0 Hz, 2H), 1.34 (s, 18H); $^{13}$C NMR (75 MHz, $CDCl_3$) δ175.9, 170.7, 138.0, 132.7, 131.2, 130.0, 129.5, 128.7, 127.8, 126.3, 84.2, 83.2, 37.8, 28.3; LRMS (FAB) m/z 605 (M$^+$+H); HRMS (FAB) for $C_{34}H_{40}N_2O_8$ (M$^+$): calculated 604.2784. found 604.2794.

Compound 35 (121 mg, 0.2 mmol) was dissolved in 5 mL $CH_2Cl_2$, TFA (2 mL) was added in this solution. After 30 minutes (TLC showed complete conversion), solvents were removed in vacuum and the remaining compound 36 was used in the next step without further purification.

The crude compound 36 and isobutylamine (30 μL, 0.29 mmol) were dissolved in 5 mL $CH_2Cl_2$, followed by addition of HOAt (26 mg, 0.22=mol) and EDC.HCl (60 mg, 0.3 mmol) successively. The solution was stirred for 10 hours, then diluted with $CH_2Cl_2$ (40 mL) and washed successively with 5% $KHSO_4$ (2 times), 10% $NaHCO_3$ (2 times), and dried with $Na_2SO_4$. After concentration, the residue was purified by flash column chromatography using acetone/$CH_2Cl_2$ as eluent to afford Example 37 (67 mg, 58% yield) as a white powder. M.p. 145-148° C.; $[\alpha]^{20}_D$+32.5° (c 1.00, $CH_3OH$); $^1$H NMR (300 MHz, $CDCl_3$) δ10.21 (br, 2H), 8.26 (t, J=5.4 Hz, 2H), 7.77 (d, J=7.6 Hz, 2H), 7.67 (s, 1H), 7.40 (t, J=7.8 Hz, 1H), 7.30-7.20 (m, 10H), 4.64 (dd, J=7.2, 2.4 Hz, 2H), 3.23-2.87 (m, 8H), 1.68 (qui, J=6.7 Hz, 2H), 0.78 (dd, J=14.4, 6.6 Hz, 6H); $^{13}$C NMR (75 MHz, $CDCl_3$) δ171.0, 166.3, 137.3, 132.3, 131.2, 129.8, 128.9, 127.2, 124.9, 118.6, 87.5, 47.2, 39.0, 28.7, 20.4; LRMS (FAB) m/z 603 (M$^+$+H); HRMS (FAB) calculated for $C_{34}H_{43}N_4O_6$ (M$^+$+H) 603.3183. found 603.3181.

Preparation of Examples 38 & 39

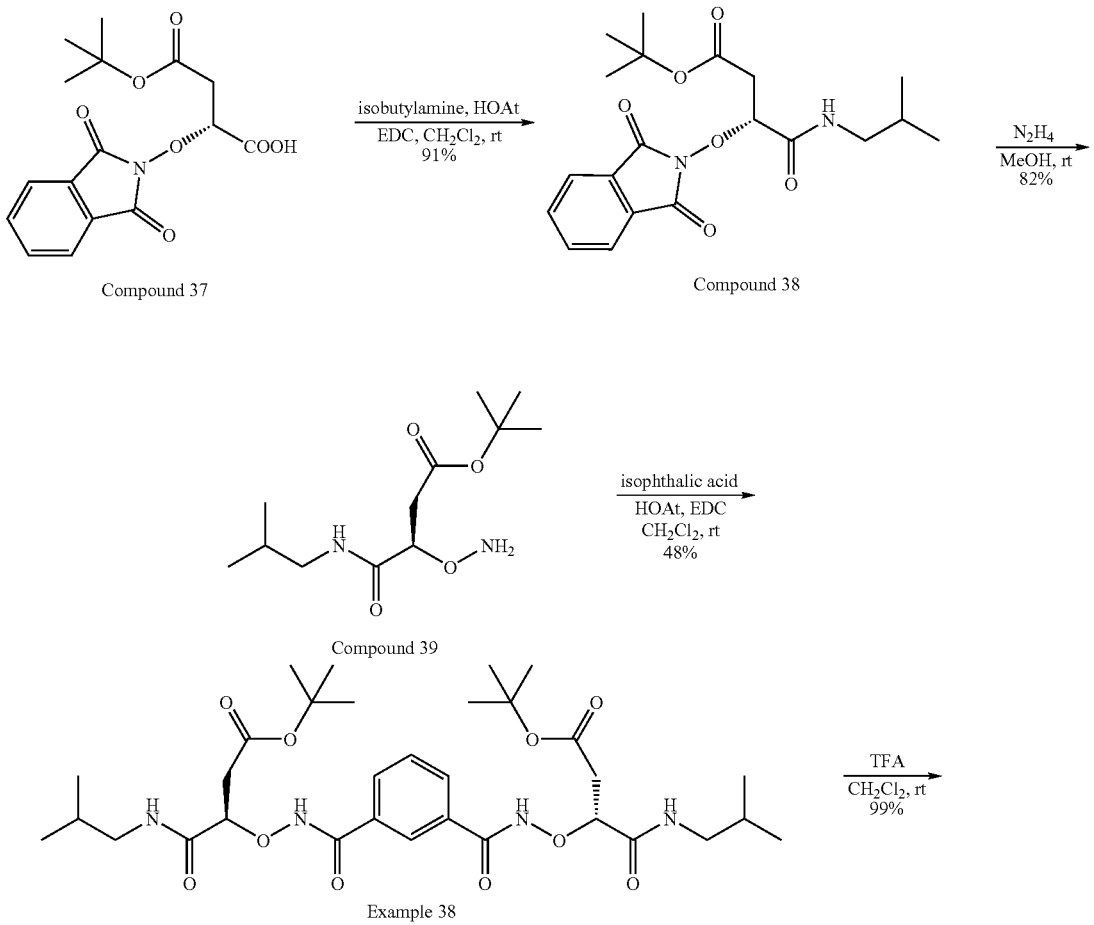

Scheme AK

Compound 37

Compound 38

Compound 39

Example 38

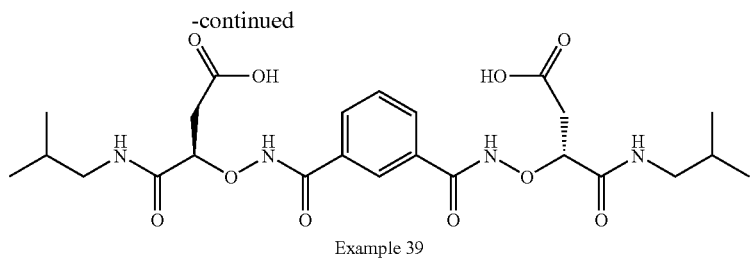

Example 39

Example 38 & 39 were prepared according to Scheme AK. Compound 37 [prepared according to *J. Org. Chem.* 2000, 65, 7667] (335 mg, 1.0 mmol) was added in 30 mL $CH_2Cl_2$, followed by addition of HOAt (150 mg, 1.1 mmol) and EDC HCl (240 mg, 1.2 mmol) successively with stirring. After 2 minutes, isobutylamine (105 μL, 1.05 mmol) was added dropwisely. The solution was stirring for 5 hours, then diluted with $CH_2Cl_2$ (30 mL) and washed successively with 5% $KHSO_4$ (2 times), 10% $NaHCO_3$ (2 times), and dried with $Na_2SO_4$. After concentration, the residue was purified by flash column chromatography using ethyl acetate/hexane as eluent to afford compound 38 (355 mg, 91% yield) as a colorless syrup. $^1$H NMR (400 MHz, $CDCl_3$) δ7.87-7.77 (m, 4H), 7.74 (br, 1H), 4.97 (dd, J=6.7 Hz, 4.2, 1H), 3.24-3.17 (m, 3H), 3.01 (dd, J=17.0, 6.8 Hz, 1H), 1.90 (sept, J=6.7 Hz, 1H), 1.45 (s, 9H), 0.99 (dd, J=6.6, 4.6 Hz, 6H); $^{13}$C NMR (100 MHz, $CDCl_3$) δ 169.1, 167.9, 163.6, 134.9, 128.6, 123.9, 85.2, 81.5, 47.0, 38.2, 28.4, 28.0, 20.1; LRMS (EI, 20 eV) m/z 390 (M$^+$, 2.9), 147 (100); HRMS (EI, 20 eV) for $C_{20}H_{26}N_2O_6$ (M$^+$): calculated 390.1791. found 390.1778.

Compound 38 (190 mg, 0.5 mmol) was dissolved in 5 mL MeOH, then hydrazine hydrate (80% in water, 0.19 mL, 1.5 mmol) was added into the solution in one portion. After 2 hours (TLC showed complete conversion), MeOH and excessive hydrazine were removed in vacuum. The residue was suspended in ether/hexane (2:1, v/v). The white solid (phthalhydrazide, a byproduct of hydrazinolysis) was filtered off and washed with ether/hexane (2:1, v/v). The filtrate was collected and concentrated to afford compound 39 (111 mg, 85% yield) which can be used in the next step without further purification.

Isophthalic acid (33.2 mg, 0.2 mmol) was added to a solution of compound 39 (104 mg, 0.4 mmol) in 5 mL $CH_2Cl_2$, followed by addition of HOAt (60 mg, 0.44 mmol) and EDC.HCl (100 mg, 0.5 mmol) successively. The solution was stirring for 10 hours, then diluted with $CH_2Cl_2$ (50 mL) and washed successively with 5% $KHSO_4$ (2 times), 10% $NaHCO_3$ (2 times), and dried with $Na_2SO_4$. After concentration, the residue was purified by flash column chromatography using acetone/$CH_2Cl_2$ as eluent to afford Example 38 (62 mg, 48% yield) as colorless foam. $^1$H NMR (400 MHz, $CDCl_3$) δ10.60 (s, 2H), 8.75 (br, 2H), 8.18 (s, 1H), 7.98 (d, J=7.8 Hz, 2H), 7.54 (t, J=7.7 Hz, 1H), 4.74 (dd, J=10.2, 2.6 Hz, 2H), 3.15-3.09 (m, 6H), 2.75 (dd, J=17.6, 10.4 Hz, 2H), 1.84 (sept, J=6.7 Hz, 2H), 1.47 (s, 18H), 0.91 (dd, J=10.8, 6.8 Hz, 6H); $^{13}$C NMR (100 MHz, $CDCl_3$) δ171.2, 169.3, 165.8, 131.4, 131.3, 129.5, 125.5, 84.0, 82.1, 46.9, 37.8, 28.3, 28.1, 20.1; LRMS (FAB) m/z (M$^+$+H) 651; HRMS (FAB) for $C_{32}H_{50}N_4O_{10}$ (M$^+$) calculated 650.3527. found 650.3520. Deprotection of Example 38 in TFA/$CH_2Cl_2$ gave Example 39 in quantitative yield.

Preparation of Examples 40 and 41

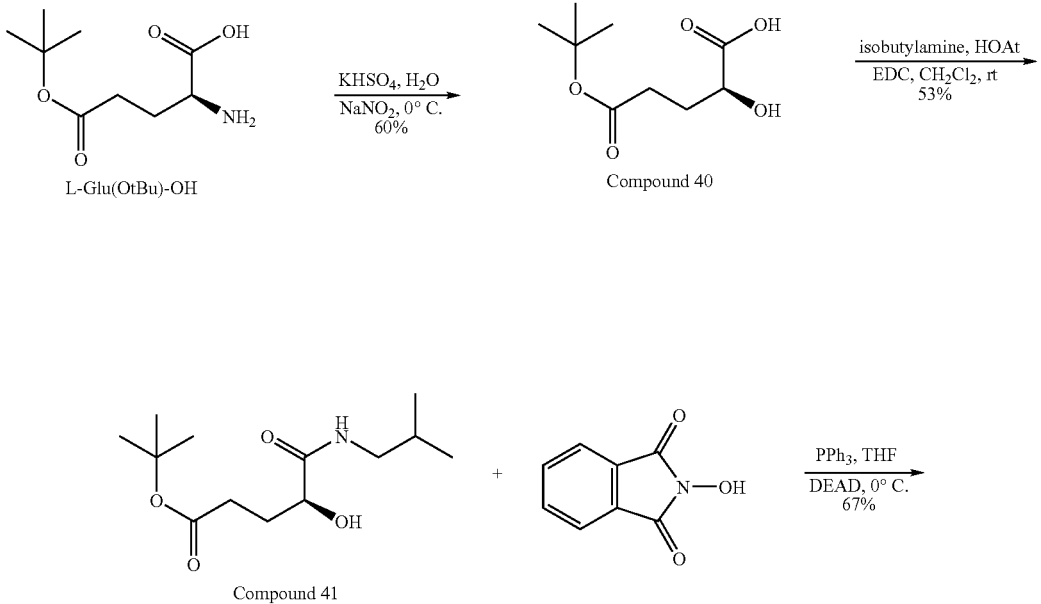

-continued

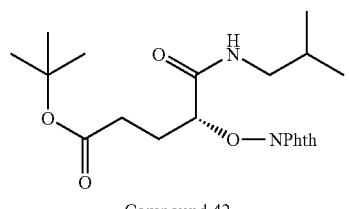 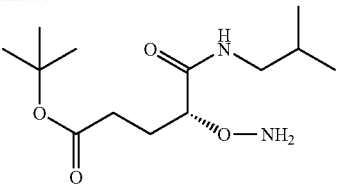

Compound 42            Compound 43

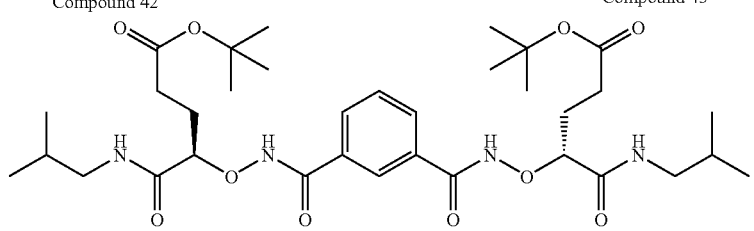

Example 40

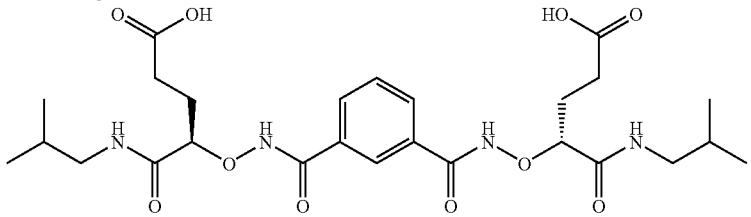

Example 41

Examples 40 and 41 were prepared according to Scheme AL. L-Glu-(OtBu)-OH (2.03 g, 10 mmol) was dissolved aqueous $KHSO_4$ solution (2.04 g in 50 mL water). Then the solution was cooled to 0° C., followed by addition aqueous $NaNO_2$ solution (1.04 g in 20 mL water) dropwisely during 30 minutes. Then stirring was continued overnight at room temperature. The solution was extracted with ethyl acetate 3 times; the combined organic phase was dried and concentrated to afford crude compound 40 (1.21 g, 60% yield) as a yellow oil, which can be used directly in the next step without further purification.

The crude compound 40 (1.21 g) and isobutylamine (0.89 mL, 9.0 mmol) were dissolved in 60 mL $CH_2Cl_2$, followed by addition of HOAt (1.36 g, 10 mmol) and EDC.HCl (1.20 g, 6.0 mmol) successively. The solution was stirring for 5 hours, then diluted with $CH_2Cl_2$ (100 mL) and washed successively with 5% $KHSO_4$ (2 times), 10% $NaHCO_3$ (2 times), and dried with $Na_2SO_4$. After concentration, the residue was purified by flash column chromatography using ethyl acetate/hexane as eluent to afford compound 41 (824 mg, 53%) yield as a colorless oil. $^1H$ NMR (300 MHz, $CDCl_3$) δ6.97 (br, 1H), 4.72 (d, J=4.4 Hz, 1H), 4.14-4.10 (m, 1H), 3.17-3.07 (m, 2H), 2.51-2.44 (m, 2H), 2.20-2.11 (m, 1H), 1.98-1.90 (m, 1H), 1.79 (sept, J=6.7 Hz, 1H), 1.45 (s, 9H), 0.92 (d, J=6.7 Hz, 6H); $^{13}C$ NMR (75 MHz, $CDCl_3$) δ176.5, 173.8, 81.9, 72.6, 46.7, 32.6, 29.6, 28.5, 28.4, 20.4; LRMS (EI, 20 eV) m/z 259 ($M^+$, 2), 85 (100); HRMS (EI, 20 eV) for $C_{13}H_{25}NO_4$ ($M^+$): calculated 259.1784. found 259.1783.

Compound 41 (777 mg, 3.0 mmol), triphenylphosine (1.18 g, 4.5 mmol) and N-hydroxyphthlalimide (587 mg, 3.6 mmol) were dissolved in 30 mL dry THF. Then the solution was cooled to 0° C., followed by addition of DEAD (784 mg, 4.5 mmol) dropwisely in 5 minutes. Then the solution was stirring at room temperature for additional 2 hours. After concentration, the residue was purified by flash column chromatography using ethyl acetate/hexane as eluent to afford compound 42 (812 mg, 67% yield) as colorless foam. $^1H$ NMR (300 MHz, $CDCl_3$) δ7.86-7.79 (m, 4H), 7.70 (br, 1H), 4.73 (dd, J=8.1, 4.0 Hz, 1H), 3.30-3.21 (m, 1H), 3.07-3.00 (m, 1H), 2.69-2.62 (m, 2H), 2.41-2.30 (m, 1H), 2.21-2.11 (m, 1H), 1.87 (sept, J=6.75 Hz, 1H), 1.46 (s, 9H), 0.96 (t, J=6.3 Hz, 6H); $^{13}C$ NMR (75 MHz, $CDCl_3$) δ169.9, 168.3, 164.6, 135.0, 128.9, 123.9, 87.4, 85.3, 46.9, 31.5, 28.5, 28.3, 27.9, 20.1; LRMS (EI, 20 eV) m/z 405 ($M^+$, 3), 147 (100); HRMS (EI, 20 eV) for $C_{21}H_{28}N_2O_6$ ($M^+$): calculated 404.1947. found 404.1937.

Compound 42 (203 mg, 0.5 mmol) was dissolved in 5 mL MeOH, then hydrazine hydrate (80% in water, 0.19 mL, 1.5 mmol) was added into the solution in one portion. After 2 hours (TLC showed complete conversion), MeOH and excessive hydrazine were removed in vacuum. The residue was suspended in ether/hexane (2:1, v/v). The white solid Cphthalhydrazide, a byproduct of hydrozinolysis) was filtered off and washed with ether/hexane (2:1, v/v). The filtrate was collected and concentrated to afford compound 43 (114 mg, 83% yield), which can be used in the next step without further purification.

Isophthalic acid (33.2 mg, 0.2 mmol) was added to a solution of compound 43 (110 mg, 0.4 mmol) in 5 mL $CH_2Cl_2$, followed by addition of HOAt (60 mg, 0.44 mmol) and EDC.HCl (100 mg, 0.5 mmol) successively. The solution was stirred for 10 hours, then diluted with $CH_2Cl_2$ (50 mL) and washed successively with 5% $KHSO_4$ (2 times), 10% $NaHCO_3$ (2 times), and dried with $Na_2SO_4$. After concentration, the residue was purified by flash column chromatography using acetone/$CH_2Cl_2$ as eluent to afford Example 40 (64 mg, 47% yield) as colorless foam. $^1H$ NMR (300 MHz, $CDCl_3$) δ10.79 (s, 2H), 8.32 (br, 2H), 8.18 (s, 1H), 7.99 (d, J=7.8 Hz, 2H), 7.54 (t, J=7.7 Hz, 1H), 4.42 (dd, J=7.6 Hz, 3.4, 2H), 3.12-3.04 3 (m, 4H), 2.50-2.42 (m, 6H), 2.15-2.08 (m, 2H), 1.81 (sept, J=6.7 Hz, 2H), 1.43 (s, 18H), 0.89 (t, J=6.2 Hz, 6H); $^{13}$C NMR (75 MHz, CDCl$_3$) δ 174.2, 170.4, 166.3, 132.0, 131.7, 129.8, 126.0, 86.5, 81.7, 47.2, 32.2, 28.7, 28.4, 26.9, 20.5; LRMS (FAB) m/z 679 (M$^+$+H); HRMS (FAB) for C$_{34}$H$_{54}$N$_4$O$_{10}$ (M$^+$): calculated 678.3840. found 678.3852. Deprotection of Example 40 in TFA/CH$_2$Cl$_2$ gave Example 41 in quantitative yield.

Preparation of Example 42

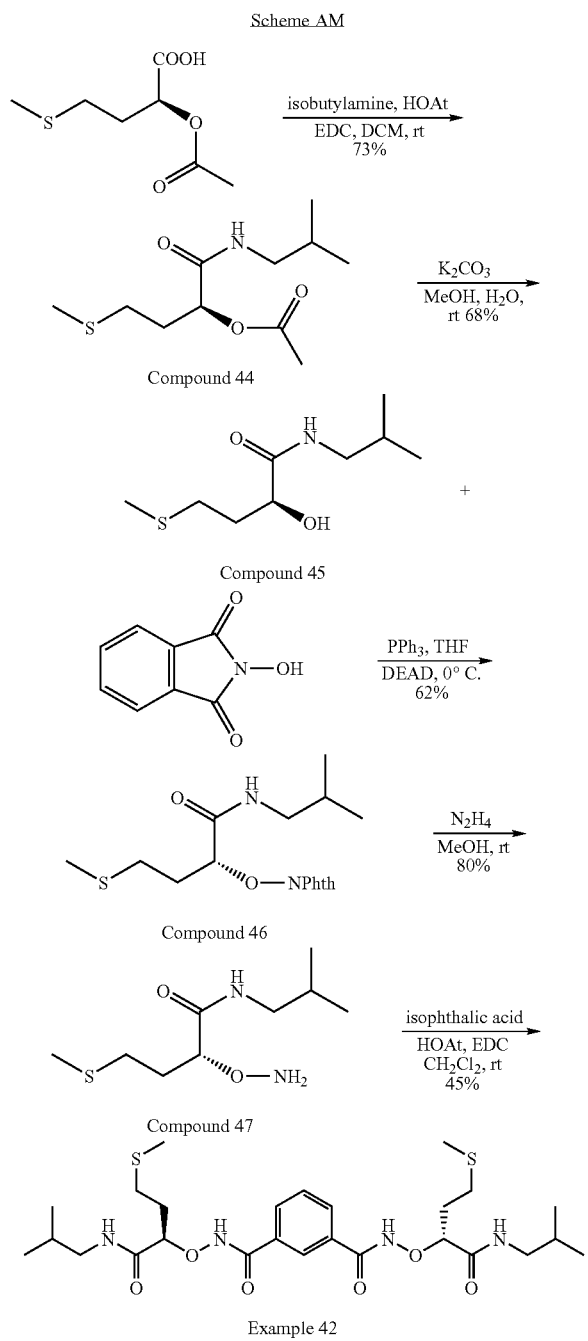

Example 42 were prepared according to Scheme AM. (S)-2-Acetoxy-4-(methylthio)-butyric acid [prepared according to the patent EP0338735] (960 mg, 5.0 mmol) and isobutylamine (0.75 mL, 7.5 mmol) were dissolved in 50 mL CH$_2$Cl$_2$, followed by the addition of HOAt (748 mg, 5.5 mmol) and EDC·HCl (1.2 g, 6.0 mmol) successively. The solution was stirred for 5 hours, then diluted with CH$_2$Cl$_2$ (100 mL) and washed successively with 5% KHSO$_4$ (2 times), 10% NaHCO$_3$ (2 times), and dried with Na$_2$SO$_4$. After concentration, the residue was purified by flash column chromatography using ethyl acetate/hexane as eluent to afford compound 44 (902 mg, 73% yield) as colorless oil. $^1$H NMR (300 MHz, CDCl$_3$) δ6.17 (br, 1H), 5.25 (dd, J=6.7, 5.5 Hz, 1H), 3.13-3.09 (m, 2H), 2.57-2.52 (m, 2H), 2.19-2.12 (m, 5H), 2.10 (s, 3H), 1.81 (sept, J=6.7 Hz, 1H), 1.21 (s, 9H), 0.93 (d, J=6.7 Hz, 6H); $^{13}$C NMR (75 MHz, CDCl$_3$) δ169.7, 169.1, 73.0, 46.5, 31.3, 29.5, 28.4, 21.0, 20.0, 15.4.

Compound 44 (742 mg, 3 mmol) was dissolved in 5 mL MeOH, then followed by addition of K$_2$CO$_3$ (830 mg, 6 mmol) and 1 mL water. After 5 hours (TLC indicated complete conversion), the solvents were removed in vacuum. The residue was purified by flash column chromatography using ethyl acetate/hexane as eluent to afford compound 45 (418 mg, 68% yield) as a colorless oil. $^1$H NMR (300 MHz, CDCl$_3$) δ6.86 (br, 1H), 4.30-4.27 (m, 1H), 4.08 (br, 1H), 3.17-3.08 (m, 2H), 2.70-2.64 (m, 2H), 2.18-2.13 (m, 4H), 1.97-1.92 (m, 1H), 1.80 (sept, J=6.7 Hz, 1H), 0.92 (d, J=7.0 Hz, 6H); $^{13}$C NMR (75 MHz, CDCl$_3$) δ173.5, 71.8, 46.4, 32.9, 30.4, 28.5, 20.0, 15.4. LRMS (EI, 20 eV) m/z 205 (M$^+$, 20), 131 (100); HRMS (EI, 20 eV) for C$_9$H$_{19}$NO$_2$S (M$^+$): calculated 205.1137. found 205.1139.

Compound 45 (410 mg, 2.0 mmol), triphenylphosine (787 mg, 3.0 mmol) and N-hydroxyphthlalimide (392 mg, 2.4 mmol) were dissolved in 30 mL dry THF. Then the solution was cooled to 0° C., followed by addition of DEAD (523 mg, 3.0 mmol) dropwisely in 5 minutes. Then the solution was stirred at room temperature for additional 2 hours. After concentration, the residue was purified by flash column chromatography using ethyl acetate/hexane as eluent to afford compound 46 (435 mg, 62%) as colorless foam. $^1$H NMR (300 MHz, CDCl$_3$) δ7.86-7.78 (m, 5H), 4.79 (dd, J=7.8, 3.7 Hz, 1H), 3.29-3.22 (m, 1H), 3.08-3.02 (m, 1H), 2.92-2.82 (m, 2H), 2.48-2.15 (m, 5H), 1.89 (sept, J=6.7 Hz, 1H), 0.97 (t, J=6.3 Hz, 6H); $^{13}$C NMR (75 MHz, CDCl$_3$) δ169.7, 164.3, 135.5, 129.0, 124.3, 87.8, 85.8, 47.2, 32.7, 30.7, 28.8, 20.5, 15.6; LRMS (EI, 20 eV) m/z 350 (M$^+$, 1) 148 (100); HRMS (EI, 20 eV) calculated for C$_{17}$H$_{22}$N$_2$O$_4$S (M$^+$) 350.1300. found 350.1285.

Compound 46 (175 mg, 0.5 mmol) was dissolved in 5 mL MeOH, then hydrazine hydrate (80% in water, 0.19 mL, 1.5 mmol) was added in one portion. After 2 hours (TLC showed complete conversion), MeOH and excessive hydrazine were removed in vacuum. The residue was suspended in ether/hexane (2:1, v/v); the white solid (phthalhydrazide, a byproduct of hydrazinolysis) was filtered off and washed with ether/hexane (2:1, v/v). The filtrate was collected and concentrated to afford compound 47 (90 mg, 83% yield), which can be used in the next step without further purification.

Isophthalic acid (33.2 mg, 0.2 mmol) was added to a solution of compound 47 (88 mg, 0.4 mmol) in 5 mL CH$_2$Cl$_2$, followed by addition of HOAt (60 mg, 0.44 mmol) and EDC (100 mg, 0.5 mmol) successively. The solution was stirred for 10 hours, then diluted with CH$_2$Cl$_2$ (50 mL) and washed successively with 5% KHSO$_4$ (2 times), 10% NaHCO$_3$ (2 times), and dried with Na$_2$SO$_4$. After concentration, the residue was purified by flash column chromatography using acetone/CH$_2$Cl$_2$ as eluent to afford Example 42 (60 mg 47% yield) as colorless foam. $^1$H NMR (300

MHz, CDCl$_3$) δ11.03 (br, 2H), 8.33 (br, 2H), 8.16 (s, 1H), 8.02 (d, J=7.4 Hz, 2H), 7.54 (t, J=7.7 Hz, 1H), 4.54 (dd, J=8.1, 3.3 Hz, 2H), 3.07-2.97 (m, 4H), 2.75-2.65 (m, 4H), 2.20-1.98 (m, 10H), 1.76 (sept, J=6.7 Hz, 2H), 0.89 (dd, J=12.2, 6.6 Hz, 6H); $^{13}$C NMR (75 MHz, CDCl$_3$) δ171.4, 166.1, 132.1, 131.7, 129.9, 125.5, 86.6, 47.2, 31.8, 30.2, 28.1, 20.4, 15.5; LRMS (FAB) m/z 571 (M$^+$+H); HRMS (FAB) for C$_{26}$H$_{42}$N$_4$O$_6$S$_2$ (M$^+$): calculated 570.2546. found 570.2551.

Example 43 pH-Stat Fluorometric Transport Assay

This Example illustrates that the compound of Example 2 mediates chloride release when incorporated into liposomes. The liposome-based pH-stat fluorometric assay is an assay routinely used for identification of physiologically relevant ionophores, which are disclosed in (a) Deng, G., Dewa, T. and Regen, S. L. *J. Am. Chem. Soc.* 1996, 118, 8975; (b) Schlesinger, P. H., Ferdani, R., Liu, J., Pajewska, J., Pajewski, R., Saito, M., Shabany, H. and Gokel, G. W. *J. Am. Chem. Soc.* 2002, 124, 1848; (c) Sidorov, V., Kotch, F. W., Abdrakhmanova, G., Mizani, R., Fettinger, J. C. and Davis, J. T. *J. Am. Chem. Soc.* 2002, 124, 2267; (d) Sidorov, V., Kotch, F. W., Kuebler, J. L., Lam, Y.-F. and Davis, J. T. *J. Am. Chem. Soc.* 2003, 125, 2840; and (e) Baumeister, B., Sakai, N. and Matile, S. *Angew. Chem., Int. Ed.* 2000, 39, 1955, all of which are incorporated herein by reference. For example, in this assay, a controlled amount of the base and potential ionophore is added to a suspension of liposomes containing a pH-sensitive dye, 8-hydroxypyrene-1,3,6-trisulfonate (HPTS, pyranine). The resulting pH gradient across the bilayer membrane causes the efflux of hydronium ions or the influx of hydroxide ions and builds up an electrostatic potential. This potential can be compensated by the efflux of anions or influx of cations (H$^+$/M$^+$ or OH$^-$/A$^-$ antiport and H$^+$/A$^-$ or M$^+$/OH$^-$ symport mechanisms are possible). If the compound of interest mediates such ion transport, the efflux of hydronium ions or the influx of hydroxide ions continues altering the intravascular pH and the fluorescence of the reporter dye.

Figure 5:
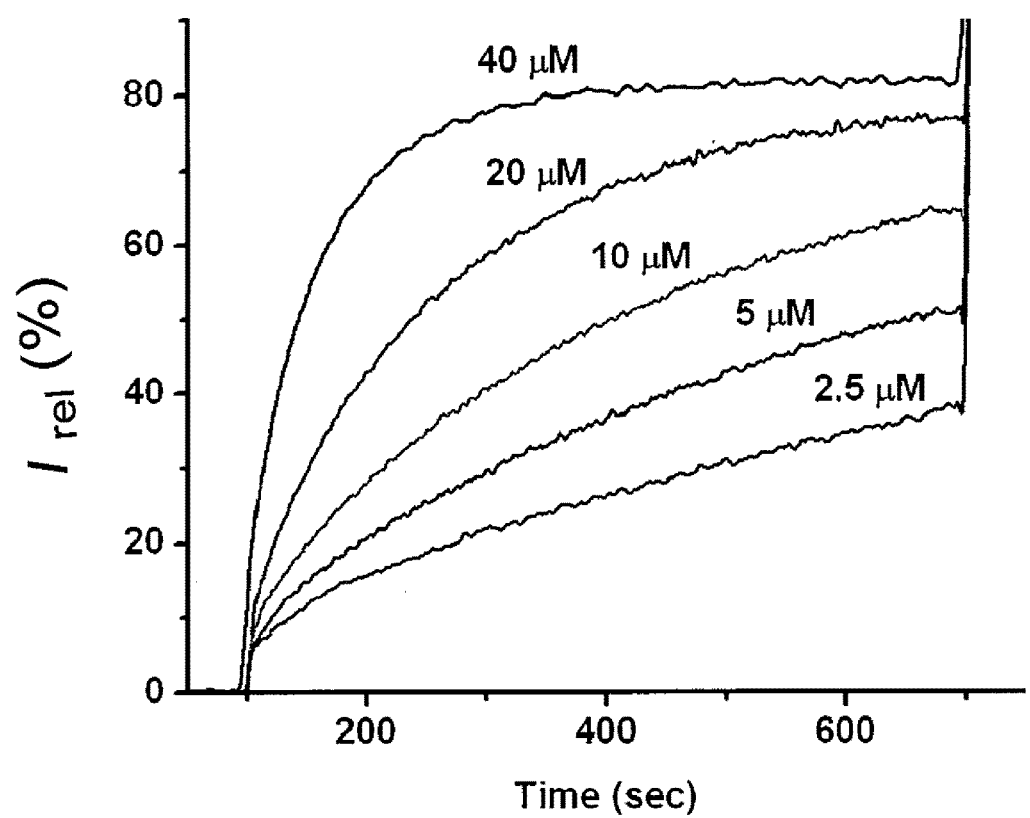
FIG. 5 shows chloride release mediated by Example 2 at different concentrations from large unilamellar vesicles (LUVs), where NaCl extra- and intravesicular buffers were used. The experimental details are described in Example 43.
Figure 6:
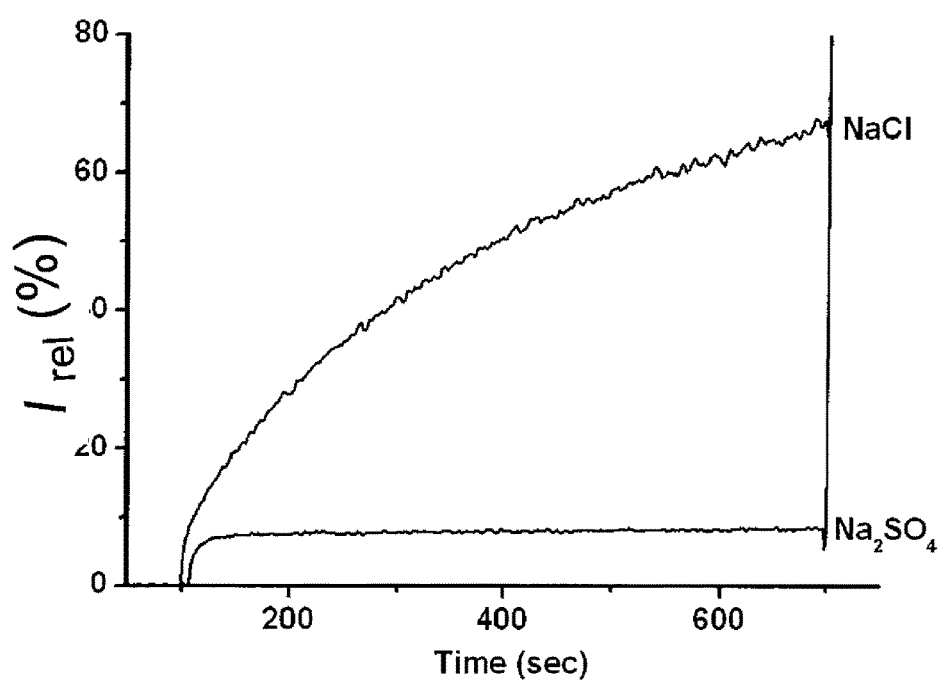
FIG. 6 shows Example 2 mediated electrolyte exchange in the presence of chloride but not in the presence of sulfate. The experimental details are described in Example 43.
Figure 7A:
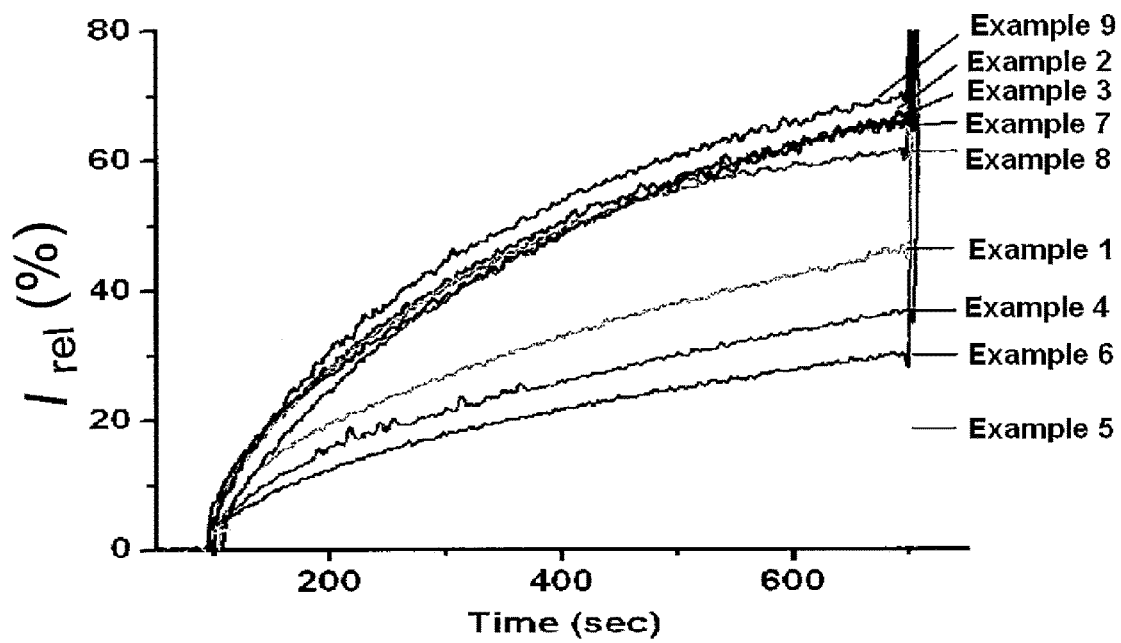
FIG. 7 shows chloride transport ability of different synthetic ion channels derived from Examples 1-42 in LUVs, where NaCl extra- and intravesicular buffers were used.
Figure 7B:
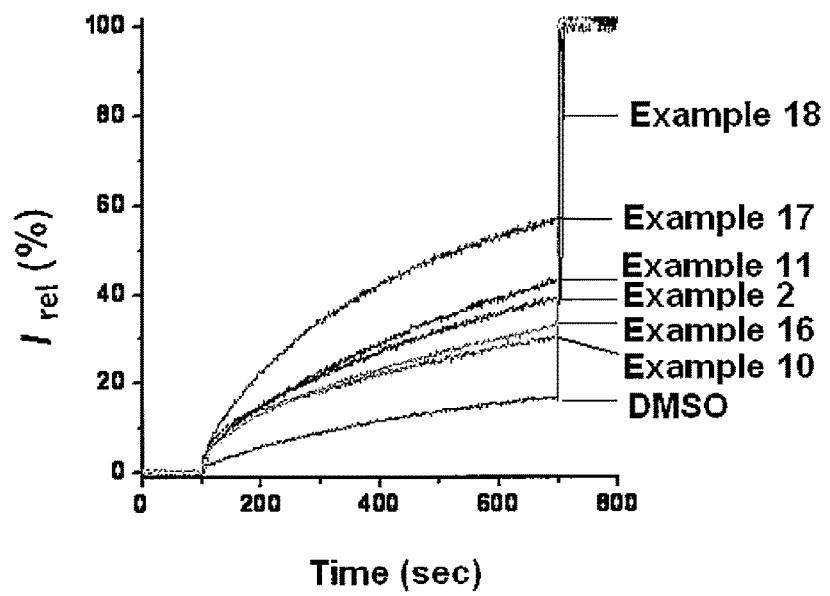
Figure 7C:
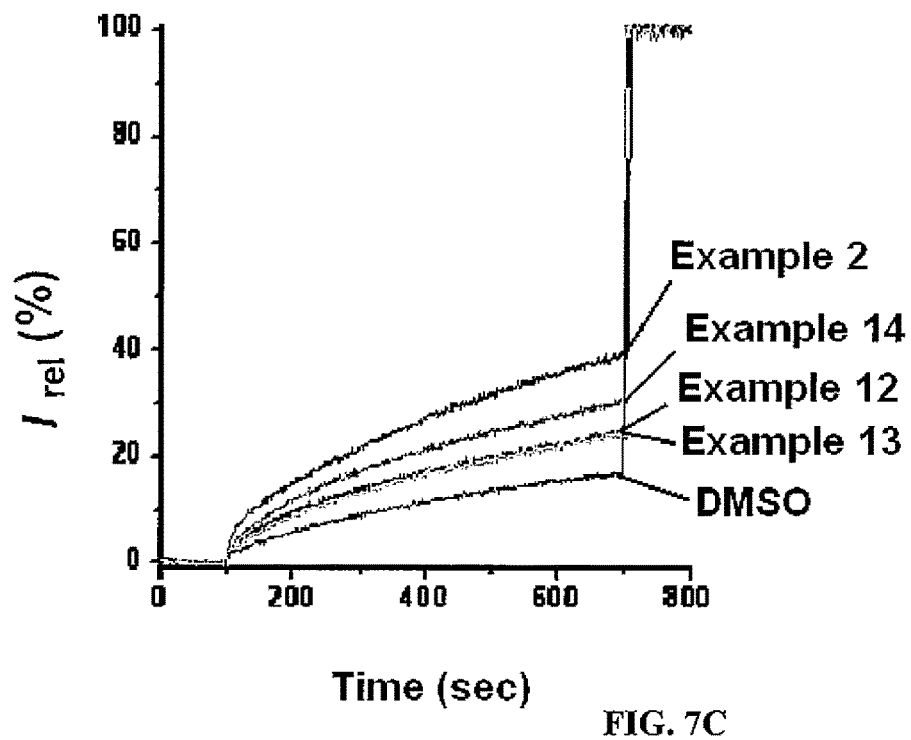
Figure 7D:
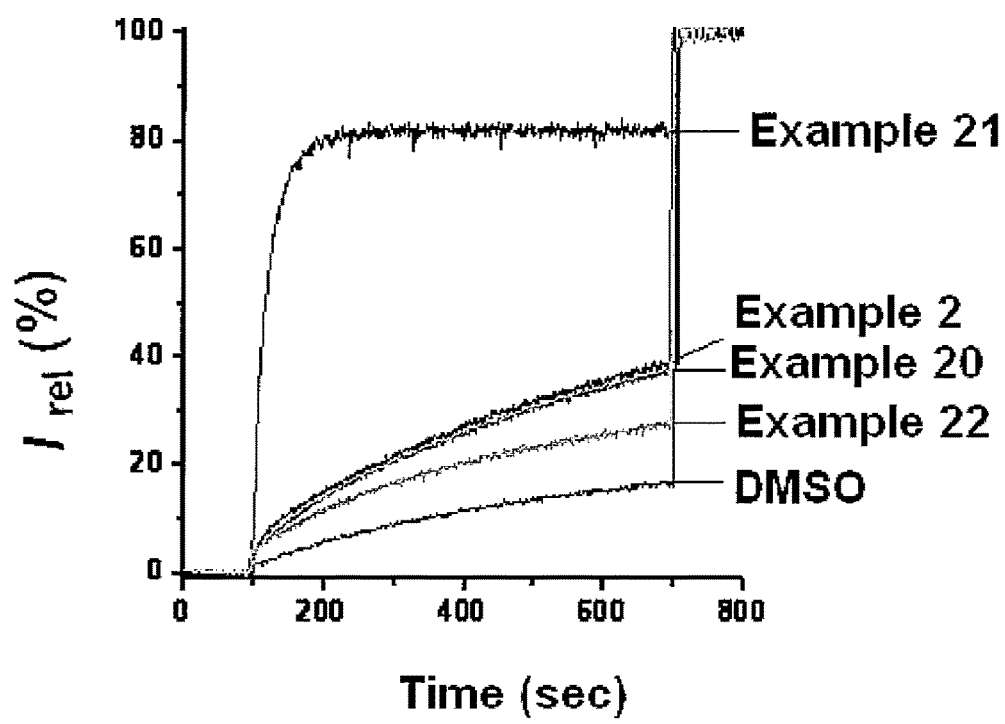
Figure 7E:
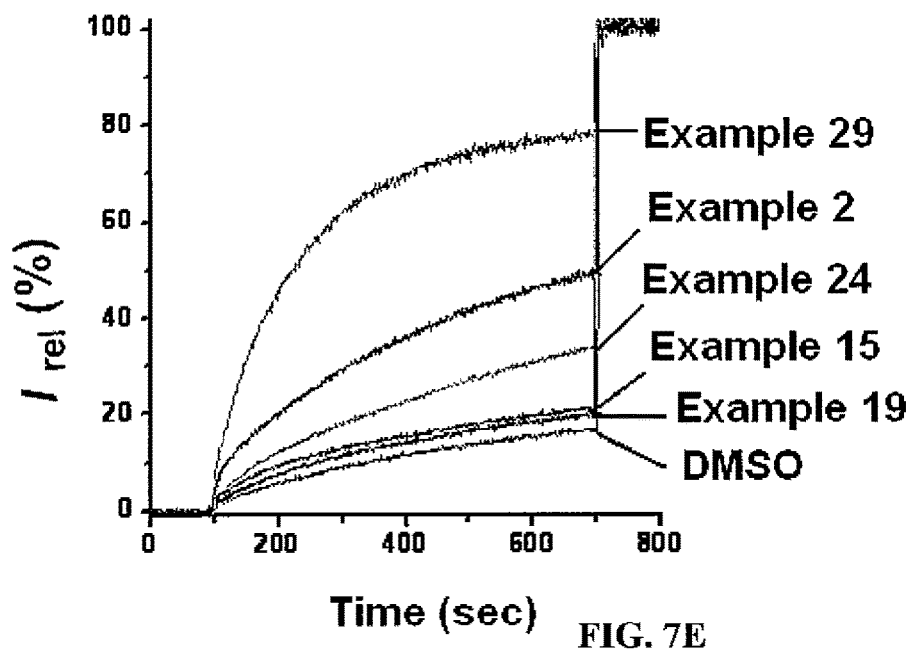
Figure 7F:
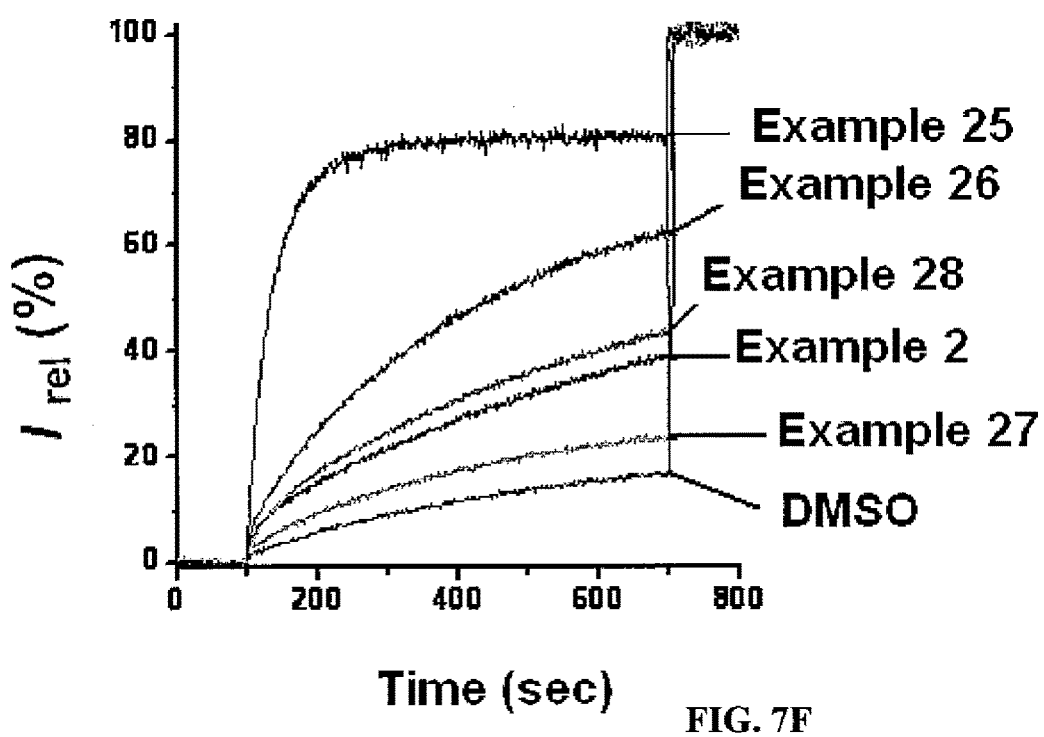
Figure 7G:
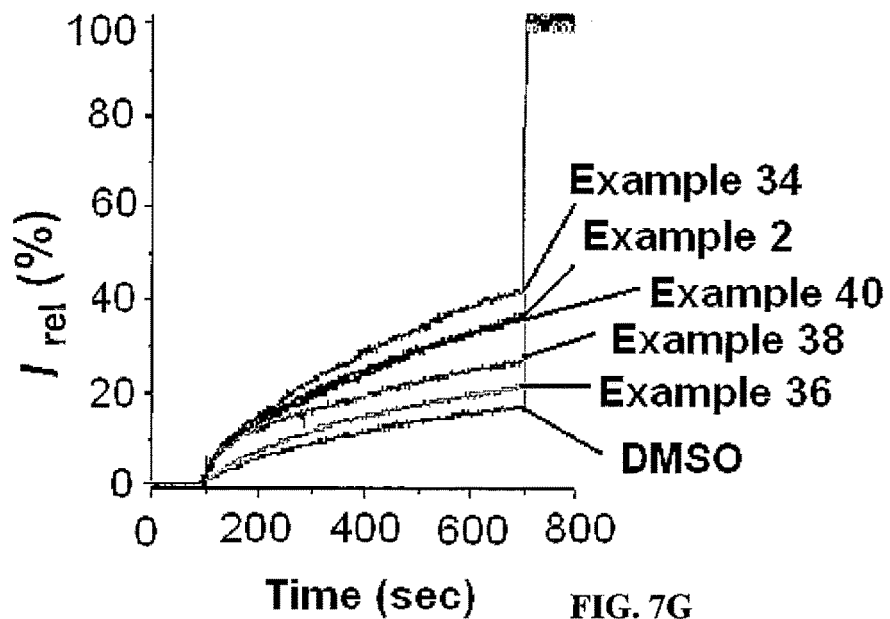
Figure 7H:
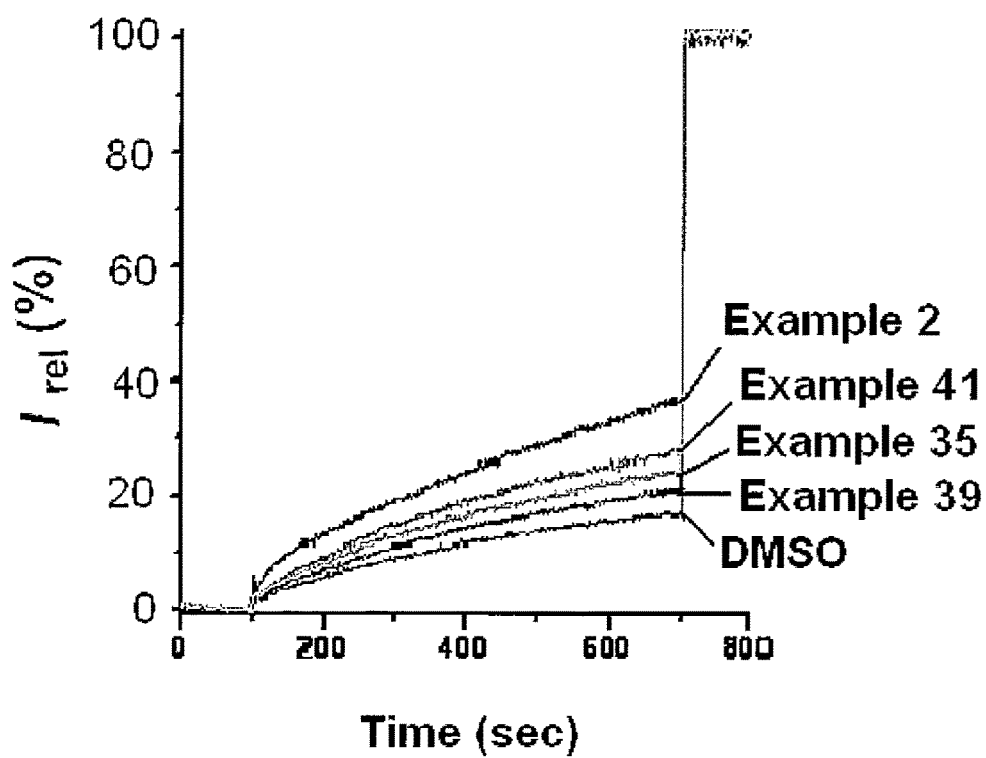
Figure 7I:
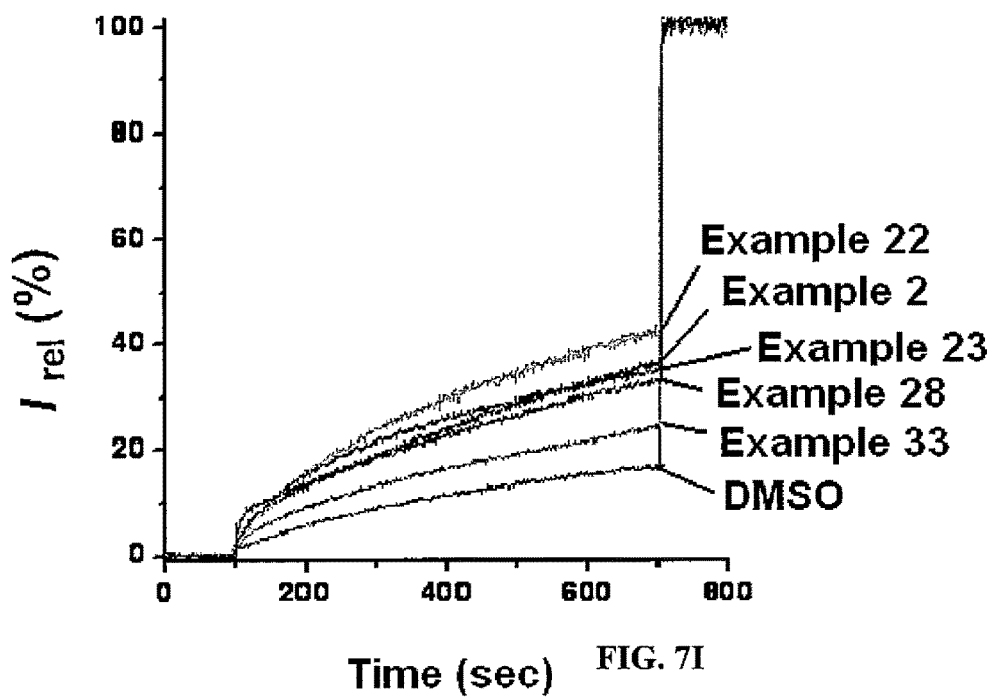
Figure 7J:
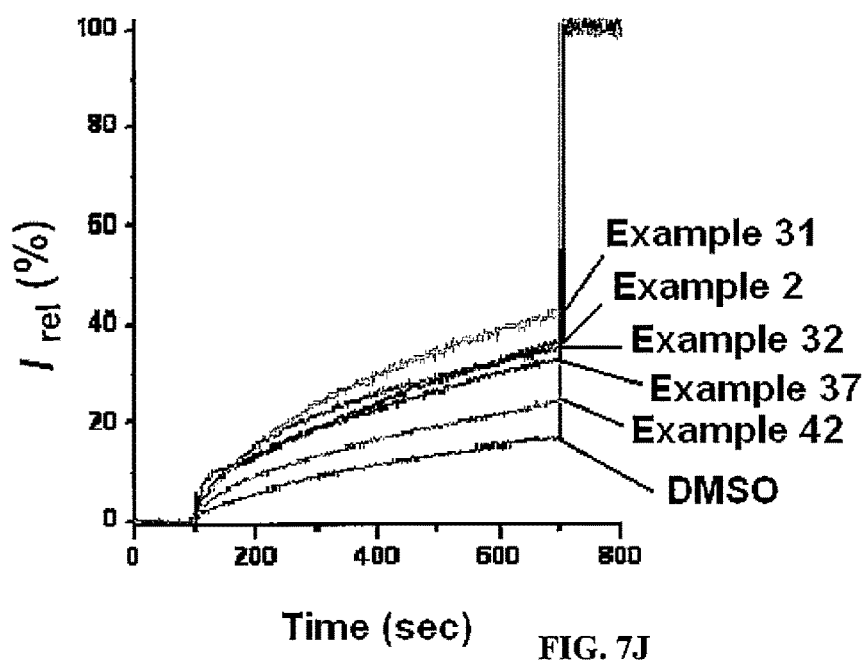

Example 2-mediated chloride release was determined in large unilamellar vesicles (LUVs) of 100 nm average dimension, as reported in Sidorov, V., Kotch, F. W., Abdrakhmanova, G, Mizani, R., Fettinger, J. C. and Davis, J. T. *J. Am. Chem. Soc.* 2002, 124, 2267. FIG. 5 shows that the application of Example 2 resulted in rapid, concentration-dependent exchange between extra- and intravesicular electrolytes. Importantly, Example 2 mediated electrolyte exchange with high anion selectivity. It mediated electrolyte exchange in the presence of chloride but not in the presence of sulfate (see FIG. 6). In contrast to the results shown in FIG. 6, where NaCl extra- and intravesicular buffers were used, no transport activity was detected in LUVs symmetrically loaded with Na$_2$SO$_4$. This anion-dependent activity is a strong evidence that Example 2 mediates chloride transport across the bilayer. FIG. 7 shows that in addition to Example 2, Examples 1 and 3-42 can also mediate chloride transport across lipid bilayers of chloride-containing liposomes with different efficiencies.

Example 44

Example 44 shows that the compound of Example 2 can function as a voltage-dependent chloride-selective channel when partitioned into lipid bilayers. Single-channel recording, using patch clamp techniques, is the most critical test for identifying ion channel formation, which is distinguished from other ion transport mechanisms such as ion carriers, and quantifying ion transport efficiency of a membrane channel. The channel-forming activity of Example 2 incorporated in lipid bilayers is examined using patch-clamp technique on giant liposomes. Characteristic single-channel currents were recorded with primary conductance of 54 pS in symmetric 0.2 M N-methyl-glucamine hydrochloride (NMG-Cl) solutions when application of Example 2 in bath solution (FIG. 8), indicating that Example 2 can partition into lipid bilayers of liposomes efficiently and thereby forms ionic channels.

Figure 8A:
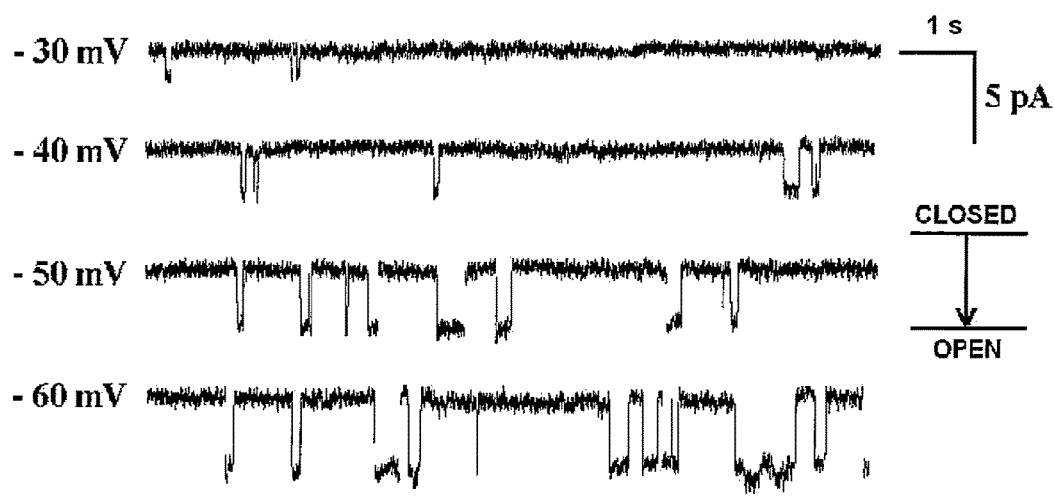
FIG. 8 shows single-channel recording results illustrating that Example 2 can mediate chloride transport across lipid bilayer by an ion channel mechanism featuring voltage-dependent gating property. The experimental details are described in Example 44.
Figure 8B:
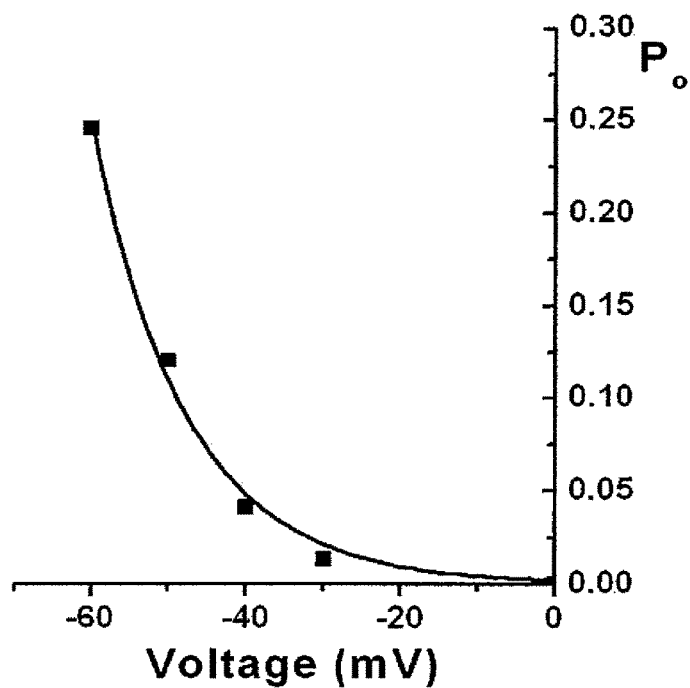

The two key properties of ion channels in nature are ion selectivity, that is, a channel permits only certain ionic species to flow through its pore, and gating referring to the mechanism of channel opening and closing. The ion channels formed by Example 2 turned out to be anion selective and voltage-gated. There was no measurable change either in conductance or in reversal potential when NMDG-Cl in the bath solution was replaced by potassium chloride (KCl), suggesting that these channels are not permeable to K ions. The channel open probability (P$_0$) and frequency were enhanced steeply upon increasing voltages of lipid bilayers within a physiologically relevant range of voltages, suggesting voltage-dependent gating (FIG. 8).

Example 45

Example 45 shows that the compound of Example 2 partitions into human cell membranes and dramatically increases cell chloride currents. The whole-cell configuration of the patch-clamp technique was used to examine the electrophysiological properties of the ionic currents induced by Example 2 in human embryonic kidney (HEK 293) cells. HEK 293 cell line originally obtained from the American Type Culture Collection, were cultured in DMEM supplemented with 10% FBS and 100 IU/ml penicillin G and 0.1 mg/ml streptomycin. Cells were grown at 37° C. in a 5% CO$_2$ humidified incubator. Whole-cell chloride currents were recorded by using an EPC 9 patch clamp amplifier (HEKA Elektronik, Lambrecht/Pfalz, Germany) in voltage-clamp mode, controlled by Pulse/PulseFit 8.7 software (HEKA). Patch pipettes (resistance, 3-5 MΩ) were filled with a solution internal pipette solution containing CsCl 140, MgCl$_2$ 1, HEPES 10, EGTA 5, Na$_2$ATP 5 (in mmol/L, pH 7.2 with CsOH). The bath solution contained NaCl 140, CsCl 5, CaCl$_2$ 1, MgCl$_2$ 1, HEPES 10 (in mmol/L, pH 7.4 with CsOH). After gigaohm seals were obtained, the membrane was ruptured with a pulsed negative pressure. Pipette and membrane capacitance were automatically compensated. Series resistance was typically compensated by 70%. The cells were held at 0 mV and voltage steps ranging from −80 to +80 mV were applied for 800 ms in 20 mV step increments. All macroscopic currents were sampled at 50 kHz and filtered at 5 kHz, and data were analyzed with PulseFit (HEKA). Changes of Cl current were detected from the same cells before and after exposure to the bath solution containing Example 2 at the concentration of 50 nM. All experiments were performed at room temperature (22-25° C.)

Figure 9:
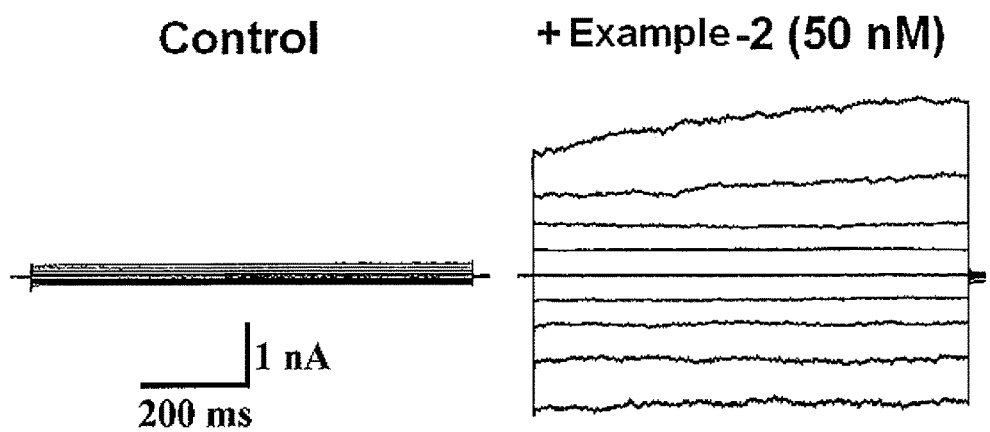
FIG. 9 shows whole-cell recording results illustrating that Example 2 can increase cell chloride currents when partitioned into human cell membranes. The experimental details are described in Example 45.

At a low concentration of 50 nM, Example 2 caused a large increase in whole cell currents (FIG. 9), indicating that Example 2 may mediate Cl ions transport efficiently across cell membranes of HEK 293 cells. In addition, the induced currents were not reduced in the presence of a cellular anion transport inhibitor such as 4,4'-diisothiocyanatostilbene-2, 2'-disulfonate (DIDS). This property rules out that Example 2 may increase whole cell currents by activating the natural chloride channels in HEK 293 cells and suggests that the synthetic chloride channels formed by Example 2 indeed accounts for the observed currents.

Example 46

Example 46 shows the chloride transport activity of the compound of Example 2 in liposome with chloride-sensitive fluorescent indicator SPQ.

Liposome Preparation:

Egg yolk L-α-phosphatidylcholine (EYPC, 91 mg, 120 μmol) was dissolved in a $CHCl_3$/MeOH mixture, the solution was evaporated under reduced pressure and the resulting thin film was dried under high vacuum for 3 hours. The lipid film was hydrated in 1.2 mL of solution A (200 mM $NaNO_3$, 0.5 mM SPQ) for 2 hours. During hydration, the suspension was submitted to 5 freeze-thaw cycles (liquid nitrogen, water at room temperature). The large multilamellar liposome suspension (1 mL) was submitted to high-pressure extrusion at room temperature (>21 extrusions through a 0.1 μm polycarbonate membrane afforded a suspension of large unilamellar vesicles (LUVs) with an average diameter of 100 nm). The LUV suspension was separated from extravesicular dye by size exclusion chromatography (SEC) (stationary phase: Sephadex G-50, mobile phase: solution B: 20 mM $NaNO_3$) and diluted with the solution B to give a stock solution with a lipid concentration of 10 mM (assuming 100% of lipid was incorporated into liposomes).

Figure 10:
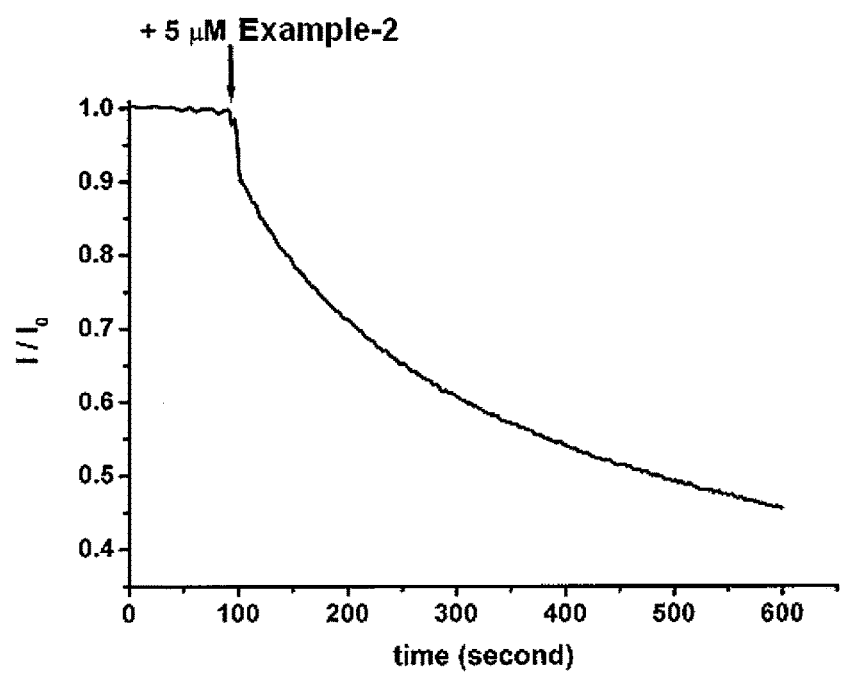
FIG. 10 shows the chloride transport activity of Example 2 in liposome with chloride-sensitive fluorescent indicator SPQ.

Fluorescent Assay:

Typically, 100 μL of SPQ-loaded vesicles (stock solution) was suspended in 1.9 mL of solution C (200 mM NaCl) and placed into a fluorimetric cell. SPQ emission at 430 nm was monitored with excitation wavelengths at 360 nm. At 100 seconds, 20 μL of a 0.5 mM THF solution of Example 2 was added through an injection port. The results are shown in FIG. 10.

Example 47

Figure 11:
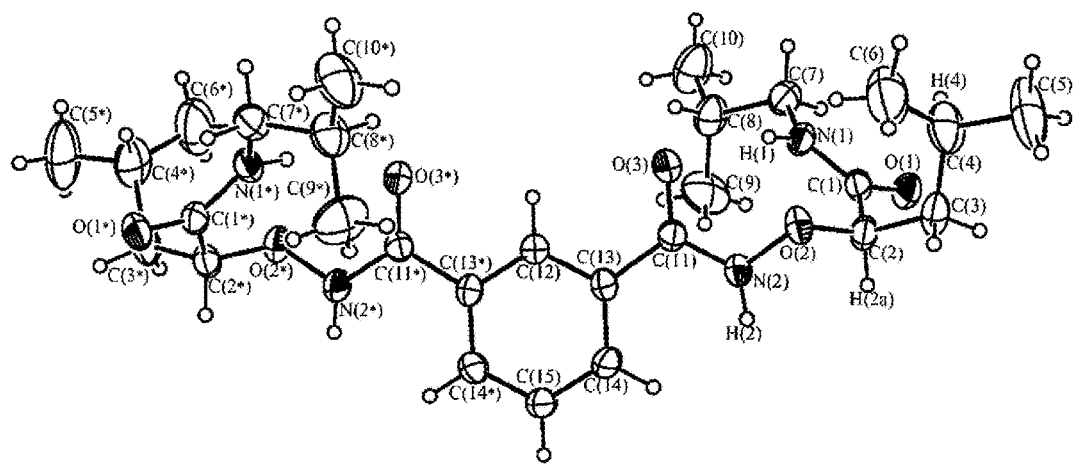
FIG. 11 shows the X-ray crystal structure of Example 2.

Example 47 shows the X-ray crystallographic analysis of example 2. The X-ray crystal structure of Example 2 is shown in FIG. 11. The other X-ray crystallographic data and data collection method are shown below.

Data Collection:

A crystal of dimensions 0.4×0.35×0.1 mm mounted on a glass fibre was used for data collection at −20° C. on a MAR diffractometer with a 300 mm image plate detector using graphite monochromatized Mo—$K_α$ radiation ($λ$=0.71073 Å). Data collection was made with 2° oscillation step of $φ$, 15 minutes exposure time and scanner distance at 120 mm. One hundred images were collected.

Crystal Data:

[$C_{28}H_{46}N_4O_6$]; formula weight=534.69, Orthorhombic, C 2 2 $2_1$, a=7.725(2) Å, b=18.967(4) Å, c=21.145(4) Å, V=3098.2(11) Å$^3$, Z=4, $D_c$=1.146 g cm$^{-3}$, μ(Mo—$K_α$)= 0.081 mm$^{-1}$, F(000)=1160, T=253 K.

TABLE 1

Crystal data and structure refinement for Example 2.

| | |
|---|---|
| Empirical formula | $C_{28}H_{46}N_4O_6$ |
| Formula weight | 534.69 |
| Temperature | 253(2) K |

TABLE 1-continued

Crystal data and structure refinement for Example 2.

| | | |
|---|---|---|
| Wavelength | 0.71073 Å | |
| Crystal system | Orthorhombic | |
| Space group | C 2 2 $2_1$ | |
| Unit cell dimensions | a = 7.725(2) Å | α = 90°. |
| | b = 18.967(4) Å | β = 90°. |
| | c = 21.145(4) Å | γ = 90°. |
| Volume | 3098.2(11) Å$^3$ | |
| Z | 4 | |
| Density (calculated) | 1.146 Mg/m$^3$ | |
| Absorption coefficient | 0.081 mm$^{-1}$ | |
| F(000) | 1160 | |
| Crystal size | 0.4 × 0.35 × 0.1 mm$^3$ | |
| Theta range for data collection | 1.93 to 25.35°. | |
| Index ranges | −7 <= h <= 7, −21 <= k <= 21, −24 <= l <= 24 | |
| Reflections collected | 7174 | |
| Independent reflections | 2039 [R(int) = 0.0498] | |
| Completeness to theta = 25.35° | 75.2% | |
| Absorption correction | None | |
| Refinement method | Full-matrix least-squares on F$^2$ | |
| Data/restraints/parameters | 2039/2/185 | |
| Goodness-of-fit on F$^2$ | 0.969 | |
| Final R indices [I > 2sigma(I)] | R1 = 0.0497, wR2 = 0.1217 | |
| R indices (all data) | R1 = 0.0707, wR2 = 0.1310 | |
| Absolute structure parameter | I(2) | |
| Largest diff. peak and hole | 0.365 and −0.284 e · Å$^{-3}$ | |

Example 48

The physiological behaviors and functions of the synthetic chloride channel formed by Example 2 in terms of its contributions to cell membrane potentials was investigated according to the following procedure. To avoid the interferences from natural ion channels, liposomes and artificial lipid bilayer vesicles were used as a model system to assess the capacity of Example 2 to vary membrane potential.

Figure 12A:
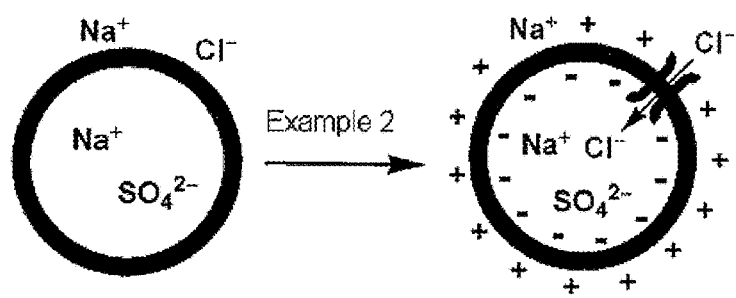
FIG. 12A depicts the change of membrane potential of a liposome after Example 2 was added to the liposome.
Figure 12B:
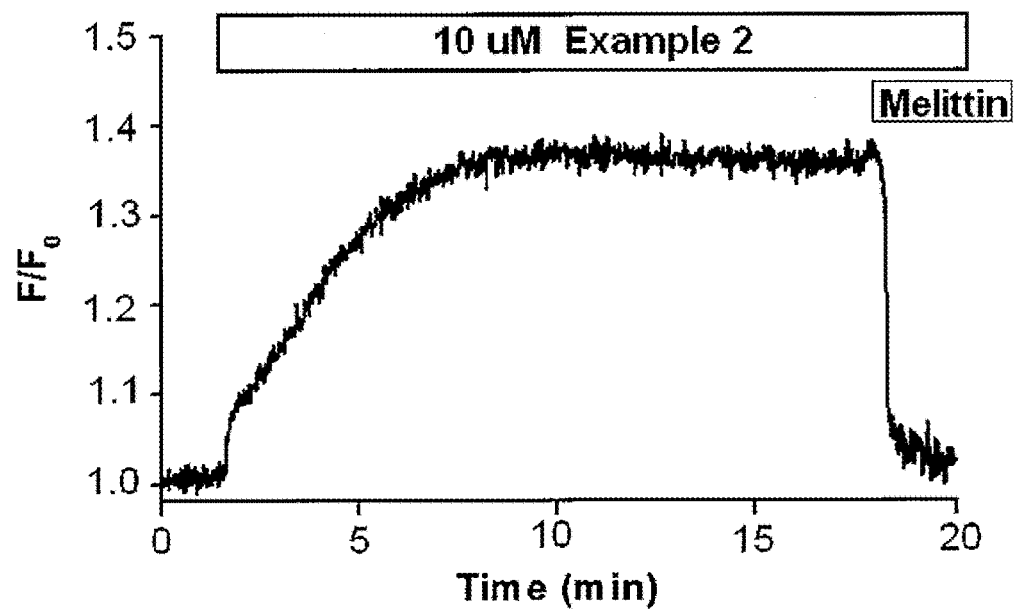
FIG. 12B shows the change of fluorescence intensity at different times (min) after Example 2 was added to the liposome.
Figure 12C:
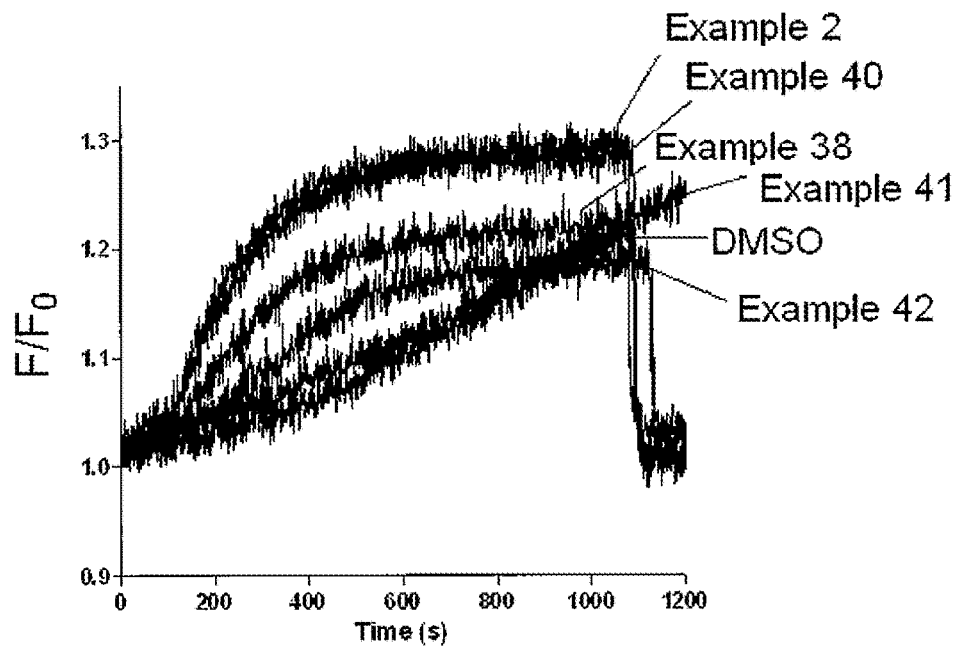
FIG. 12C-12J shows the change of fluorescence intensity at different times (min) after Examples 10-42 were added to the liposome.
Figure 12D:
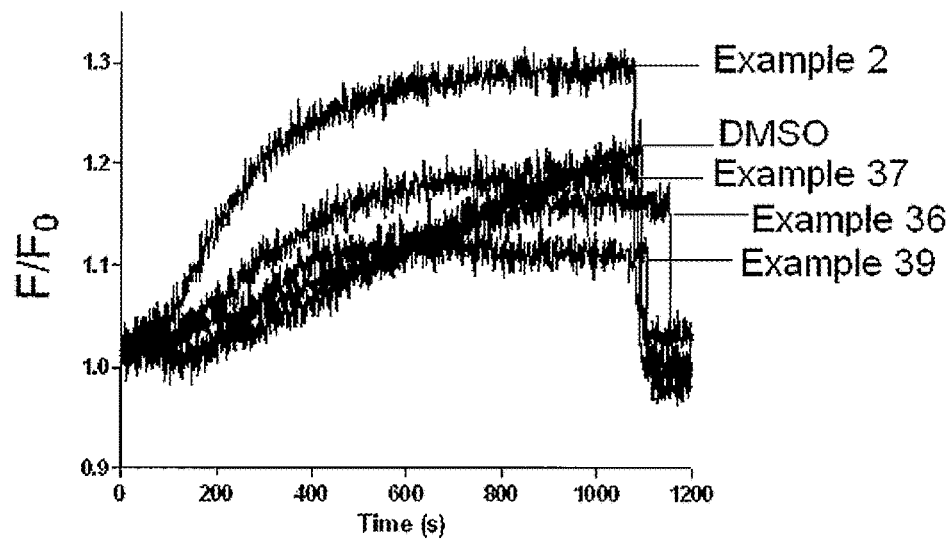
Figure 12E:
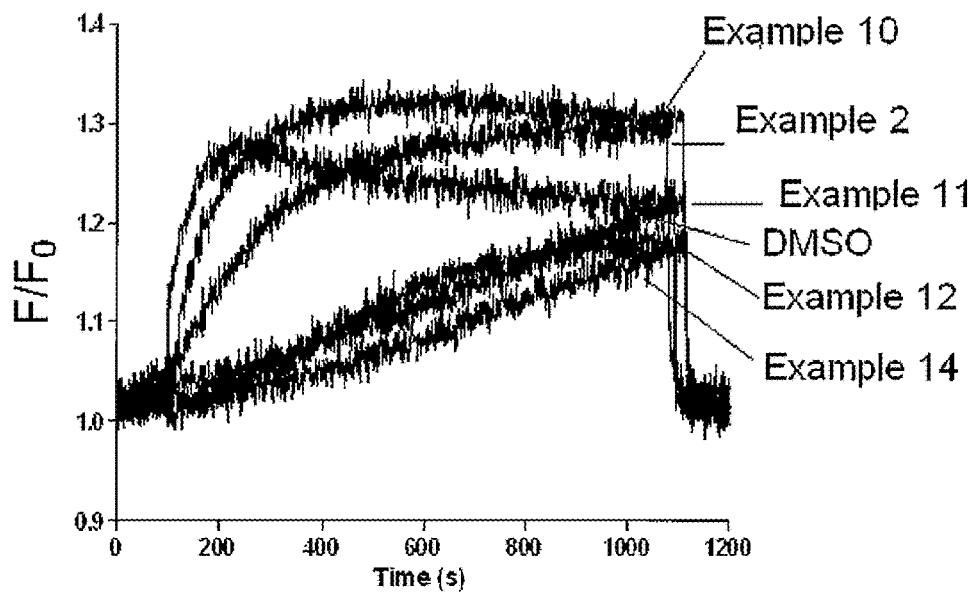
Figure 12F:
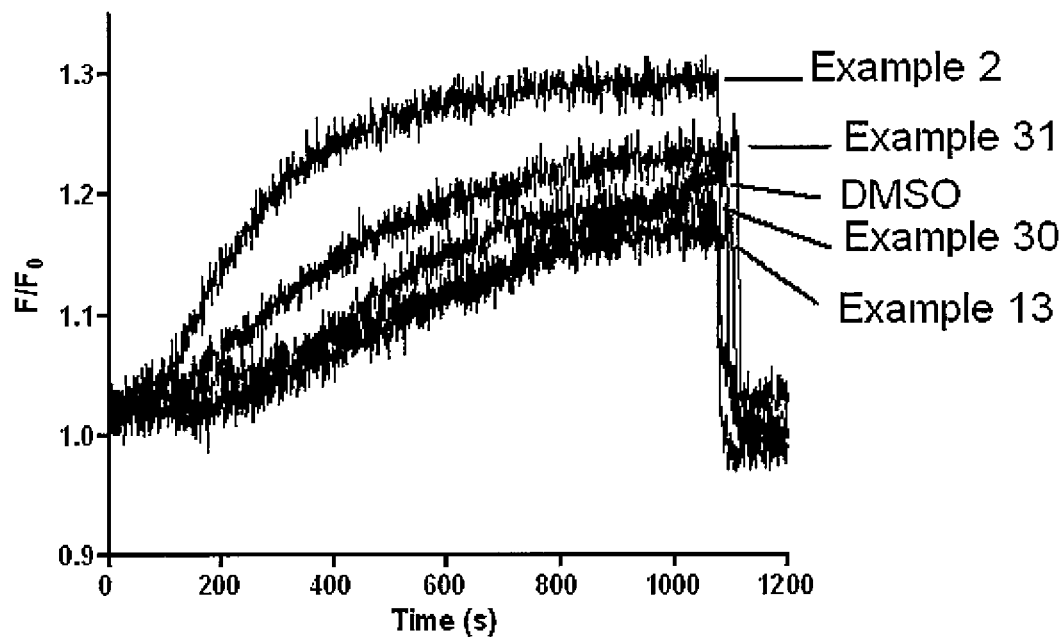
Figure 12G:
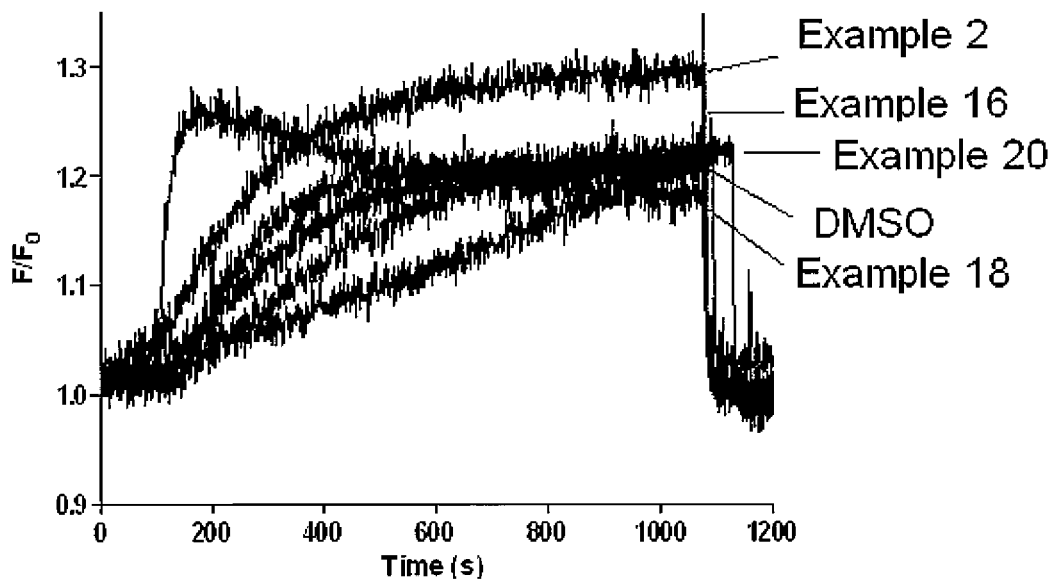
Figure 12H:
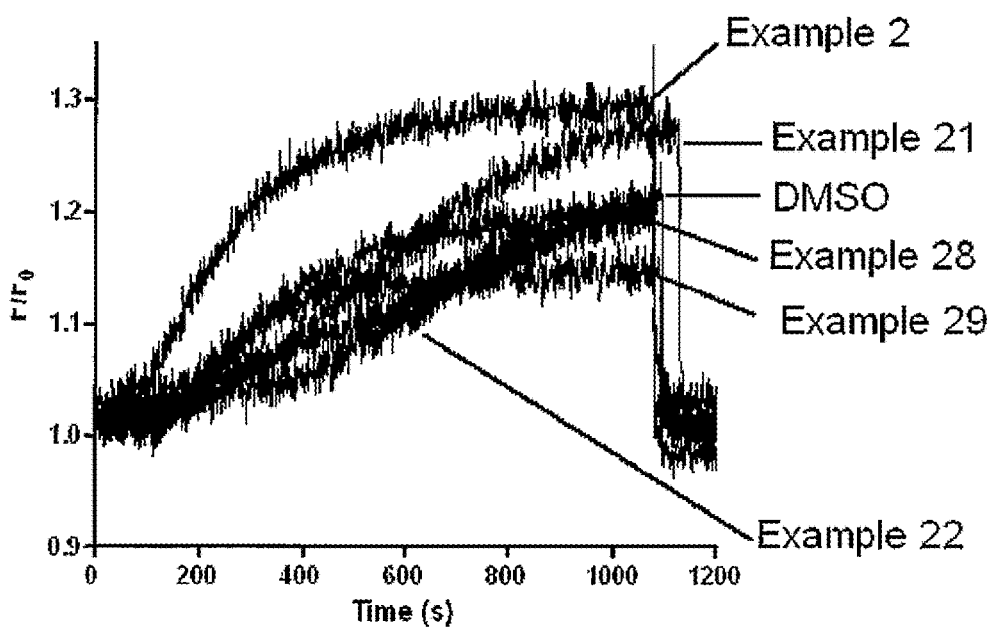
Figure 12I:
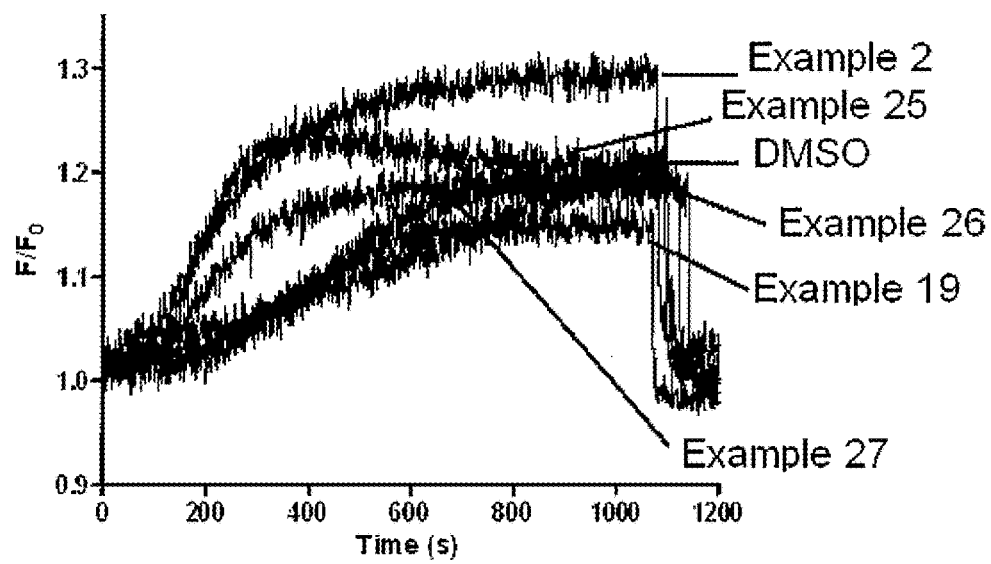
Figure 12J:
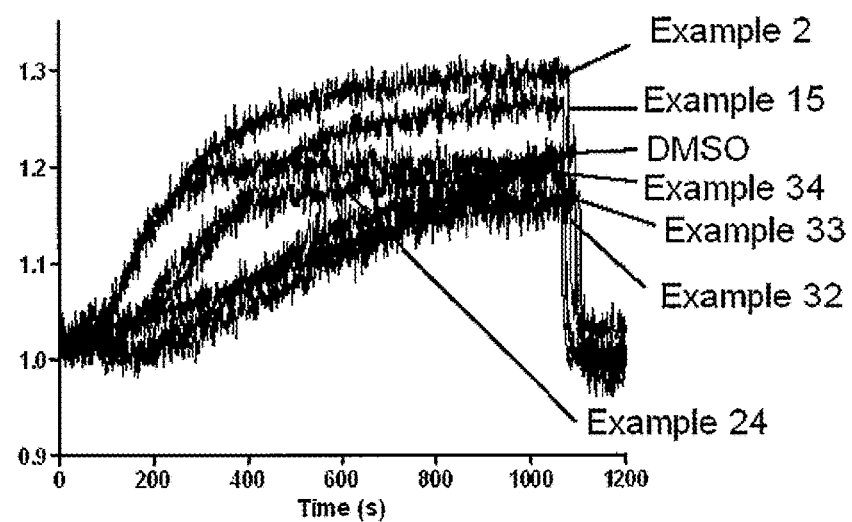

Referring to FIG. 12A, the egg yolk phosphatidylcholine (EYPC) liposomes containing sodium sulfate ($Na_2SO_4$) were suspended in an isotonic sodium chloride (NaCl) extravesicular solution with a membrane potential sensitive dye, i.e., safranin O. As shown in FIG. 12B, addition of Example 2 to the liposome suspensions induced a rapid increase in fluorescence intensity of safranin O, indicating the formation of stable negative charge inside liposomes. This may be due to the fact that Example 2 can only mediate chloride rather than sulfate or sodium ions transporting across lipid bilayers. While Example 2 mediated chloride ions flowing into the liposomes, the interiors of the liposomes become progressively more negative relative to the exteriors. FIG. 12C-12J shows that in addition to Example 2, Examples 10-42 can also modulate membrane potentials of liposomes with different efficiencies.

Example 49

Figure 13A:
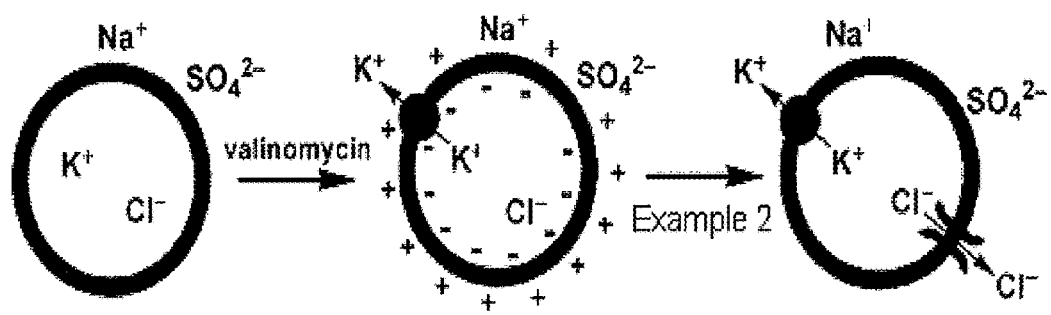
FIG. 13A depicts the change of membrane potential of a liposome after (1) valinomycin and (2) Example 2 were added to the liposome.
Figure 13B:
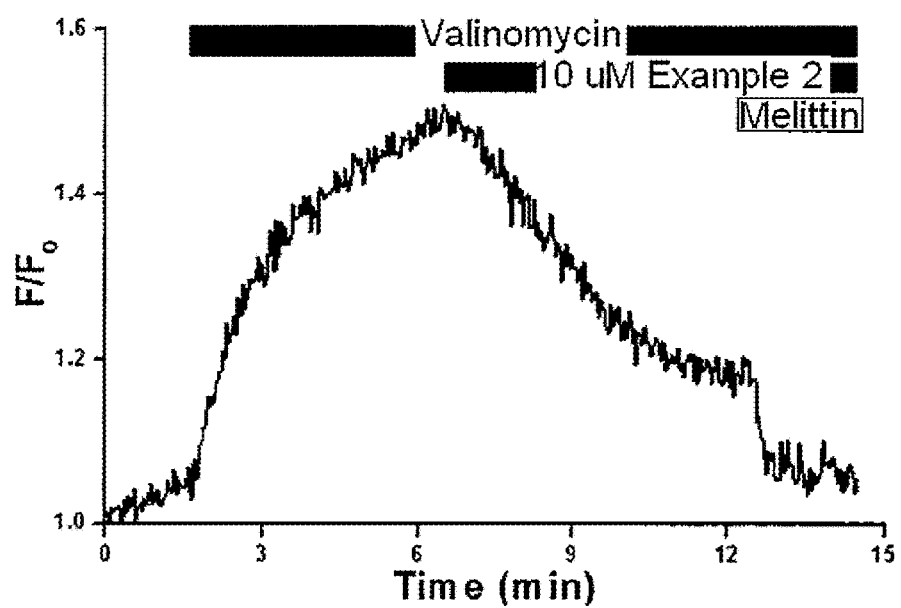
FIG. 13B shows the change of fluorescence intensity at different times (min) after the valinomycin and Example 2 were added to the liposome.

The ability of Example 2 to modulate membrane potentials in polarized liposomes was investigated. In the assay as shown in FIG. 13A, the EYPC-liposomes encapsulating potassium chloride (KCl) were suspended in an isotonic mixture of KCl and $Na_2SO_4$ solution to produce a transmembrane K$^+$ concentration gradient. External addition of the selective K$^+$ carrier valinomycin resulted in K$^+$ efflux, which polarized the liposome by establishing an inside negative membrane potential. The assay was completed by the application of Example 2 and the membrane potential was monitored by changes of the fluorescence intensity of extravesicular safranin O. As shown in FIG. 13B, Example 2 rapidly depolarized the EYPC-liposomes. This depolarization process induced by Example 2 may be attributed to the formation of chloride channels by Example 2 that mediate chloride ions flow out of the polarized liposomes to balance the electrostatic potential established by valinomycin.

Example 50

Figure 14A:
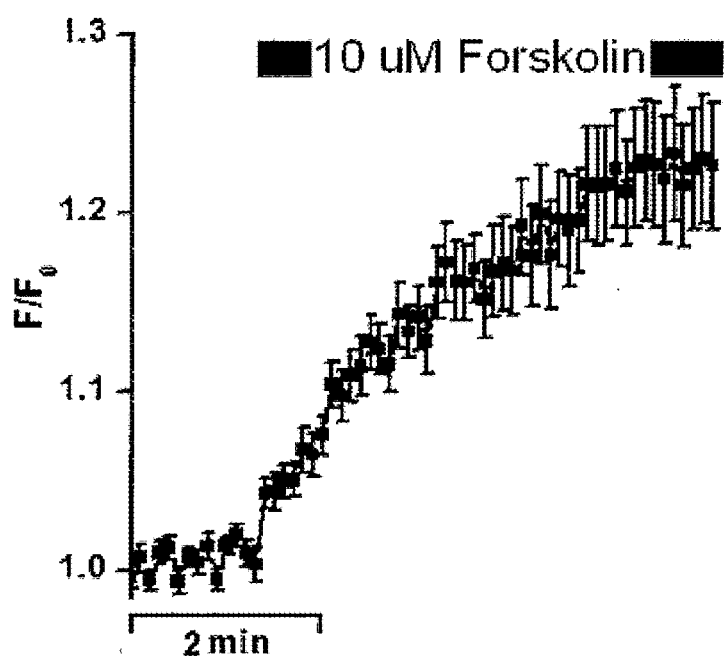
FIG. 14A-E depict the changes of fluorescence intensity of the membrane potential of Madin-Darby canine kidney (MDCK) cells at different times (min) after (A) 10 μM of forskolin; (B) 10 μM of Example 2; (C) 100 mL of Cl$^-$ and 10 μM of Example 2; (D) 1 mM of diphenylamine-2-carboxylate (DPC) and 10 μM of Example 2; (E) 60 mM of Cl$^-$, 1 mM of DPC, and 10 μM of Example 2, were added to the MDCK cells, respectively.

To determine the potential of Example 2 for application in biological and medicinal science, Example 2 was investigated for incorporating into the plasma membranes of living cells and, thereby, modulating their membrane potentials by increasing chloride permeability of the cell membranes. A potential-sensitive dye his-oxonal was used to measure the relative changes in membrane potential of the Madin-Darby canine kidney (MDCK) cells, a model for the renal distal tubule and collecting duct that secrete chloride ions. An increase in fluorescence of bis-oxonal indicated cell depolarization while a decrease indicated hyperpolarization. The treatment of MDCK cells with forskolin, an agonist of intracellular cyclic AMP that can activate CFTR chloride channels in the cells, produced a moderate increase in fluorescence of bis-oxonal indicating depolarization of the cells (FIG. 14A). This depolarization effect could be ascribed to that the chloride equilibrium potential ($E_{Cl}$) was higher than the resting membrane potential in MDCK cells. Thus, the opening of chloride channels shifted the membrane potential towards the $E_{Cl}$. As expected, application of Example 152 also showed a similar depolarization effect on the membrane potential (FIG. 14B), which was consistent with the capacity of Example 2 to increase chloride permeability in MDCK cells by forming chloride channels. As shown in FIG. 14C, reducing extracellular chloride concentration elicited intracellular chloride efflux through a positive shift in the $E_{Cl}$ and, therefore, depolarized the membrane potential. Interestingly, addition of Example 2 obviously facilitated this depolarization process by increasing cell chloride permeability. In addition, despite of the existence of a natural chloride channel blocker, diphenylamine-2-carboxylate (DPC), which entirely inhibited the depolarization effect induced by low-chloride extracellular solution, Example 2 depolarized the cells by restoring chloride permeability of the cell membranes (FIGS. 14D and 14E). These results confirmed the ability of Example 2 to modulate membrane potentials of living cells through forming artificial chloride channels independent of natural ones.

Figure 14B:
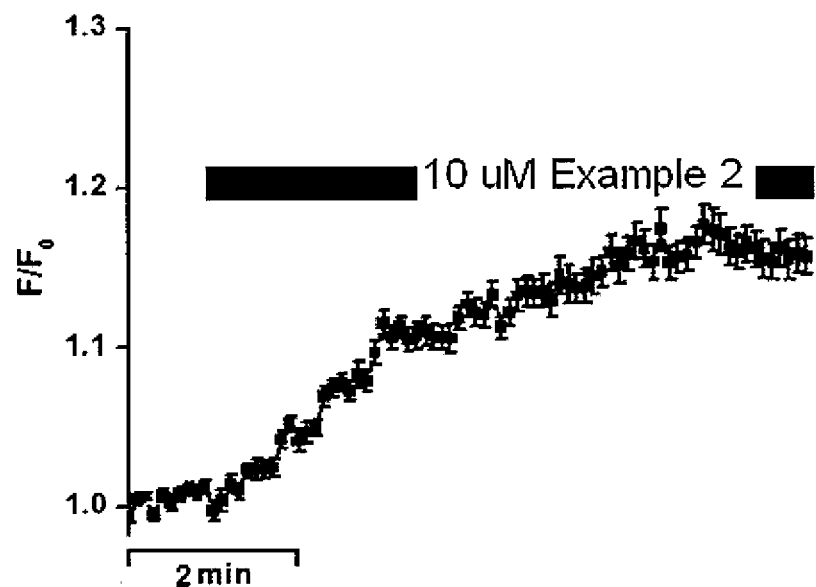
Figure 14C:
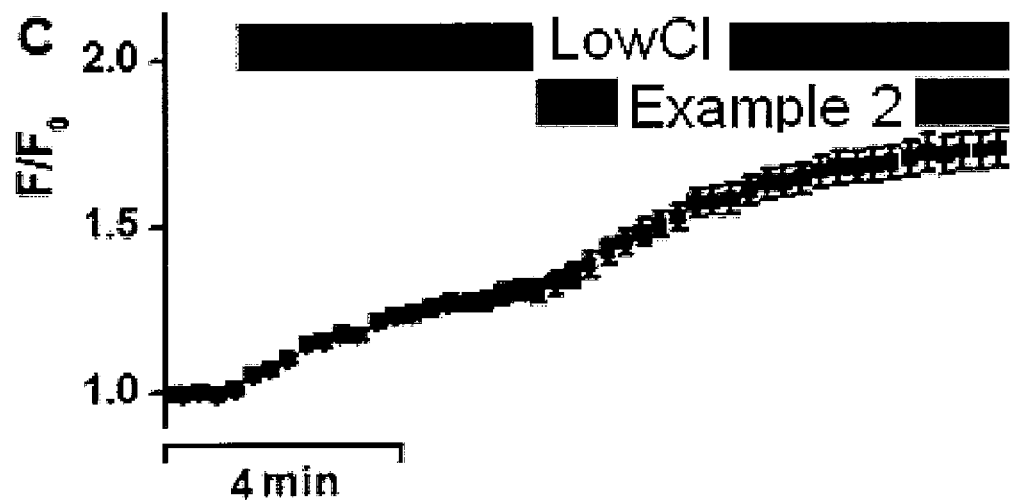
Figure 14D:
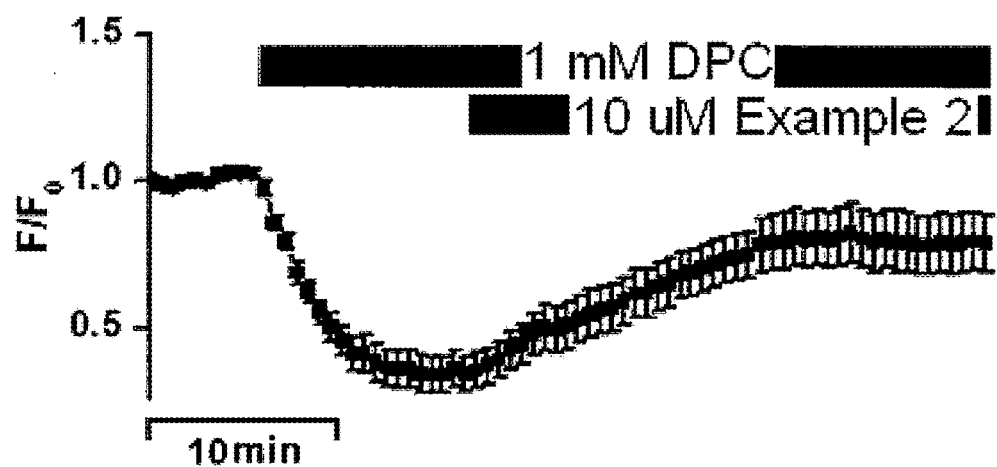
Figure 14E:
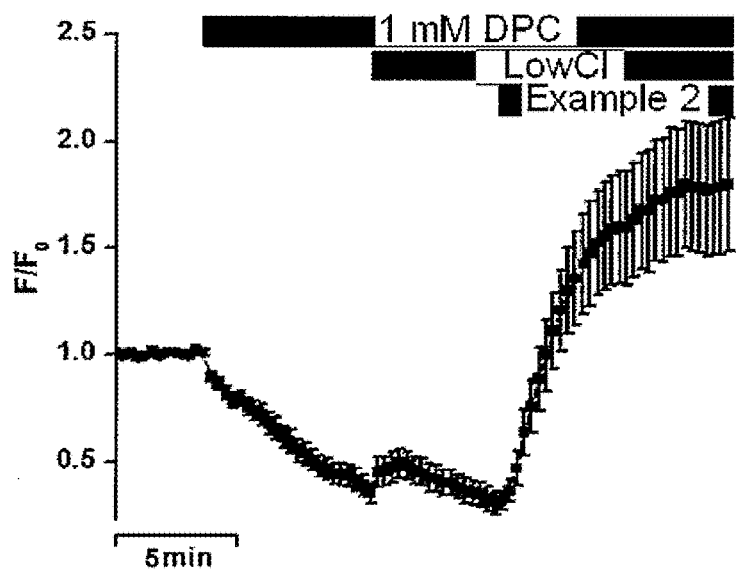

In summary, FIG. 14A-E show the effects of adding different substances, including Example 2, on the membrane potential of Madin-Darby canine kidney (MDCK) cells. Membrane potentials of MDCK cells were monitored by the changes of emission intensity of the potential-sensitive dye bis-oxonol (DiBAC4(3)). The increase in the fluorescence intensity indicates depolarization. FIG. 14A shows that the addition of 10 μM foskolin resulted in significant depolarization of the membrane potential of MDCK cells. FIG. 14B shows the addition of 10 μM of Example 2 resulted in depolarization of the membrane potential of MDCK cells. FIG. 14C shows that the perfusing the MDCK cells with relatively low chloride (100 mM chloride) solution, assisted by addition of 10 μM of Example 2, resulted in slight depolarization of the membrane potential of MDCK cells. FIG. 14D shows that the addition of 1 mM DPC resulted in hyperpolarization of the membrane potential, and the subsequent addition of 10 μM of Example 2 resulted in a shift of the hyperpolarized membrane potential toward the original resting potential. FIG. 14E shows that perfusing the MDCK cells with low Cl⁻ (60 mM Cl⁻) Ringer's solution in the presence of 1 mM DPC did not result in depolarization of the membrane potential of MDCK cells, but subsequent addition of 10 μM Example 2 resulted in depolarization of such membrane potential. Each point in FIG. 14A-E represents the mean±s.e. (n=20-80 cells in 4-6 experiments).

Example 51

Figure 15A:
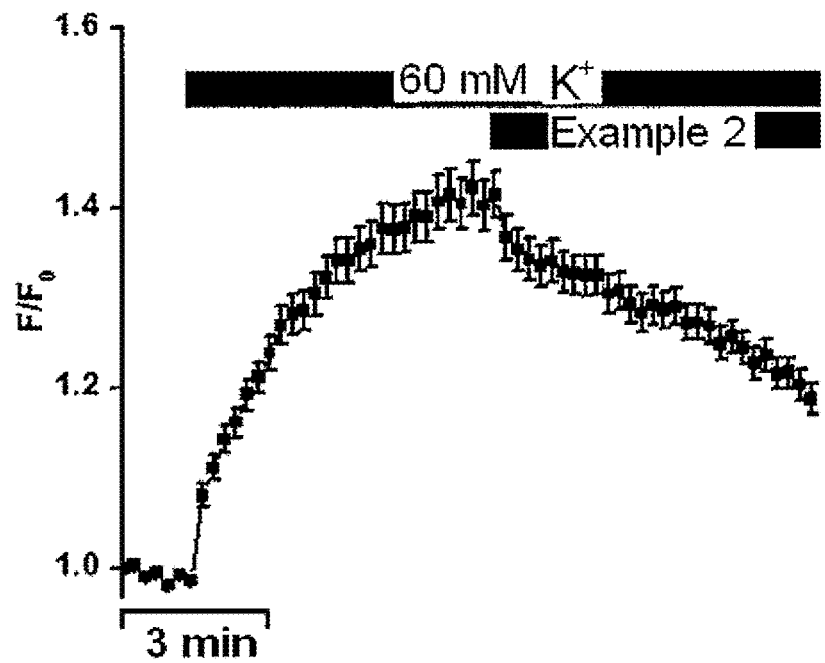
FIG. 15A depicts the changes of the membrane potential of the A7r5 cells at different times (min) after the A7r5 cells are sequentially treatment with 60 mM K$^+$ solution and 10 μM of Example 2.
Figure 15B:
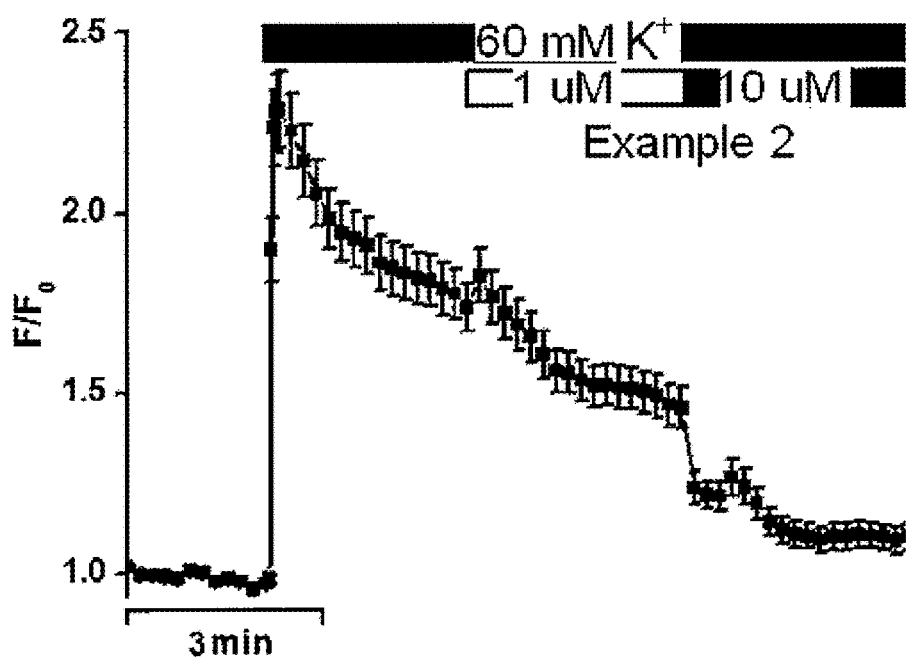
FIG. 15B depicts the changes of [Ca$^{2+}$] of the A7r5 cells at different times (min) after the A7r5 cells are sequentially treatment with 60 mM K$^+$ solution, 1μ of Example 2, and 10 μM of Example 2.

It is well known that the rise in intracellular $Ca^{2+}$ triggers a variety of cellular functions, e.g., the release of neurotransmitters from nerve terminals and muscle contraction. The voltage-gated $Ca^{2+}$ channels that mediate $Ca^{2+}$ influx across the plasma membrane serve as one of important pathways to regulate the intracellular $Ca^{2+}$ concentration ($[Ca^{2+}]_i$) in vascular smooth muscle cells. The artificial chloride channel formed by Example 2 was investigated for regulating natural voltage-gated $Ca^+$ channels by modulating membrane potential in vascular smooth muscle cells. The rat thoracic aortic smooth muscle cell line A7r5 was used to elucidate the effect of Example 2 on the membrane potential and the $[Ca^{2+}]_i$ of vascular smooth muscle cells. As shown in FIGS. 15A and 15B, the treatment of the smooth muscle cells with 60 mM $K^+$ (high-K) extracellular solution strongly depolarized the membrane potential and stimulated a dramatic increase in the $[Ca^{2+}]_i$, because high-K extracellular solution, through a positive shift in the $K^+$ equilibrium potential ($E_K$), could depolarize cell membrane potential to activate the voltage-gated L-type $Ca^2$ channels, and therefore, could rise the $[Ca^{2+}]_i$. However, the subsequent application of Example 2 in this high-K extracellular solution resulted in a slow decrease in the $[Ca^{2+}]_i$ to almost the original level (FIG. 15B), suggesting Example 2 may repolarize the cell membrane to deactivate the voltage-gated calcium channels. This assumed repolarization process was further confirmed by measuring cell membrane potential of A7r5 cells under the same experimental condition (FIG. 15A). This result suggested that the high-K extracellular solution depolarized the membrane potential to such extent that is not only high enough to activate the L-type $Ca^{2+}$ channels but also much higher than the $E_{Cl}$ of these cells. Consequently, Example 2 could increase the chloride permeability and thus shift the membrane potential back (i.e. repolarize the membrane potential) toward $E_{Cl}$ that is likely lower than the activation potential of L-type $Ca^{2+}$ channels in these cells. Furthermore, the prior application of Example 2 showed no obvious effect on both the membrane potential and the $[Ca^{2+}]_i$ of A7r5 cells, implying that the $E_{Cl}$ was close to the resting membrane potential of the cells. In addition, the high-K induced effect on the membrane potential and the $[Ca^{2+}]$ was remarkably inhibited by the pretreatment of the cells with Example 2. This result revealed that through increasing chloride permeability, Example 2 could balance the depolarization effect elicited by the positively shifted $E_K$. Taken together, Example 2 may serve as the first synthetic ion channel that regulates $[Ca^{2+}]_i$ by modulating membrane potential in living cells.

FIG. 15A-B, 16A-B show the effects of Example 2 and 60 mM $K^+$ extracellular solution (high-$K^+$ solution) on regulating the membrane potential and the $[Ca^{2+}]$ of smooth muscle cells (A7r5 cells). It can be seen that the treatment of the A7r5 cells with high-$K^+$ solution resulted in strong depolarization of the membrane potential (FIG. 15A) and a dramatic increase in the $[Ca^+]$ (FIG. 15B). Subsequent addition of 10 uM of Example 2 resulted in repolarization of the membrane potential, as shown in FIG. 15A, and a slow decrease in the [Ca$^{2+}$] to almost the original level, as shown in FIG. 15B. Each point represents the mean±s.e. (n=20-80 cells in 4-6 experiments).

Figure 16A:
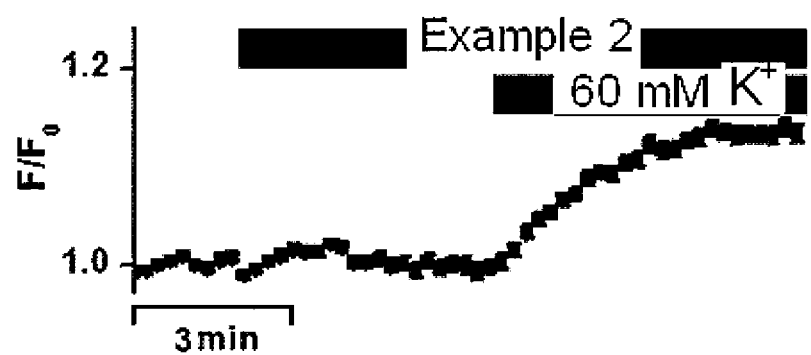
FIG. 16A-B depict the changes of the membrane potential and [Ca$^{2+}$] respectively of the A7r5 cells at different times (min) after the A7r5 cells are sequentially treatment with 10 μM of Example 2 and 60 mM K$^+$ solution.
Figure 16B:
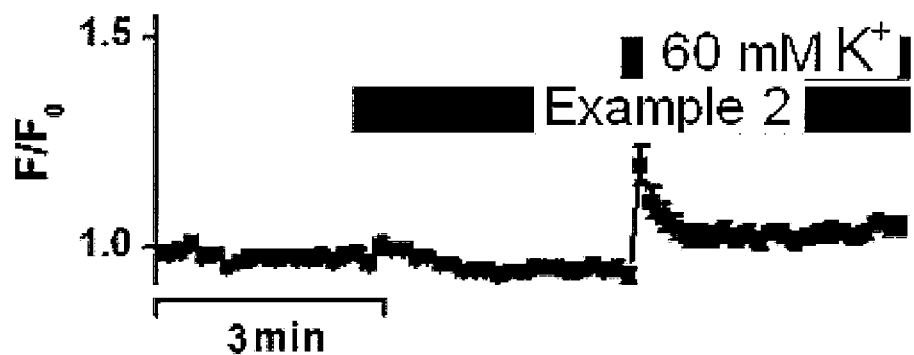

FIG. 16A-B show that the prior treatment of Example 2 on A7r5 cells resulted in no obvious depolarization effect nor change in the [Ca$^{2+}$]. The subsequent addition of high-K solution resulted in a much weaker depolarization effect compared with those treated without the presence of Example 2, as shown in FIG. 15A-B. Each point represents the mean±s.e. (n=20-80 cells in 4-6 experiments).

Example 52

Figure 17A:
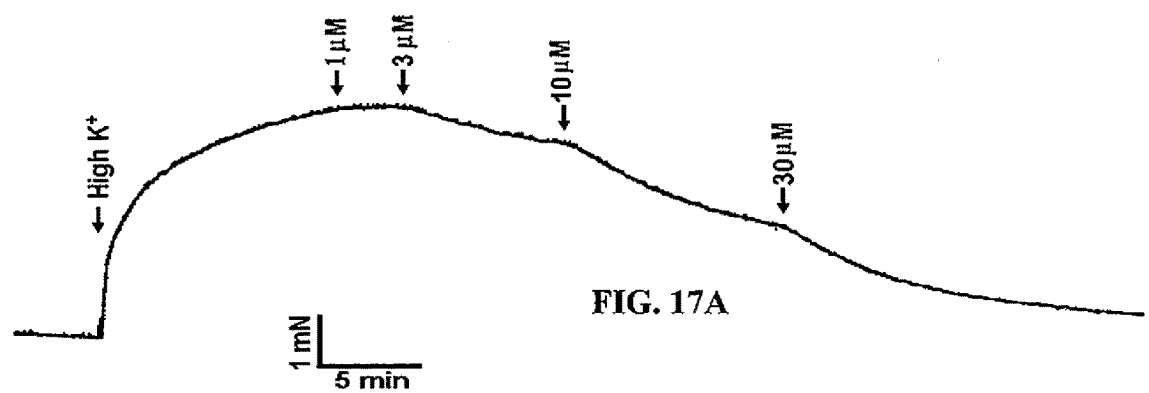

Example 52 was for investigating whether Example 2 could promote vasorelaxation during vasoconstriction induced by depolarization. Mouse thoracic aortic rings was mounted in an organ bath apparatus and measured their muscular activity. FIG. 17A shows a typical experiment in which increasing the concentrations of Example 2 from 1 to 30 uM induced the complete relaxation of mouse aortic rings preconstricted by high-K solution. Example 2 produced concentration-dependent relaxation of preconstricted aortic rings with half-maximal relaxation value IC$_{50}$ of 8.42±0.18 uM (n=5).

Figure 17B:
Figure 17C:
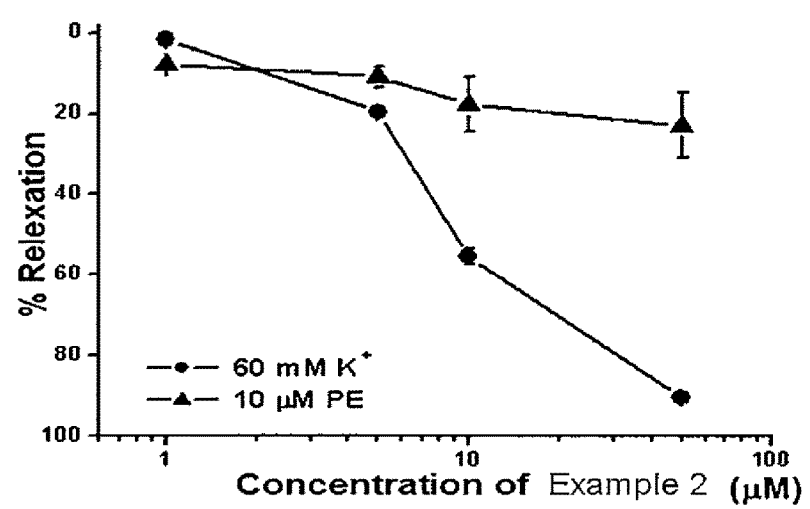
FIG. 17C depicts the relationships between the concentrations of Example 2 and the vasorelaxant effects on mouse aorta preconstricted by the 60 mM K$^+$ solution (●) and the 10 μM of PE (▲), respectively.

Example 52 was for investigating whether Example 2 could induce muscle contraction by activating α-adrenergic receptor. To verify that the vasorelaxant action of Example 2, Example 2 was tested to relax the mouse aortic rings constricted by the α-adrenergic receptor agonist phenylephrine (PE). FIG. 17B shows that Example 2 failed to relax these aortic rings (n=4). This experiment indicated that Example 2 failed to reduce the [Ca$^{2+}$] by blocking the voltage-gated Ca$^2$ channels.

In addition to the effect of Example 2 on modulating membrane potential and regulating [Ca$^{2+}$]$_i$, Example 2 may lead to relaxation of preconstricted mouse aortic rings by repolarizing membrane potential to deactivate voltage-gated Ca$^{2+}$ channels in smooth muscle cells, paralleling with the proposed functional role played by cystic fibrosis transmembrane conductance regulator (CFTR) chloride channels in smooth muscle cells in controlling the vascular tone. This effect also underlies the possibility of using synthetic chloride channels to treat hypertension.

As demonstrated above, embodiments herein provide various self-assembling compounds which are useful for making ion-channel compositions and membranes comprising same. While this disclosure has been described with respect to a limited number of embodiments, the specific features of one embodiment should not be attributed to other embodiments of the invention. No single embodiment is representative of all aspects of the invention. In some embodiments, the compositions or methods may include numerous compounds or steps not mentioned herein. In other embodiments, the compositions or methods do not include, or are substantially free of, any compounds or steps not enumerated herein. Variations and modifications from the described embodiments exist. For example, the ion-channel compositions disclosed herein need not comprising only self-assembling compounds. It can comprise any type of compounds generally suitable for ion-channel compositions. It is noted that the methods for making and using the ion-channel compositions disclosed herein are described with reference to a number of steps. These steps can be practiced in any sequence. One or more steps may be omitted or combined but still achieve substantially the same results. The appended claims intend to cover all such variations and modifications as falling within the scope of the invention.

All publications and patent applications mentioned in this specification are herein incorporated by reference to the same extent as if each individual publication or patent application was specifically and individually indicated to be incorporated by reference. It is to be understood that this disclosure has been described in detailed by way of illustration and example in order to acquaint others skilled in the art with the invention, its principles, and its practical application. Further, the specific embodiments provided herein as set forth are not intended to be exhaustive or to limit the disclosure, and that many alternatives, modifications, and variations will be apparent to those skilled in the art in light of the foregoing examples and detailed description. Accordingly, this disclosure is intended to embrace all such alternatives, modifications, and variations that fall within the spirit and scope of the following claims. While some of the examples and descriptions above include some conclusions about the way the compounds, compositions and methods may function, the inventors do not intend to be bound by those conclusions and functions, but put them forth only as possible explanations in light of current understanding.

What is claimed is:

1. A method of modulating membrane potential of a cell membrane comprising:

forming a synthetic chloride ion channel in the cell membrane;

wherein the synthetic ion channel is formed by a plurality of molecules of a self-assembling compound having formula:

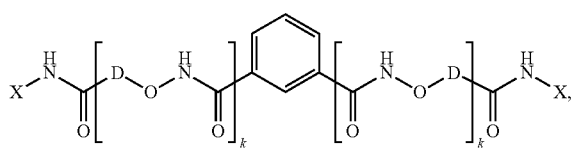

wherein D is CH(R) wherein R is:
(1) C$_{1-6}$ alkyl optionally substituted with NH$_2$;
(2) (C$_{1-6}$ alkyl)C(=O)(OC$_{1-6}$ alkyl);
(3) (C$_{1-6}$ alkyl)S(C$_{1-6}$ alkyl);
(4) (C$_{0-6}$ alkyl)phenyl; or
(5) indolyl;

X is C$_{1-20}$ alkyl; and k is 1.

2. The method of claim 1, wherein the synthetic ion channel is formed by a plurality of molecules of a self-assembling compound having formula
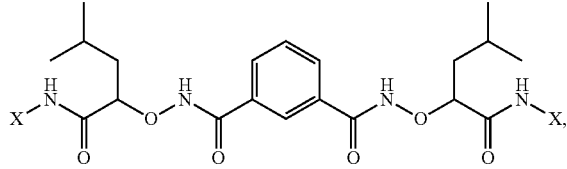
wherein X is $C_{1-20}$ alkyl.
3. The method of claim 1, wherein X is isobutyl.
4. The method of claim 2, wherein the self-assembling compound is
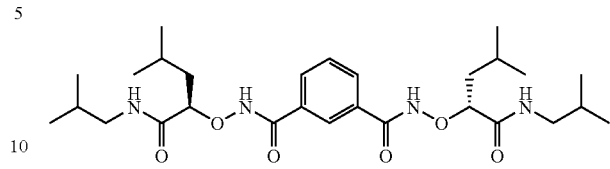
or a salt or stereoisomer thereof.
5. The method of claim 2, in which the self-assembling compound is:
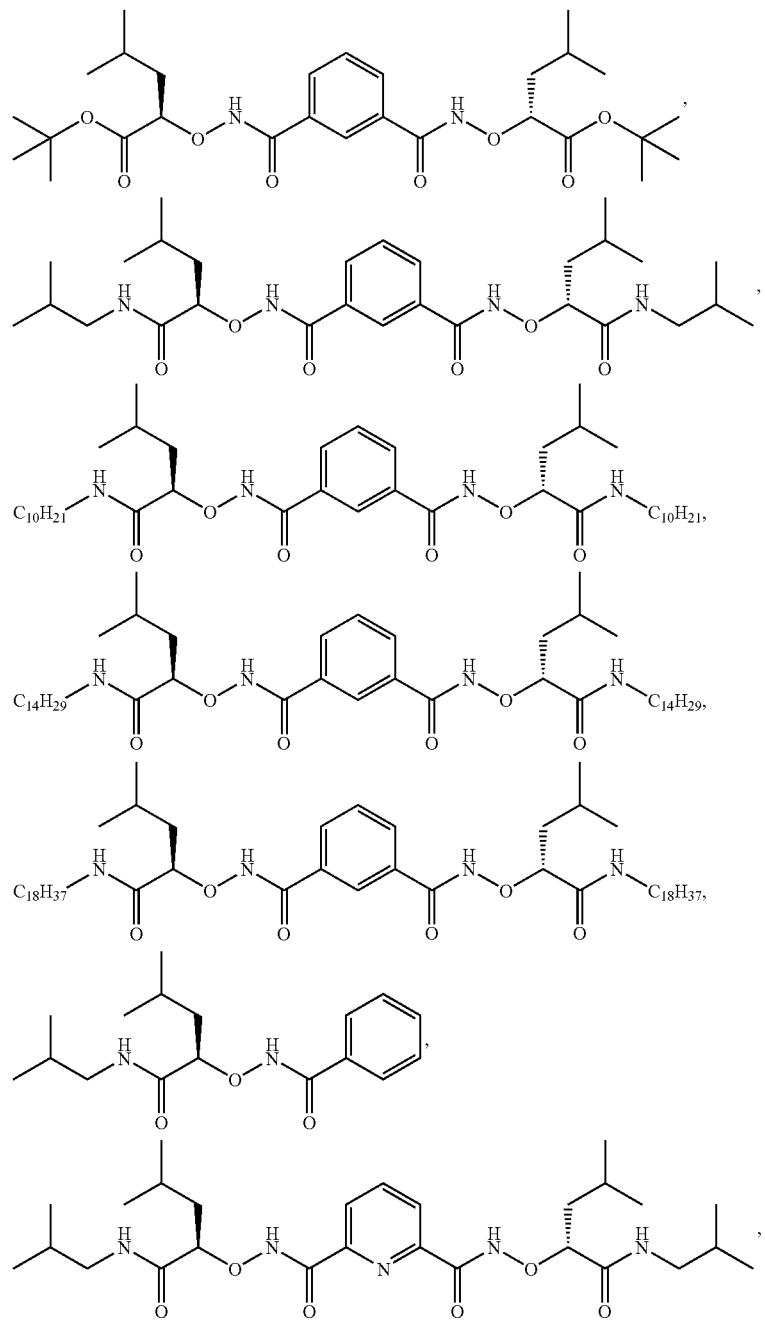

-continued
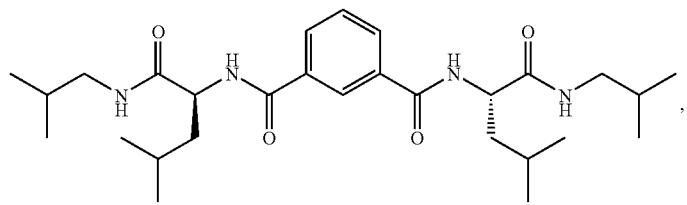
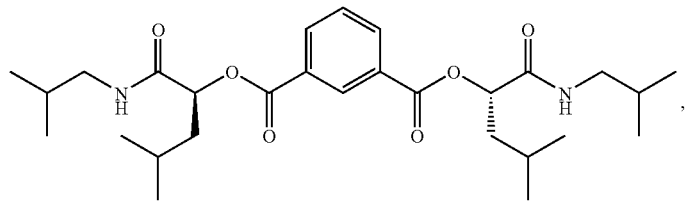
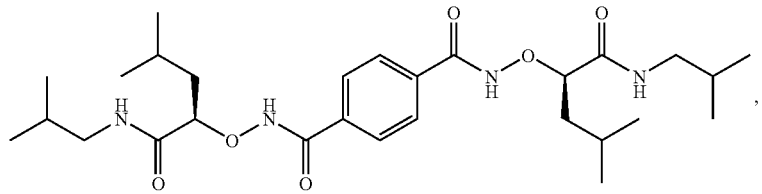
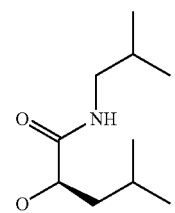
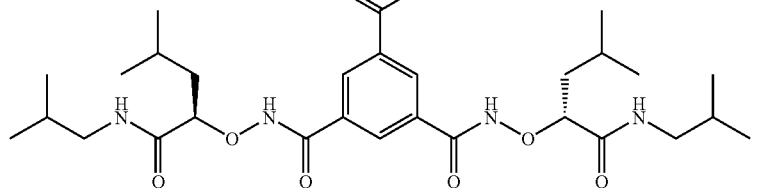
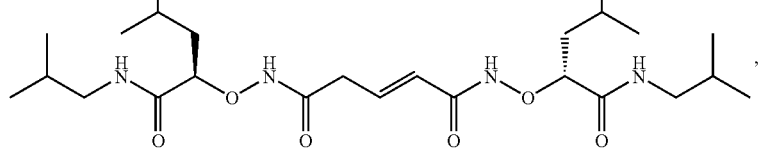
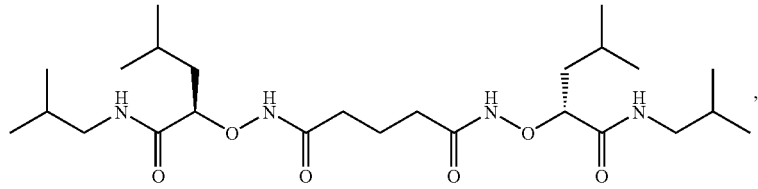
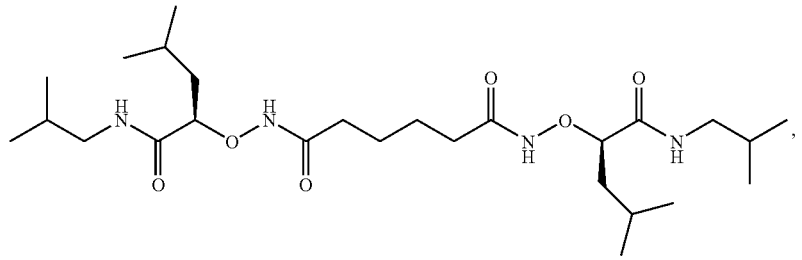

-continued
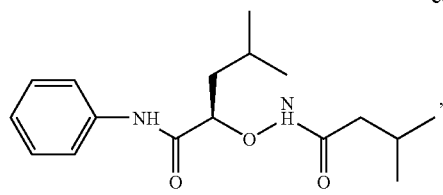
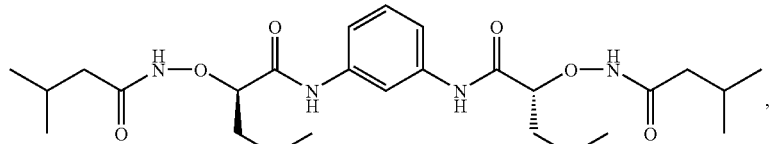
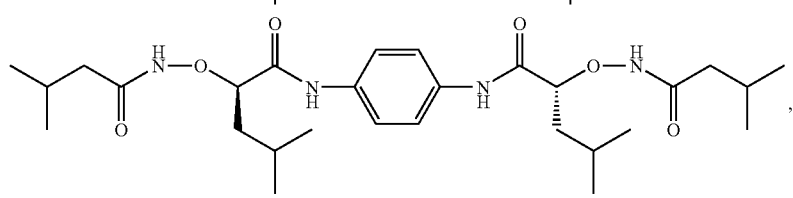
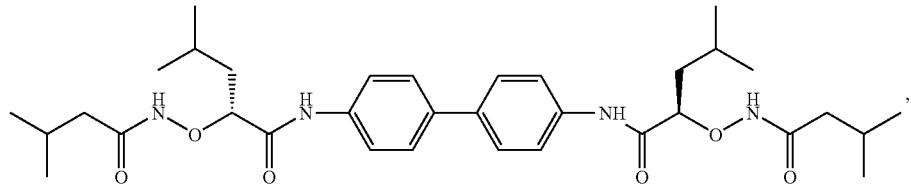
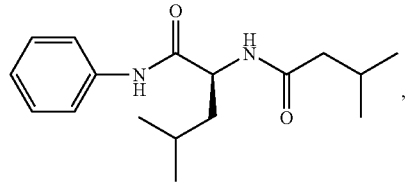
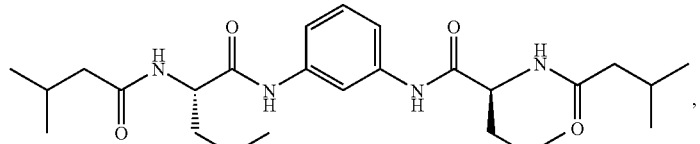
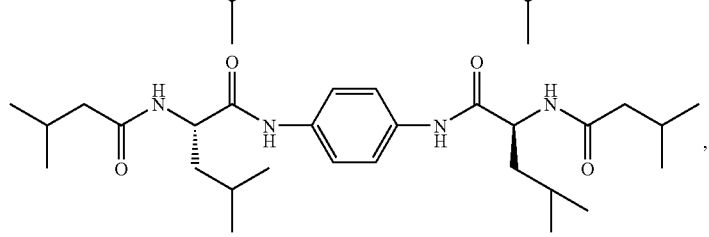
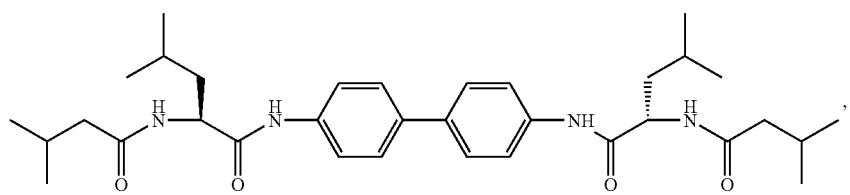
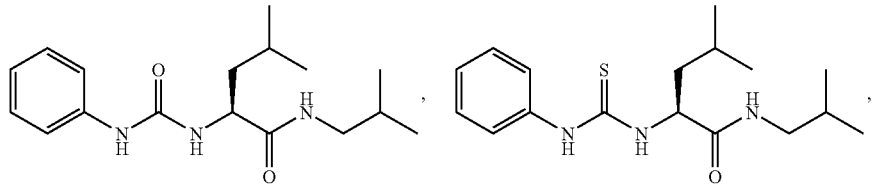

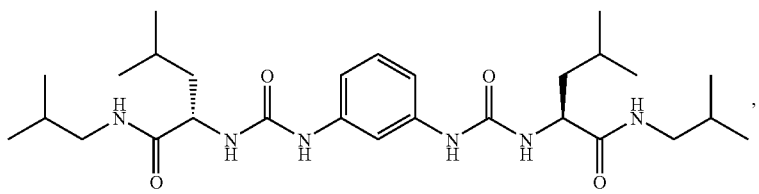,
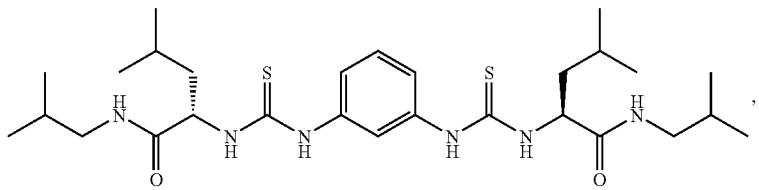,
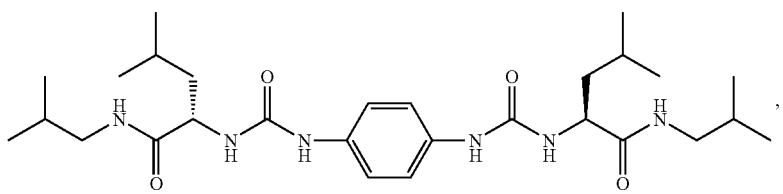,
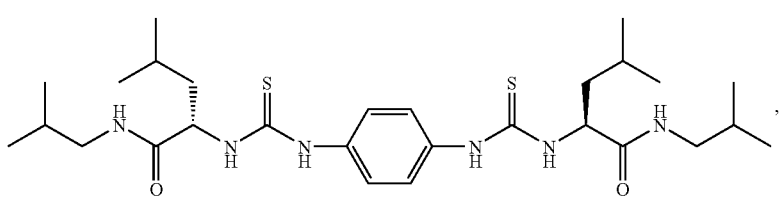,
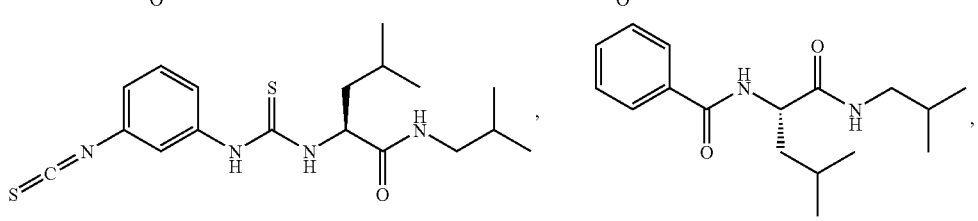,
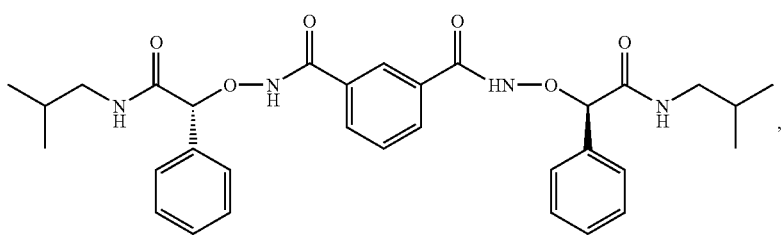,
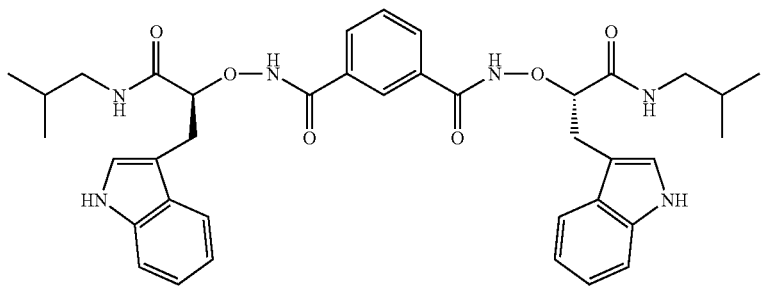,
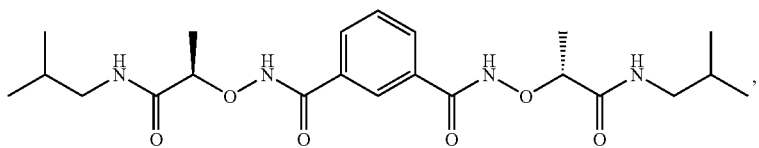, -continued
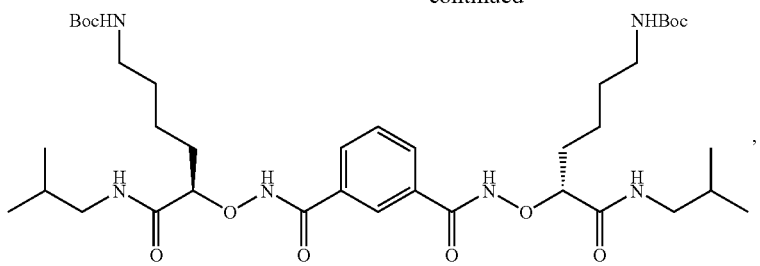
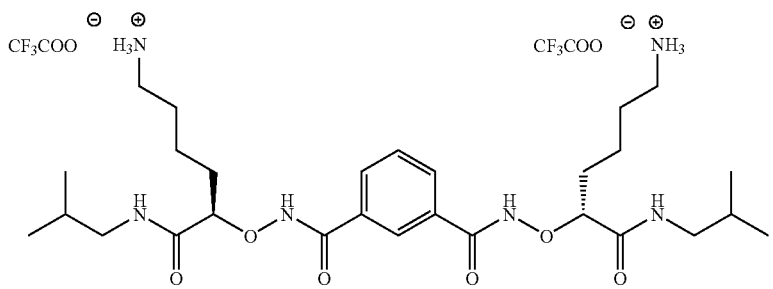
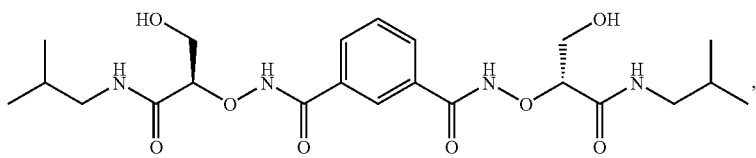
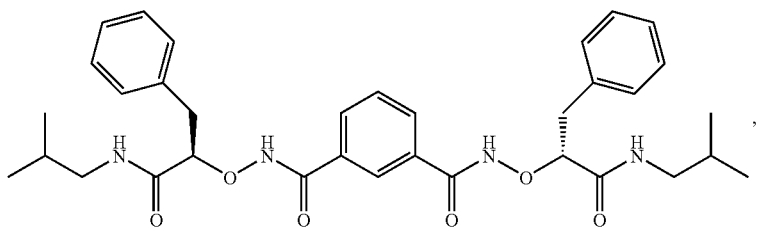
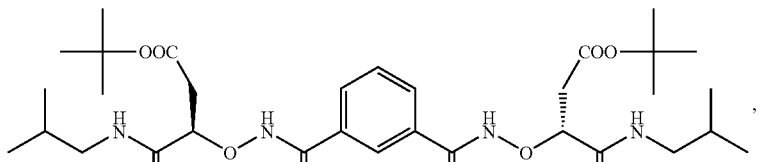
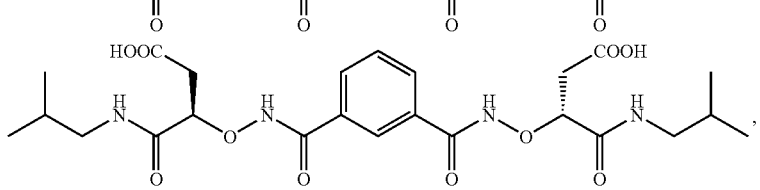
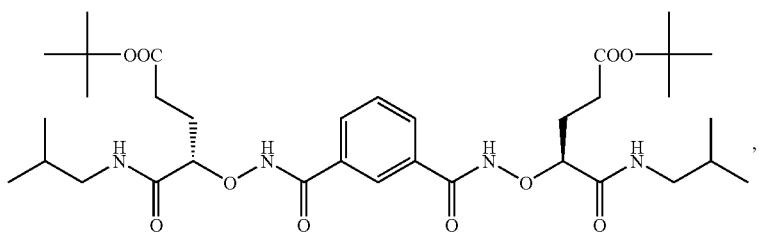

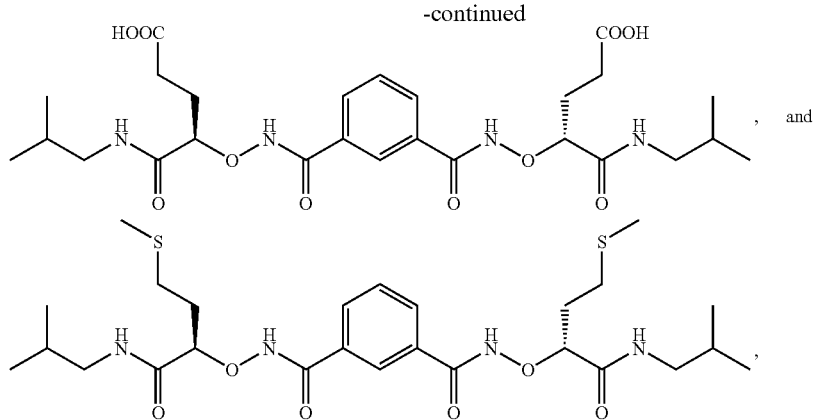
or any salt or stereoisomer of any thereof.
* * * * *

UNITED STATES PATENT AND TRADEMARK OFFICE
CERTIFICATE OF CORRECTION

PATENT NO. : 9,610,263 B2
APPLICATION NO. : 12/337642
DATED : April 4, 2017
INVENTOR(S) : Dan Yang et al.

Page 1 of 4

It is certified that error appears in the above-identified patent and that said Letters Patent is hereby corrected as shown below:

In the Specification

Column 1,
Line 6, "to U.S." should read --to copending U.S.--.

Column 7,
Line 66, "FIG. 15B depicts" should read --FIG. 16B depicts--.

Column 8,
Line 7, "FIG. 17A-13" should read --FIG. 17A-B--.

Column 11,
Line 40, ""Stercoisomer"" should read --"Stereoisomer"--.
Line 60, "K/S=30/70," should read --R/S=30/70,--.

Column 15,
Line 39, "is or" should read --is 1 or--.

Column 46,
Line 39, "$C_2H_{44}N_2O_6$" should read --$C_{28}H_{44}N_2O_6$--.

Column 47,
Line 25, "534.3417." should read --534.3417,--.

Column 48,
Line 11, "without Her" should read --without further--.

Column 51,
Line 16, "498.3417." should read --498.3417,--.
Line 32, "500.3574." should read --500.3574,--.

Signed and Sealed this
Twenty-eighth Day of August, 2018

Andrei Iancu
*Director of the United States Patent and Trademark Office*

Column 52,
Line 34, "514.373." should read --514.373,--.

Column 54,
Line 5, "287.2100." should read --287.2100,--.
Line 36, "306.1900." should read --306.1900,--.

Column 55,
Line 24, "534.3417." should read --534.3417,--.

Column 57,
Line 6, "C$_2$H$_{46}$N$_4$O$_6$" should read --C$_{28}$H$_{46}$N$_4$O$_6$--.
Line 7, "534.3417." should read --534.3417,--.

Column 58,
Line 9, "611.373." should read --611.373,--.

Column 62,
Line 12, "21.93;" should read --21.93.--.

Column 64,
Line 65, "δ6180.57," should read --δ 180.57,--.
Line 67, "20, 05, 20.04;" should read --20.05, 20.04.--.

Column 72,
Line 3, "575.2791." should read --575.2791,--.

Column 73,
Line 16, "364.1059." should read --364.1059,--.
Line 47, "598.2064." should read --598.2064,--.

Column 74,
Line 13, "680.3322." should read --680.3322,--.

Column 76,
Line 18, "450.2478." should read --450.2478,--.

Column 78,
Line 39, "5172.43," should read --δ 172.43,--.
Line 42, "564.3635." should read --564.3635,--.

Column 79,
Line 60, "217.1678." should read --217.1678,--.

Column 80,
Line 43, "362.1842." should read --362.1842,--.

Column 81,
Line 6, "594.3629." should read --594.3629,--.

Column 82,
Line 10, "483.2455." should read --483.2455,--.

Column 83,
Line 28, "δ5175.9," should read --δ 175.9,--.

Column 84,
Line 2, "604.2784." should read --604.2784,--.
Line 27, "603.3183." should read --603.3183,--.

Column 85,
Line 34, "390.1791." should read --390.1791,--.

Column 86,
Line 36, "650.3527." should read --650.3527,--.

Column 87,
Line 60, "259.1784." should read --259.1784,--.

Column 88,
Line 44, "404.1947." should read --404.1947,--.

Column 89,
Line 6, "678.3840." should read --678.3840,--.
Line 66, "Example 42 were" should read --Example 42 was--.

Column 90,
Line 29, "205.1137." should read --205.1137,--.
Line 46, "350.1300." should read --350.1300,--.

Column 91,
Line 8, "570.2546." should read --570.2546,--.

Column 92,
Lines 60-61, "(22-25° C.)" should read --(22-25° C.).--.

Column 96,
Line 51, "[$Ca^{2+}$]" should read --[$Ca^{2+}$]$_i$--.

Column 97,
Line 6, "high-K" should read --high-$K^+$--.
Line 37, "[$Ca^{2+}$]" should read --[$Ca^{2+}$]$_i$--.
Line 64, "comprising" should read --comprise--.